(12) United States Patent
Leblond et al.

(10) Patent No.: US 7,514,432 B2
(45) Date of Patent: Apr. 7, 2009

(54) COMPOUNDS AND METHODS OF TREATING CELL PROLIFERATIVE DISEASES, RETINOPATHIES AND ARTHRITIS

(75) Inventors: Bertrand Leblond, Rouen (FR); Silvère Petit, Lyons (FR); Virginie Picard, Paris (FR); Thierry Taverne, Saint Martin Boulogne sur Mer (FR); Fabien Schweighoffer, Vincennes (FR)

(73) Assignee: Exonhit Therapeutics SA, Paris (FR)

( * ) Notice: Subject to any disclaimer, the term of this patent is extended or adjusted under 35 U.S.C. 154(b) by 535 days.

(21) Appl. No.: 10/541,328

(22) PCT Filed: Feb. 27, 2004

(86) PCT No.: PCT/IB2004/000926

§ 371 (c)(1), (2), (4) Date: Aug. 30, 2005

(87) PCT Pub. No.: WO2004/076445

PCT Pub. Date: Sep. 10, 2004

(65) Prior Publication Data

US 2006/0183749 A1  Aug. 17, 2006

(30) Foreign Application Priority Data

Feb. 28, 2003  (EP) .................. 03290490

(51) Int. Cl.
*A61K 31/5377* (2006.01)
*C07D 413/14* (2006.01)

(52) U.S. Cl. ............ 514/235.2; 544/106; 544/124; 544/128; 544/242; 544/283; 546/112; 546/152; 514/231.2; 514/231.5; 514/233.5

(58) Field of Classification Search ........... 544/106, 544/111, 124, 127, 128, 224, 242, 253, 283; 514/231.2, 231.5, 233.5, 235.2; 546/112, 546/152

See application file for complete search history.

(56) References Cited

U.S. PATENT DOCUMENTS 4,644,071 A    2/1987    Masateru et al.
4,812,584 A *   3/1989    Masateru et al. ............ 549/417
6,552,073 B1 *   4/2003    Leblanc et al. ............. 514/460

FOREIGN PATENT DOCUMENTS

WO     03/074508 A    9/2003

OTHER PUBLICATIONS

International Search Report of PCT/IB2004/000926, mailed Aug. 18, 2004.
EP Search Report of EP 03 29 0490, mailed Jul. 29, 2003.
M. Yamato et al., "Synthesis and antitumor activity of tropolone derivatives.6.Structure-activity relationships of antitumor-active tropolone and 8-hydroxyquinoline derivatives", Journal of Medicinal Chemistry, Oct. 1987, vol. 30, No. 10, Oct. 1987, pp. 1897-1900, XP002291049.
Database Crossfire Beilstein 'Online! Beilstein Institut Zur Foerderung Der Wissenschaften, XP00249416.
M. Veverka et al., "Synthesis of some biologically active derivatives of 2-ydroxymethyl-5-hydorxy-4H-pyran-4-one", Collect. Czech. Chem. Commun., vol. 55, No. 3, 1990, pp. 833-840.

* cited by examiner

*Primary Examiner*—Golam M Shameem
(74) *Attorney, Agent, or Firm*—Nixon & Vanderhye P.C.

(57) ABSTRACT

The present invention relates to compounds and their uses, particularly in the pharmaceutical industry. The invention discloses compounds having anti-proliferative and antiangiogenic activities, as well as methods for treating various diseases associated with abnormal cell proliferation, including cancer, or associated with unregulated angiogenesis including growth and metastasis of solid tumors, ocular diseases and especially retinopathies, or arthritis, by administering said compounds. It further deals with pharmaceutical compositions comprising said compounds, more particularly useful to treat cancers (such as leukemia), ocular diseases and arthritis.

15 Claims, 6 Drawing Sheets

Figure 1:
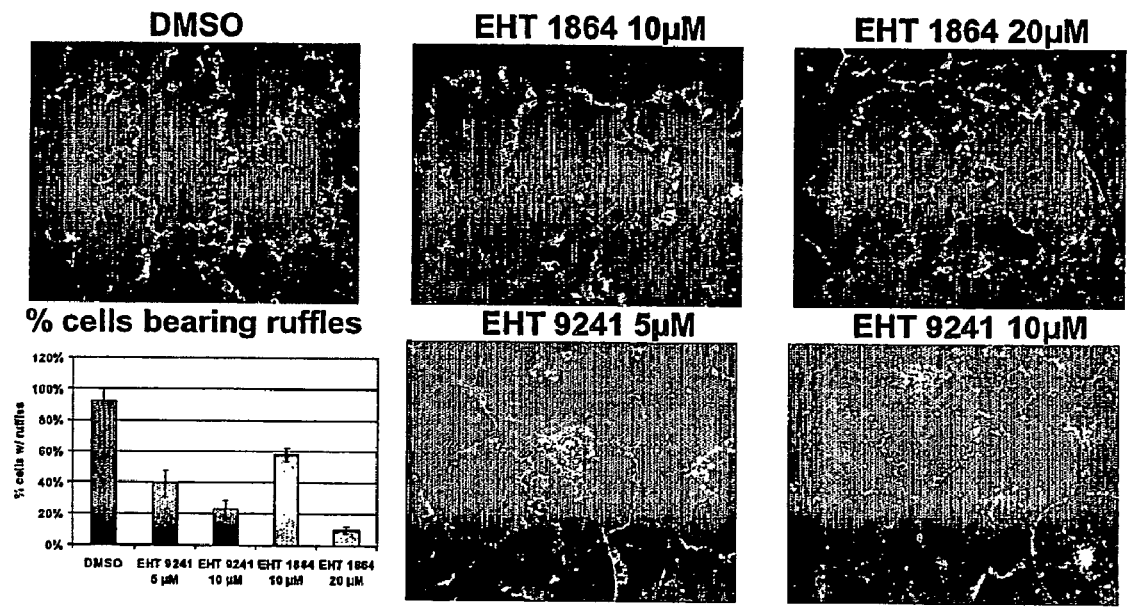

A.

B.

A.

B.

COMPOUNDS AND METHODS OF TREATING CELL PROLIFERATIVE DISEASES, RETINOPATHIES AND ARTHRITIS

This application is the U.S. national phase of international application PCT/IB2004/000926, filed 27 Feb. 2004 which designated the U.S. and claims priority of EP 03290490.6, filed 28 Feb. 2003, the entire contents of each of which are hereby incorporated by reference.

The invention relates to compounds and their uses, particularly in the pharmaceutical industry. The invention discloses compounds having anti-proliferative and antiangiogenic activities, as well as methods for treating various diseases associated with abnormal cell proliferation, including cancer, or associated with unregulated angiogenesis including growth and metastasis of solid tumors, ocular diseases and especially retinopathies, or arthritis, by administering said compounds. It further deals with pharmaceutical compositions comprising said compounds, more particularly useful to treat cancers, ocular diseases and arthritis.

Cancer is still one of the leading causes of death in developed countries, as cancer affects all ages, sexes, racial and ethnic groups. According to the American Association for Cancer Research, one out of five deaths in the US is caused by cancer. Worldwide, the most predominant cancer sites are lung (14%), prostate (13%), breast (11%) and colorectal (11%) (data obtained from the Cancer Statistic Branch, NCI).

Cancer rate is increasing in developed countries in spite of falling incidence of several cancers such as prostate cancer (due to detection programs) or lung cancer in men (due to prevention programs). Among the fastest increasing cancer rates are non-Hodgkin's lymphoma cancer and melanoma (3% annual rise) in the US (The Annual Report to the Nation on the Status of Cancer, 1973-1997).

Unlike cancer incidence, cancer deaths have declined in developed countries. This is due in part to better therapy designs but also to prevention programs and better detection of some cancers at an earlier stage.

However, in spite of higher achievements in treatment and prevention of cancers, several improvements are awaited for:
  effective therapies for early stage cancer to reduce relapses,
  alternative therapies for curing tumors refractory to standards therapies,
  alternative therapies for curing metastatic cancers
  less toxic drugs, and
  better delivery systems.

Inhibitors of cell signaling pathways could represent such a new alternative therapy by addressing the first three issues, when used alone or in combination with standard chemotoxic drugs. However as cell signaling pathways are ubiquitous, the toxicity of these inhibitors could be compared to the toxicity of standard chemotoxic drugs. To reduce their toxicity and enhance their tissue specificity, these inhibitors could be coupled to appropriate drug delivery systems.

U.S. Pat. No. 4,590,201 discloses compound CAI, a cell signaling inhibitor. This compound inhibits proliferation and inflammation by affecting the biochemical pathways necessary for signal processing in the cell. It is an indirect blocker of the effector enzymes which produce the second messengers necessary to induce growth.

Angiogenesis is a fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions, these molecules appear to maintain the microvascularity in a quiescent state for prolonged periods which may last for as long as weeks or, in some cases, decades. When necessary however (such as during wound repair), these same cells can undergo rapid proliferation and turnover within a 5 days period.

Although angiogenesis is a highly regulated process under normal conditions, many diseases are driven by persistent unregulated angiogenesis. Otherwise stated, unregulated angiogenesis may either cause a particular disease directly or exacerbate an existing pathological condition. For example, ocular neovascularization has been implicated as the most common cause of blindness and dominates approximately 20 eye diseases. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent. It has been shown for example that tumors which enlarge to greater than 2 mm, must obtain their own blood supply and do so by inducing the growth of new capillary blood vessels. Once these new blood vessels become embedded in the tumor, they provide a means for tumor cells to enter the circulation and metastasize to distant sites, such as liver, lung or bone. Although several angiogenesis inhibitors are currently under development for use in treating angiogenesis diseases, there are disadvantages associated with several of these compounds. For example, suramin is a potent angiogenesis inhibitor, but causes severe systemic toxicity in humans. Other compounds, such as retinoids, interferons and antiestrogens are safe for human use but have only a weak anti-angiogenic effect. Still other compounds may be difficult or costly to make.

The present invention now relates to the identification and characterization of a new class of compounds which present an anti-cell proliferation effect, more particularly on tumor cells and also an antiangiogenic effect. Advantageously, these compounds will inhibit or reverse malignant cell phenotypes in a wide array of human tissues, have little or no effect on normal cell physiology, will be highly active so that a limited number of treatments will be needed for each patient, and will have excellent bio availability and pharmacokinetic properties.

Accordingly, one aspect of the invention is to provide a compound having a general formula (I):

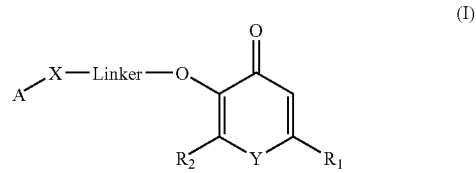

wherein:

$R_1$ is selected from the group consisting of:

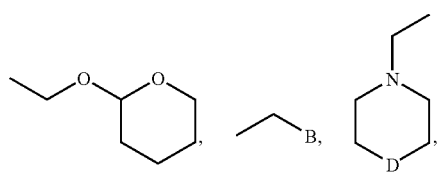

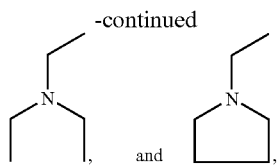

R₂ represents a hydrogen atom, an alkyl or alkenyl group containing from 3 to 6 carbon atoms;

B represents an halogen atom, preferably chlorine or fluorine, a hydroxyl group, a —O—CH₂—O—CH₃ (MOM) group, a —O—CH₂—O—CH₂—CH₂—O—CH₃ (MEM) group, a —OSO₂-alkyl group or a —OSi(CH₃)₂tBu;

D represents an oxygen atom, NR₃, CR'R" or a sulfur atom;

X represents an oxygen atom, a sulfur atom or a radical —NR₄—;

Y represents an oxygen atom, a sulfur atom or a radical —NR₄—;

R₃ represents a hydrogen, an alkyl group, a carboxylate group, an acyl group, a carboxamide group or a SO₂-alkyl group;

R' and R", identical or different, represent a hydrogen atom or an alkyl radical;

R₄, identical or different, is selected from a group consisting of a hydrogen atom, an alkyl group having from 1 to 10 carbon atoms, an aryl and an aralkyl;

"linker" represents (CH₂)ₙ, wherein n represents an integer between 1 and 10 inclusive, optionally interrupted by an heteroatom (preferably N, O, S and P) or a carbonyl group, or an aryldialkyl (preferably xylenyl) group;

A represents a group selected from:

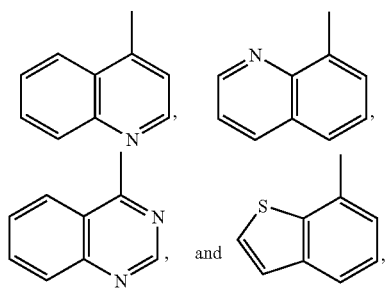

optionally A is substituted, its tautomers, optical and geometrical isomers, racemates, salts, hydrates and mixtures thereof.

The compounds of the present invention may have one or more asymmetric centers and it is intended that stereoisomers (optical isomers), as separated, pure or partially purified stereoisomers or racemic mixtures thereof are included in the scope of the invention.

The present invention also relates to pharmaceutical compositions comprising at least one compound as defined above in a pharmaceutically acceptable support, optionally in association with another active agent.

The pharmaceutical composition is more particularly intended to treat diseases of diseases associated with abnormal cell proliferation, such as cancers, or diseases associated with unregulated angiogenesis including growth and metastasis of solid tumors, ocular diseases and especially retinopathies (including diabetic retinopathies, retinal degenerative diseases, Age-Related Macular Degeneration (ARMD)), or arthritis.

The present invention also relates to the use of a compound as defined above, for the manufacture of a medicament for the treatment of diseases associated with abnormal cell proliferation, such as cancers or associated with unregulated angiogenesis, including growth and metastasis of solid tumors, ocular diseases and especially retinopathies (including diabetic retinopathies, retinal degenerative diseases, Age-Related Macular Degeneration (ARMD)), or arthritis.

The present invention also includes methods of treating diseases associated with unregulated angiogenesis including growth and metastasis of solid tumors, ocular diseases and especially retinopathies and arthritis and diseases associated with abnormal cell proliferation, such as cancers, comprising the administration to a subject in need thereof of an effective amount of a compound as defined above.

As will be further disclosed in this application, the compounds according to this invention have strong cell proliferation inhibitory activity and are effective at reducing or arresting growth of proliferating cells such as tumor cells.

PREFERRED EMBODIMENTS

Within the context of the present application, the terms alkyl and alkoxy denote linear or branched saturated groups containing from 1 to 10 carbon atoms. An alkoxy group denotes an —O-alkyl group.

The alkyl groups may be linear or branched. Examples of alkyl groups having from 1 to 10 carbon atoms inclusive are methyl, ethyl, propyl, isopropyl, t-butyl, n-butyl, pentyl, hexyl, heptyl, octyl, nonyl, decyl, 2-ethylhexyl, 2-methylbutyl, 2-methylpentyl, 1-methylhexyl, 3-methylheptyl and the other isomeric forms thereof. Preferably, the alkyl groups have from 1 to 6 carbon atoms.

The alkenyl groups may be linear or branched. Examples of alkenyl containing from 3 to 6 carbon atoms are 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl and the isomeric forms thereof.

The term aryl includes any aromatic group comprising preferably from 5 to 14 carbon atoms, preferably from 6 to 14 carbon atoms, optionally interrupted by one or several heteroatoms selected from N, O, S or P. Most preferred aryl groups are mono- or bi-cyclic and comprises from 6 to 14 carbon atoms, such as phenyl, α-naphtyl, β-naphtyl, antracenyl, or fluorenyl group.

The term aralkyl group generally stands for an aryl group attached to an alkyl group as defined above, such as benzyl or phenethyl.

The term carboxylate group generally stands for a group presenting a —COO—R radical, wherein R represents a hydrogen atom, an aryl group, or preferably an alkyl radical. In this respect, R3 represents preferably a tert-butyl-carboxylate group.

The term acyl group generally stands for a —COR group, wherein R represents an aryl group, or preferably an alkyl radical. In this respect, R3 represents preferably an acetyl, a pivaloyl, or a benzoyl group.

The term carboxamide group generally stands for a —CONR'R" group, wherein R' and R", identical or different, are as defined above. In this respect, R3 represents preferably an N,N-diethyl- or N,N-diisopropyl-carboxamide group or a N-tert-butyl- or N-methyl-carboxamide group.

According to a particular embodiment, A is substituted with at least one substituent, which may be selected from the group consisting of: a hydrogen atom, a halogen atom (preferably F, Cl, or Br), a hydroxyl group, a $(C_1-C_{10})$alkyl group, an alkenyl group, an $(C_1-C_{10})$alkanoyl group, a $(C_1-C_{10})$ alkoxy group, an $(C_1-C_{10})$alkoxycarbonyl (or carboxylate) group, an aryl group, an aralkyl group, an arylcarbonyl group, a mono- or poly-cyclic hydrocarbon group, a —NHCO($C_1$-$C_6$)alkyl group, —NO$_2$, —CN, a —NR$_5$R$_6$ group or a trifluoro($C_1$-$C_6$)alkyl group, R$_5$ and R$_6$, independently from each other, are selected from the group consisting of a hydrogen atom, an alkyl group having from 1 to 10 carbon atoms, an aryl and an aralkyl.

An alkanoyl group is a —CO-alkyl group, the alkyl group being as defined above.

The term arylcarbonyl group generally stands for an aryl group attached to a carbonyl group, the aryl group being as defined above.

The term alkoxycarbonyl group generally stands for an alkoxy group attached to a carbonyl group, the alkoxy group being as defined above.

The term mono- or poly-cyclic hydrocarbon group is understood to refer to hydrocarbon cyclic group having from 1 to 20 carbon atoms, optionally interrupted with one or more heteroatoms selected in the group N, O, S and P. Among such mono- or poly-cyclic hydrocarbon groups, cyclopentyl, cyclohexyl, cycloheptyl, 1- or 2-adamantyl groups, pyran, piperidine, pyrrolidine, morpholine, dioxan, tetrahydrothiophene, and tetrahydrofuran can be cited. The mono- or poly-cyclic hydrocarbon group may form with the phenyl group it is attached an aryl group, such as a α-naphtyl, β-naphtyl, or antracenyl group.

Where the linker represents $(CH_2)_n$, interrupted by an heteroatom, the heteroatom is more preferably an oxygen atom. In this case, the linker is advantageously a —CH$_2$CH$_2$OCH$_2$CH$_2$— group. Where the linker represents $(CH_2)_n$ interrupted by a carbonyl group, said linker may represent a —(C=O)CH$_2$CH$_2$CH$_2$CH$_2$— group (preferably when X is —NR$_4$—).

The groups identified above may be optionally substituted. In particular, the alkyl, alkenyl, aryl, aralkyl, and the mono- or poly-cyclic hydrocarbon group may be optionally substituted with one or more groups selected from hydroxyl group, halogen atom, cyano group, nitro group, ester (—COO($C_1$-$C_6$) alkyl group), —OCO($C_1$-$C_6$)alkyl group, amide (—NHCO ($C_1$-$C_6$)alkyl or —CONH($C_1$-$C_6$)alkyl group), $(C_1$-$C_{10})$alkyl radical, $(C_1$-$C_{10})$alkoxy radical, mono- or poly-cyclic hydrocarbon group, C=O group, a —NR$_5$R$_6$ group or a trifluoro ($C_1$-$C_6$)alkyl group, R$_5$ and R$_6$ being as defined above.

The trifluoro($C_1$-$C_6$)alkyl group is preferably the trifluoromethyl group.

According to preferred embodiments, the compounds according to the invention correspond to general formula (I) wherein:

X is sulfur, —NH— or preferably oxygen; and/or

Y is oxygen; and/or

"linker" represents $(CH_2)_n$, wherein n is from 2 to 9, preferably 4 to 7, inclusive, or the meta, ortho or para-xylenyl groups, —CH$_2$CH$_2$OCH$_2$CH$_2$— and —(C=O) CH$_2$CH$_2$CH$_2$CH$_2$—); and/or R$_1$ is

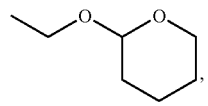

—CH$_2$N(Et$_2$) and —CH$_2$pyrrolidine,

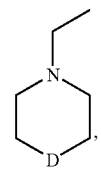

wherein D is oxygen, sulfur, —CH$_2$— or NR$_3$, wherein R$_3$ preferably represents H or an alkyl group (said alkyl is more specifically a methyl radical), and —CH$_2$—B, wherein B is a —O—CH$_2$O—CH$_3$ group or —OSO$_2$-alkyl group (wherein alkyl is preferably methyl) or halogen (preferably chlorine of fluorine); and/or R$_2$ is a hydrogen atom; and/or A is a substituted group as defined above.

In a particular embodiment, when A is a substituted group as defined above, at least one of the substituents is a halogen atom, more preferably chlorine or fluorine.

A particular preferred group of compounds according to the present invention, are the compounds of formula (I) wherein at least one of the substituents, and more preferably all the substituents, of A represents a hydrogen atom, a methyl group, a propyl group, an ethoxy group, an halogen atom, preferably chlorine or fluorine, or the CF$_3$ group.

When the compounds according to the invention are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. Mixture of solvents may be used. Organic bases like lysine, arginine, diethanolamine, choline, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents may also be used.

Specific examples of compounds of formula (I) which fall within the scope of the present invention include the following compounds:

2-(Tetrahydro-pyran-2-yloxymethyl)-5-[5-(7-trifluoromethyl-quinolin-4-yloxy)-pentyloxy]-pyran-4--one (EHT 3788)

5-[5-(6-Fluoro-2-methyl-quinolin-4-yloxy)-pentyloxy]-2-(tetrahydro-pyran-2-yloxymethyl)-4H-pyran-4--one (EHT 1593)

5-[5-(6-Fluoro-2-trifluoromethyl-quinolin-4-yloxy)-pentyloxy]-2-(tetrahydro-pyran-2-yloxymethyl)-4H-pyran-4-one (EHT 1074)

5-[5-(7-Propyl-quinolin-8-yloxy)-pentyloxy]-2-(tetrahydro-pyran-2-yloxymethyl)-4H-pyran-4-one (EHT 5810)

5-[5-(Benzo[b]thiophen-7-yloxy)-pentyloxy]-2-(tetrahydro-pyran-2-yloxymethyl)-4H-pyran-4-one (EHT 6060)

2-(Tetrahydro-pyran-2-yloxymethyl)-5-[5-(7-trifluoromethyl-quinolin-4-ylsulfanyl)-pentyloxy]-4H-pyran-4-one (EHT 9376)

2-(Tetrahydro-pyran-2-yloxymethyl)-5-[4-(7-trifluoromethyl-quinolin-4-ylsulfanyl)-butoxy]-4H-pyran-4--one (EHT 4745)

2-(Tetrahydro-pyran-2-yloxymethyl)-5-[6-(7-trifluoromethyl-quinolin-4-ylsulfanyl)-hexyloxy]-4H-pyran-4--one (EHT 6271)

2-Hydroxymethyl-5-[5-(7-trifluoromethyl-quinolin-4-ylsulfanyl)-pentyloxy]-4H-pyran-4-one hydrochloride salt (EHT 1302)

2-Hydroxymethyl-5-[5-(7-trifluoromethyl-quinolin-4-ylsulfanyl)-pentyloxy]-4H-pyran-4-one (EHT 5909)

2-Methoxymethoxymethyl-5-[5-(7-trifluoromethyl-quinolin-4-ylsulfanyl)-pentyloxy]-4H-pyran-4-one (EHT 2168)

2-Chloromethyl-5-[5-(7-trifluoromethyl-quinolin-4-ylsulfanyl)-pentyloxy]-4H-pyran-4-one (EHT 1494)

2-(4-Methyl-piperazin-1-ylmethyl)-5-[5-(7-trifluoromethyl-quinolin-4-ylsulfanyl)-pentyloxy]-4H-pyran-4--one (EHT 7365)

2-Morpholin-4-ylmethyl-5-[5-(7-trifluoromethyl-quinolin-4-ylsulfanyl)-pentyloxy]-4H-pyran-4-one (EHT 7168)

5-(5-(7-(Trifluoromethyl)quinolin-4-ylthio)pentyloxy)-2-(fluoromethyl)-4H-pyran-4-one (EHT 8817)

5-(5-(7-(Trifluoromethyl)quinolin-4-ylthio)pentyloxy)-2-((piperidin-1-yl)methyl)-4H-pyran-4--one (EHT 9317)

5-(5-(7-(Trifluoromethyl)quinolin-4-ylthio)pentyloxy)-2-(thiomorpholino-methyl)-4H-pyran-4-one (EHT 5430)

2-((Diethylamino)methyl)-5-(5-(7-(trifluoromethyl)quinolin-4-ylthio)pentyloxy)-4H-pyran-4-one (EHT 7370)

5-(5-(Quinazolin-4-yloxy)pentyloxy)-2-(morpholinomethyl)-4H-pyran-4-one (EHT 3726)

5-(5-(Quinazolin-4-yloxy)pentyloxy)-2-((4-methylpiperazin-1-yl)methyl)-4H-pyran-4-one (EHT 4063)

4-[5-(6-Morpholin-4-ylmethyl-4-oxo-4H-pyran-3-yloxy)-pentyloxy]-7-trifluoromethyl-quinoline-3-carboxylic acid ethyl ester (EHT 8935)

5-(5-(Quinazolin-4-yloxy)pentyloxy)-2-((pyrrolidin-1-yl)methyl)-4H-pyran-4-one (EHT 5317)

5-(5-(8-(Trifluoromethyl)quinolin-4-yloxy)pentyloxy)-2-((4-methylpiperazin-1-yl)methyl)-4H-pyran-4-one (EHT 5847)

5-(5-(8-(Trifluoromethyl)quinolin-4-yloxy)pentyloxy)-2-(morpholinomethyl)-4H-pyran-4-one (EHT 4687)

5-(5-(7-(Trifluoromethyl)quinolin-4-yloxy)pentyloxy)-2-(morpholinomethyl)-4H-pyran-4-one (EHT 3411)

5-(5-(7-(Trifluoromethyl)quinolin-4-yloxy)pentyloxy)-2-((4-methylpiperazin-1-yl)methyl)-4H-pyran-4-one (EHT 0079)

5-(5-(6-(Trifluoromethyl)quinolin-4-yloxy)pentyloxy)-2-(morpholinomethyl)-4H-pyran-4-one (EHT 1426)

4-[5-(6-(4-Methyl-piperazin-1-ylmethyl)-4-oxo-4H-pyran-3-yloxy)-pentyloxy]-7-trifluoromethyl-quinoline-3-carboxylic acid ethyl ester (EHT 8791)

4-[5-(6-(4-Methyl-piperazin-1-ylmethyl)-4-oxo-4H-pyran-3-yloxy)-pentyloxy]-7-trifluoromethyl-quinoline-3-carboxylic acid ethyl ester (EHT 2725)

5-((4-((7-(Trifluoromethyl)quinolin-4-ylthio)methyl)phenyl)methoxy)-2-(morpholinomethyl)-4H-pyran-4-one (EHT 2218)

5-((2-((7-(Trifluoromethyl)quinolin-4-ylthio)methyl)phenyl)methoxy)-2-(morpholinomethyl)-4H-pyran-4-one (EHT 9069)

5-(5-(7-(Trifluoromethyl)quinolin-4-ylthio)pentyloxy)-2-((4-acetylpiperazin-1-yl)methyl)-4H-pyran-4-one (EHT 3980)

4-((5-(5-(7-(Trifluoromethyl)quinolin-4-ylthio)pentyloxy)-4-oxo-4H-pyran-2-yl)methyl)-N,N-diethylpiperazine-1-carboxamide (EHT 5743)

5-(5-(7-(Trifluoromethyl)quinolin-4-ylthio)pentyloxy)-2-((4-(pivaloyl)piperazin-1-yl)methyl)-4H-pyran-4-one (EHT 0785)

4-((5-(5-(7-(Trifluoromethyl)quinolin-4-ylthio)pentyloxy)-4-oxo-4H-pyran-2-yl)methyl)-N,N-di-isopropylpiperazine-1-carboxamide (EHT 0566)

5-(5-(7-(Trifluoromethyl)quinolin-4-ylthio)pentyloxy)-2-((4-methylsulfonylpiperazin-1-yl)methyl)-4H-pyran-4-one (EHT 8366)

4-((5-(5-(7-(Trifluoromethyl)quinolin-4-ylthio)pentyloxy)-4-oxo-4H-pyran-2-yl)methyl)-N-tert-butylpiperazine-1-carboxamide (EHT 3664)

4-((5-(5-(7-(Trifluoromethyl)quinolin-4-ylthio)pentyloxy)-4-oxo-4H-pyran-2-yl)methyl)-N-methylpiperazine-1-carboxamide (EHT 4495)

5-(6-(Morpholinomethyl)-4-oxo-4H-pyran-3-yloxy)-N-(7-(trifluoromethyl)quinolin-4-yl)pentanamide (EHT 6037)

5-(2-(2-(7-(Trifluoromethyl)quinolin-4-ylthio)ethoxy)ethoxy)-2-morpholinomethyl-4H-pyran-4-one (EHT 0371)

5-(5-(7-(Trifluoromethyl)quinolin-4-ylthio)pentyloxy)-2-(morpholinomethyl)-4H-pyran-4-one dihydrochloride (EHT 1864)

5-((3-((7-(Trifluoromethyl)quinolin-4-ylthio)methyl)phenyl)methoxy)-2-(morpholinomethyl)-4H-pyran-4-one dihydrochloride (EHT 0434)

tert-Butyl 4-((5-(5-(7-(trifluoromethyl)quinolin-4-ylthio)pentyloxy)-4-oxo-4H-pyran-2-yl)methyl)piperazine-1-carboxylate (EHT 9358)

tert-Butyl 4-((5-(5-(7-chloroquinolin-4-yloxy)pentyloxy)-4-oxo-4H-pyran-2-yl)methyl)piperazine-1-carboxylate (EHT 2580)

5-(5-(7-(Trifluoromethyl)quinolin-4-ylthio)pentyloxy)-2-((4-methylpiperazin-1-yl)methyl)-4H-pyran-4-one trihydrochloride (EHT 9241)

5-(5-(7-(Trifluoromethyl)quinolin-4-ylthio)pentyloxy)-2-((piperazin-1-yl)methyl)-4H-pyran-4-one trihydrochloride (EHT 8560)

5-(5-(7-Chloroquinolin-4-yloxy)pentyloxy)-2-((piperazin-1-yl)methyl)-4H-pyran-4-one (EHT 0872)

5-(2-(7-(Trifluoromethyl)quinolin-4-ylthio)ethoxy)-2-((tetrahydro-2H-pyran-2-yloxy)methyl)-4H-pyran-4-one (EHT 5575)

5-(8-(7-(Trifluoromethyl)quinolin-4-ylthio)octyloxy)-2-((tetrahydro-2H-pyran-2-yloxy)methyl)-4H-pyran-4-one (EHT 1006)

5-(7-(7-(Trifluoromethyl)quinolin-4-ylthio)heptyloxy)-2-((tetrahydro-2H-pyran-2-yloxy)methyl)-4H-pyran-4-one (EHT 8883)

5-(2-(7-(Trifluoromethyl)quinolin-4-yloxy)ethoxy)-2-(morpholinomethyl)-4H-pyran-4-one (EHT 6892).

Particularly preferred compounds are EHT 9241, its free base EHT 7365, EHT 8560, EHT 1864, its free base EHT 7168 and EHT 5743.

The compounds according to the present invention may be prepared by various methods known to those skilled in the art. More preferably, several chemical routes have been carried out.

The first one (Scheme 1) relates to compounds included in the structures C which can be obtained in two steps starting from compound A (described by Miyano, M.; Deason, J. R.; Nakao, A.; Stealey, M. A.; Villamil, C. I.; et al. *J. Med. Chem.* 1988; 31, 1052-1061).

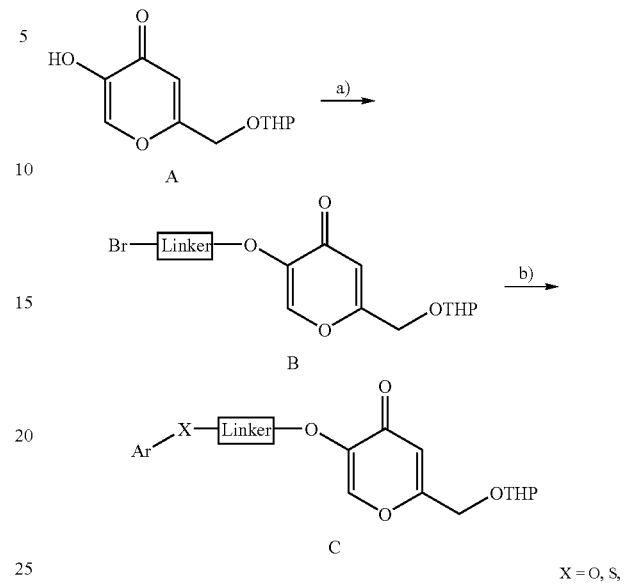

Scheme 1

Compound A can be treated under alkylation conditions preferably conducted in a solvent, such as DMF or THF, at a temperature between 5° C. and 100° C., typically around 80° C. using a base such as cesium carbonate ($Cs_2CO_3$) or NaH and a dihalogenoalkane or dihalogenoarylalkane (step a) (table 1).

The resulting alkylated products of formula B (1-5) can be substituted to obtain compounds of formula C in a reaction (step b) involving a base such as NaH or cesium carbonate and a nucleophile such 4-quinolinol, 4-quinoline-thiol, 7-benzo[b]thiophenol, 7-propyl-quinolin-8-ol non substituted or substituted derivatives as described in table 2. The preferred solvents are DMF, THF or DMSO and the reaction is conducted at a temperature between 25° C. and 100° C.

TABLE 1

| Alkylating Agent | Conditions | Linker | Yield | Cpds nb |
|---|---|---|---|---|
| Br-(CH₂)₄-Br | $Cs_2CO_3$, DMF, 80° C., 2.5 h | -(CH₂)₄- | 71% | 2 |
| Br-(CH₂)₅-Br | $Cs_2CO_3$, DMF, 80° C., 2.5 h | -(CH₂)₅- | 95% | 1 |

TABLE 1-continued

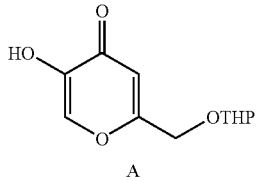

| Alkylating Agent | Conditions | Linker | Yield | Cpds nb |
|---|---|---|---|---|
| Br-(CH₂)₆-Br | Cs$_2$CO$_3$, DMF, 80° C., 2.5 h | 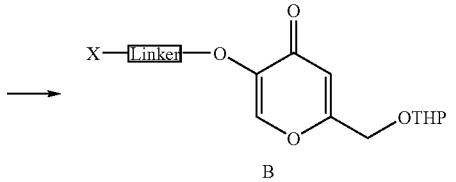 | 23% | 3 |
| Br-(CH₂)₇-Br | Cs$_2$CO$_3$, DMF, 80° C., 2.5 h | 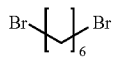 | 79% | 4 |
| Br-(CH₂)₈-Br | Cs$_2$CO$_3$, DMF, 80° C., 2.5 h | 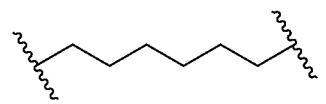 | 62% | 5 |

TABLE 2

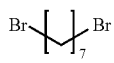

| Nucleophile ArXH | Conditions | Linker | Yield | Cpds nb |
|---|---|---|---|---|
| 7-trifluoromethyl-quinolin-4-thiol | NaH, DMF, 25° C. | 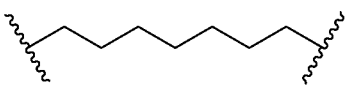 | 64% | EHT 4745 |
| 7-trifluoromethyl-quinolin-4-thiol | NaH, DMF, 25° C. | 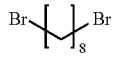 | 47% | EHT 9376 |
| 7-trifluoromethyl-quinolin-4-thiol | NaH, DMF, 25° C. | 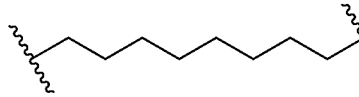 | 33% | EHT 6271 |
| 7-trifluoromethyl-quinolin-4-thiol | NaH, DMF, 25° C. | 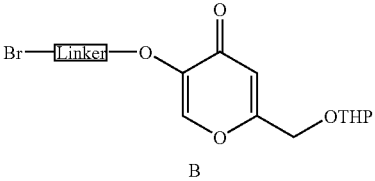 | 43% | EHT 8883 |
| 7-trifluoromethyl-quinolin-4-thiol | NaH, DMF, 25° C. | 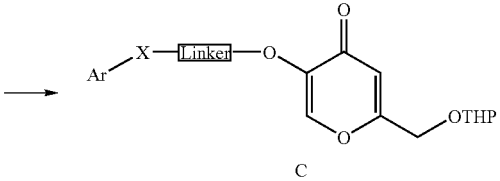 | 47% | EHT 1006 |
| 7-trifluoromethyl-quinolin-4-ol | NaH, DMF, 25° C. | 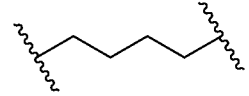 | 18% | EHT 3788 |

TABLE 2-continued

Scheme showing conversion of compound B (Br—Linker—O—pyranone—CH2—OTHP) to compound C (Ar—X—Linker—O—pyranone—CH2—OTHP).

| Nucleophile ArXH | Conditions | Linker | Yield | Cpds nb |
|---|---|---|---|---|
| 6-fluoro-2-trifluoromethyl-quinolin-4-ol | NaH, DMSO, 60° C. | (hexyl chain) | 12% | EHT 1074 |
| 6-fluoro-2-methyl-quinolin-4-ol | NaH, DMSO, 60° C. | (hexyl chain) | 20% | EHT 1593 |
| benzo[b]thiophen-7-ol | NaH, THF, 25° C. | (hexyl chain) | 3% | EHT 6060 |
| 7-propyl-quinolin-8-ol | NaH, DMSO, 60° C. | (hexyl chain) | 25% | EHT 5810 |

The second chemical route (Scheme 2) used the EHT 9376 compound which can be deprotected to the corresponding alcohol EHT 1302 (hydrochloride salt) in methanol with an acid source (MeOH, HCl) such as Dowex resin 50WX8-200 at a temperature comprised between 5° C. and 30° C., typically around 25° C.

Scheme 2

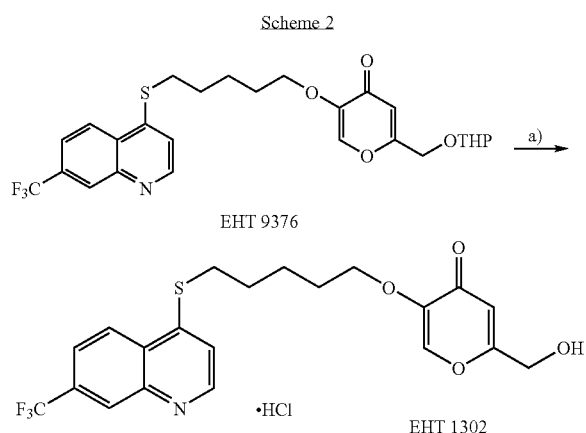

In the third chemical route (Scheme 3) Intermediate 7 can be prepared from the silylated ether 6 (6 was described by Sefkow, M.; Kaatz, H. *Tetrahedron Lett,* 1999, 40, 6561-6562) with a base such as cesium carbonate and 1,5-dibromopentane in dimethylformamide at 50° C. (Scheme 3).

Derivative 8 can be prepared from intermediate 7 using sodium hydride, 7-trifluoromethyl-4-quinoline-thiol in dimethylformamide at room temperature. Subsequent deprotection of silylated ether 8 using n-tetrabutylammonium fluoride (TBAF) in tetrahydrofuran at room temperature led to alcohol EHT 5909 (scheme 3).

MOM derivative EHT 2168 can be obtained from alcohol EHT 5909 with sodium hydride and methylchloromethyl ether in tetrahydrofuran at room temperature. Chloro, mesylate and fluoro derivatives (EHT 1494, 9 and EHT 8817) can be prepared from alcohol EHT 5909 using respectively methanesulfonyl chloride and triethylamine in dichloromethane at room temperature or diethylaminosulfur trifluoride (DAST) in dichloromethane (Scheme 3).

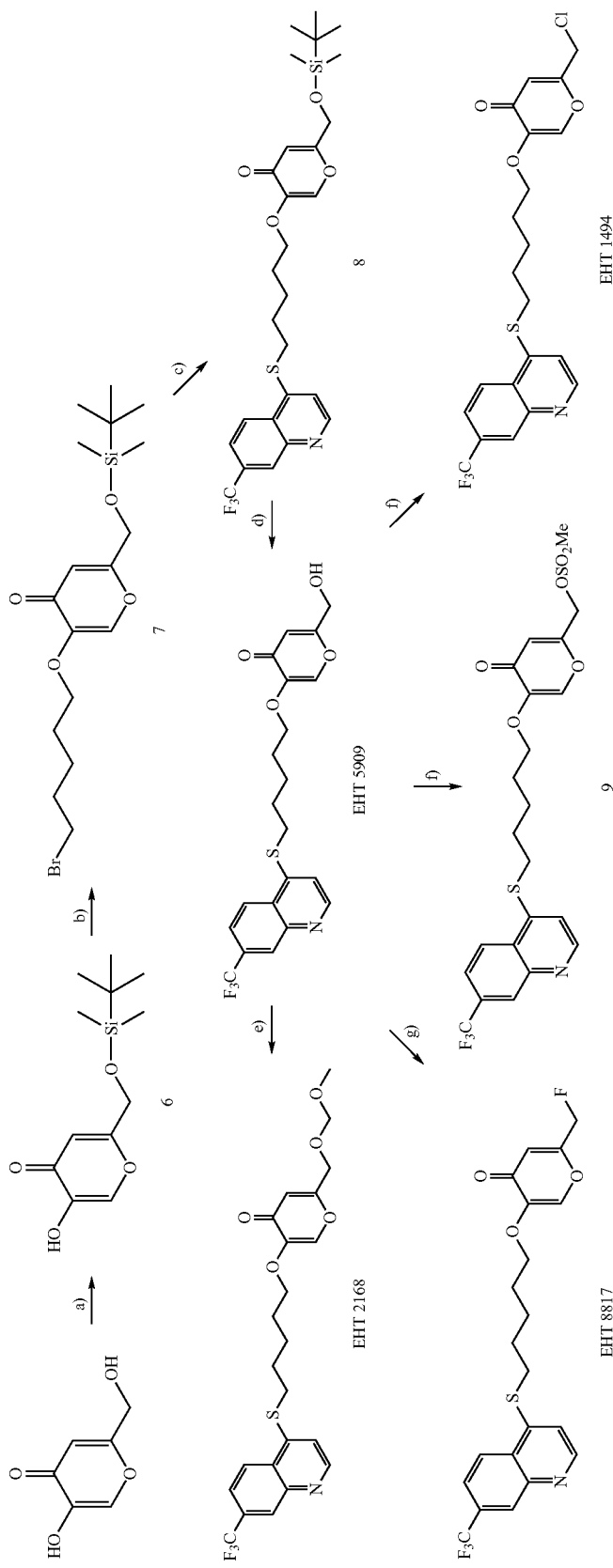
Scheme 3
a) TBDMSCl, CH$_2$Cl$_2$, TEA, RT.
b) Cs$_2$CO$_3$, DMF, dibromopentane, 50° C.
c) 7-trifluoromethyl-4-quinoline-thiol, NaH, DMF, RT.
d) TBAF, THF, RT
e) MOMCl, NaH, THF, RT.
f) CH$_3$SO$_2$Cl, TEA, CH$_2$Cl$_2$, RT.
g) DAST, CH$_2$Cl$_2$.

For the above described series, yields are generally comprised between 55 and 90% by weight, more specifically between 55 and 75% by weight. These methods for preparing compounds of formula (I) represent further objects of the present application.

In an other chemical route alcohols 11-15 were prepared from 5-(5-bromopentyloxy)-2-(hydroxymethyl)-4H-pyran-4-one 10 in DMF using a base such as cesium carbonate ($Cs_2CO_3$) at a temperature between 5° C. and 100° C., typically around 80° C. Intermediate 10 was prepared by alkylation of kojic acid using 1,5-dibromopentane in DMF and using a base $Cs_2CO_3$ at 110° C. in 46% yield (Table 3).

TABLE 3

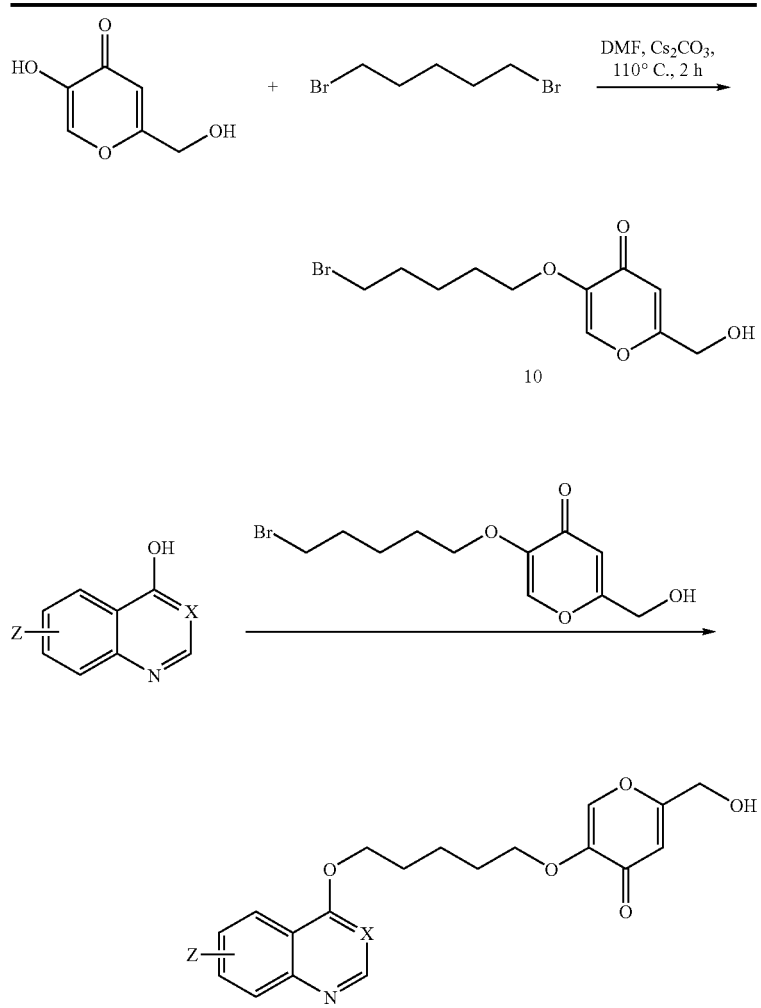

| X | Z | Conditions | Yield | Cpds # |
|---|---|---|---|---|
| CH | 6-$CF_3$ | DMF, $Cs_2CO_3$, 50° C., 22 h | 21% | 11 |
| CH | 7-$CF_3$ | DMF, $Cs_2CO_3$, 75° C., 15 h | 47% | 12 |
| C—COOEt | 7-$CF_3$ | DMF, $Cs_2CO_3$, 50° C., 22 h | 31% | 13 |
| CH | 8-$CF_3$ | DMF, $Cs_2CO_3$, 50° C., 18 h | 35% | 14 |
| N | H | DMF, $Cs_2CO_3$, 50° C., 2 h | 26% | 15 |

Alcohols 11-15 and EHT 5909 reacted respectively with methanesulfonyl chloride in presence of a base such triethylamine in dichloromethane at temperatures comprise between 0° C. and room temperature for 1 h to 18 h to yield to the mesylate derivatives 16-20 and 9 (Table 4).

TABLE 4

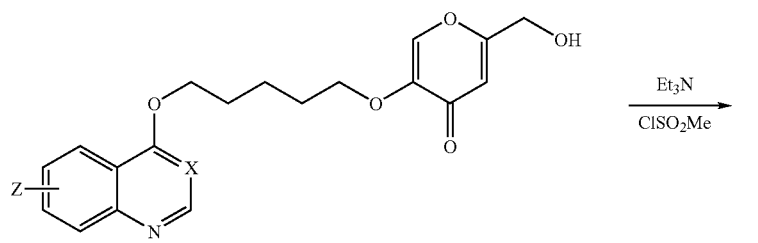

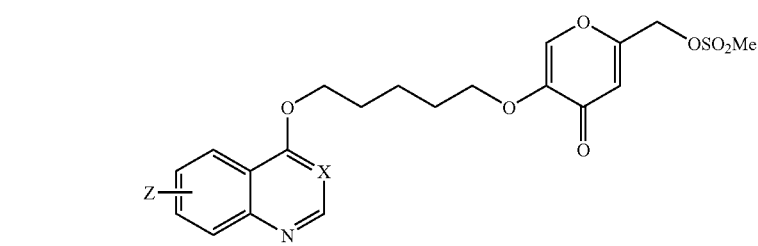

| X | Z | SM Cpds # | Conditions | Yield | Cpds # |
|---|---|---|---|---|---|
| CH | 6-$CF_3$ | 11 | $CH_2Cl_2$, 0° C. then RT, 1.5 h | 90.5% | 16 |
| CH | 7-$CF_3$ | 12 | $CH_2Cl_2$, 0° C. then RT, 1.5 h | 91% | 17 |
| C—COOEt | 7-$CF_3$ | 13 | $CH_2Cl_2$, 0° C. then RT, 1 h | 65% | 18 |
| CH | 8-$CF_3$ | 14 | $CH_2Cl_2$, 0° C. then RT, 1 h | 37% | 19 |
| N | H | 15 | $CH_2Cl_2$, 0° C. then RT, 1 h | 99% | 20 |

The mesylate derivative 9 reacted with nucleophiles, primary and secondary amines, such as respectively piperidine, thiomorpholine, diethylamine, morpholine and N-methylpiperazine at reflux in dichloromethane between 1 h to 4 h to yield to EHT 9317, EHT 5430, EHT 7370, EHT 7168 and EHT 7365 (Table 5).

TABLE 5
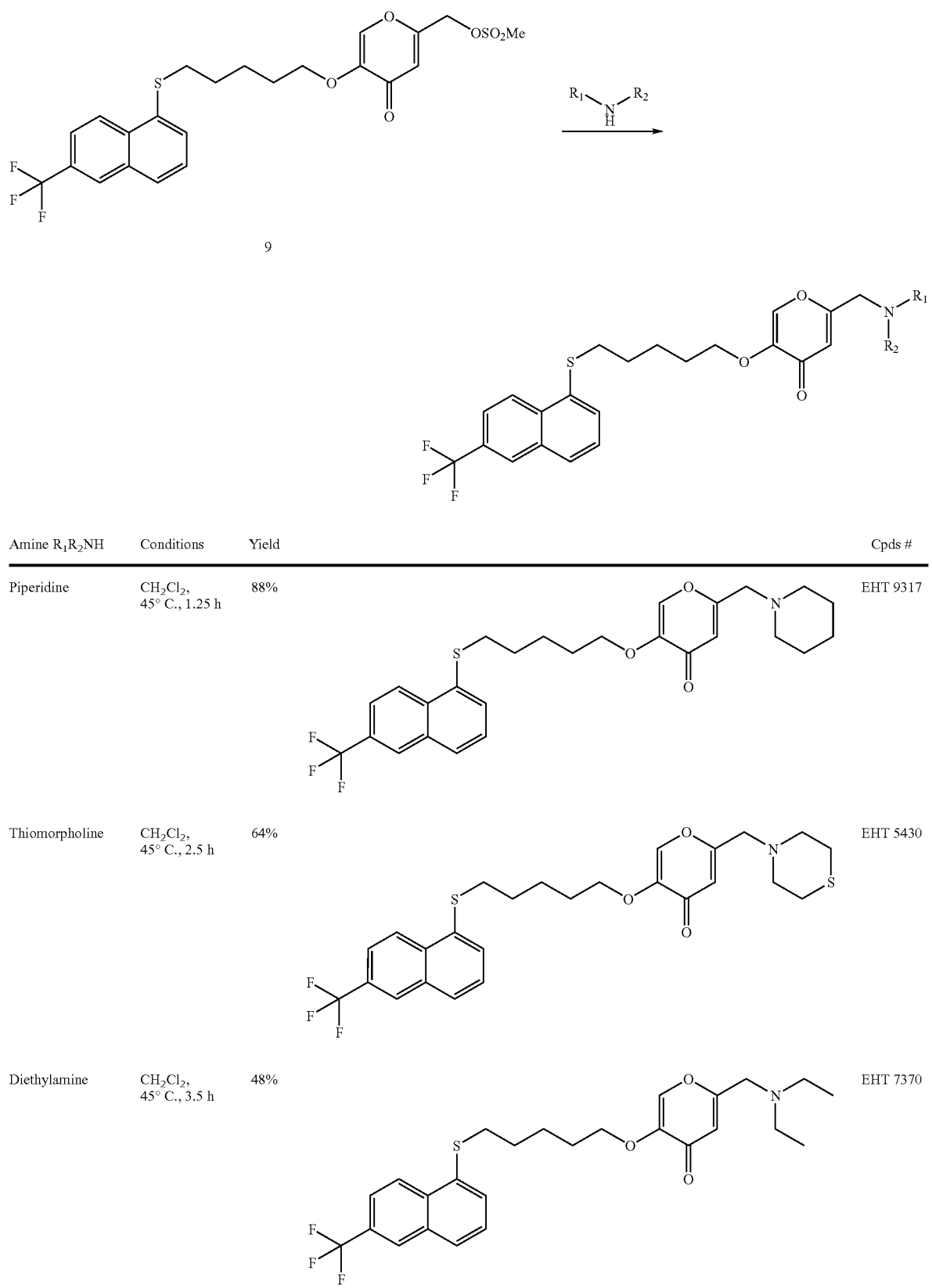
| Amine $R_1R_2NH$ | Conditions | Yield | | Cpds # |
|---|---|---|---|---|
| Piperidine | $CH_2Cl_2$, 45° C., 1.25 h | 88% | | EHT 9317 |
| Thiomorpholine | $CH_2Cl_2$, 45° C., 2.5 h | 64% | | EHT 5430 |
| Diethylamine | $CH_2Cl_2$, 45° C., 3.5 h | 48% | | EHT 7370 |

TABLE 5-continued
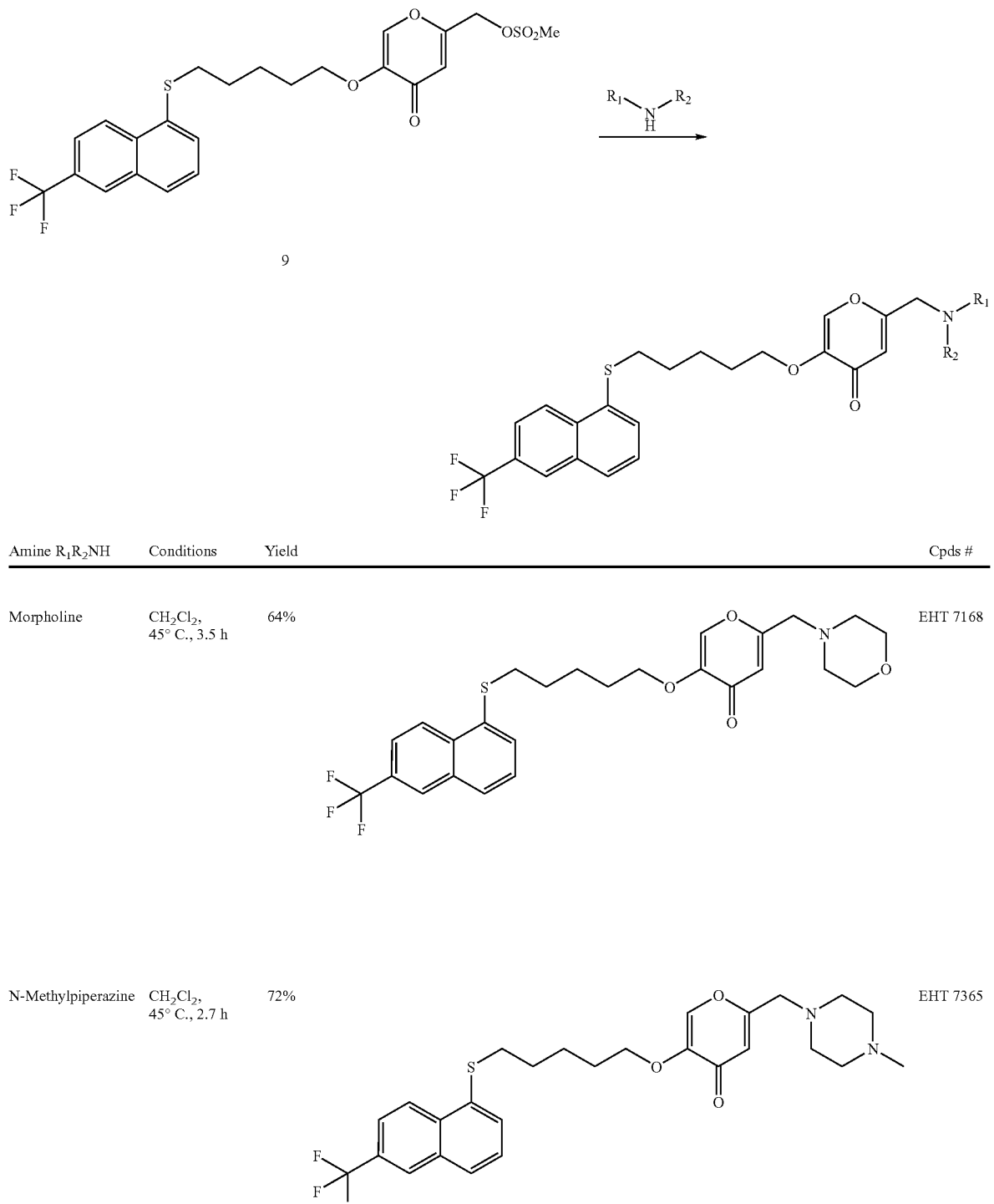
| Amine R₁R₂NH | Conditions | Yield | | Cpds # |
|---|---|---|---|---|
| Morpholine | CH₂Cl₂, 45° C., 3.5 h | 64% | | EHT 7168 |
| N-Methylpiperazine | CH₂Cl₂, 45° C., 2.7 h | 72% | | EHT 7365 |
Similarly the mesylate derivatives 16-20 were substituted by nucleophiles such primary and secondary amines (morpholine, N-methylpiperazine, thiomorpholine, diethylamine, piperidine) to obtain EHT 1426, EHT 0079, EHT 3411, EHT 8791, EHT 8935, EHT 5847, EHT 4867, EHT 5317, EHT 3726 and EHT 4063 (Table 6).

TABLE 6
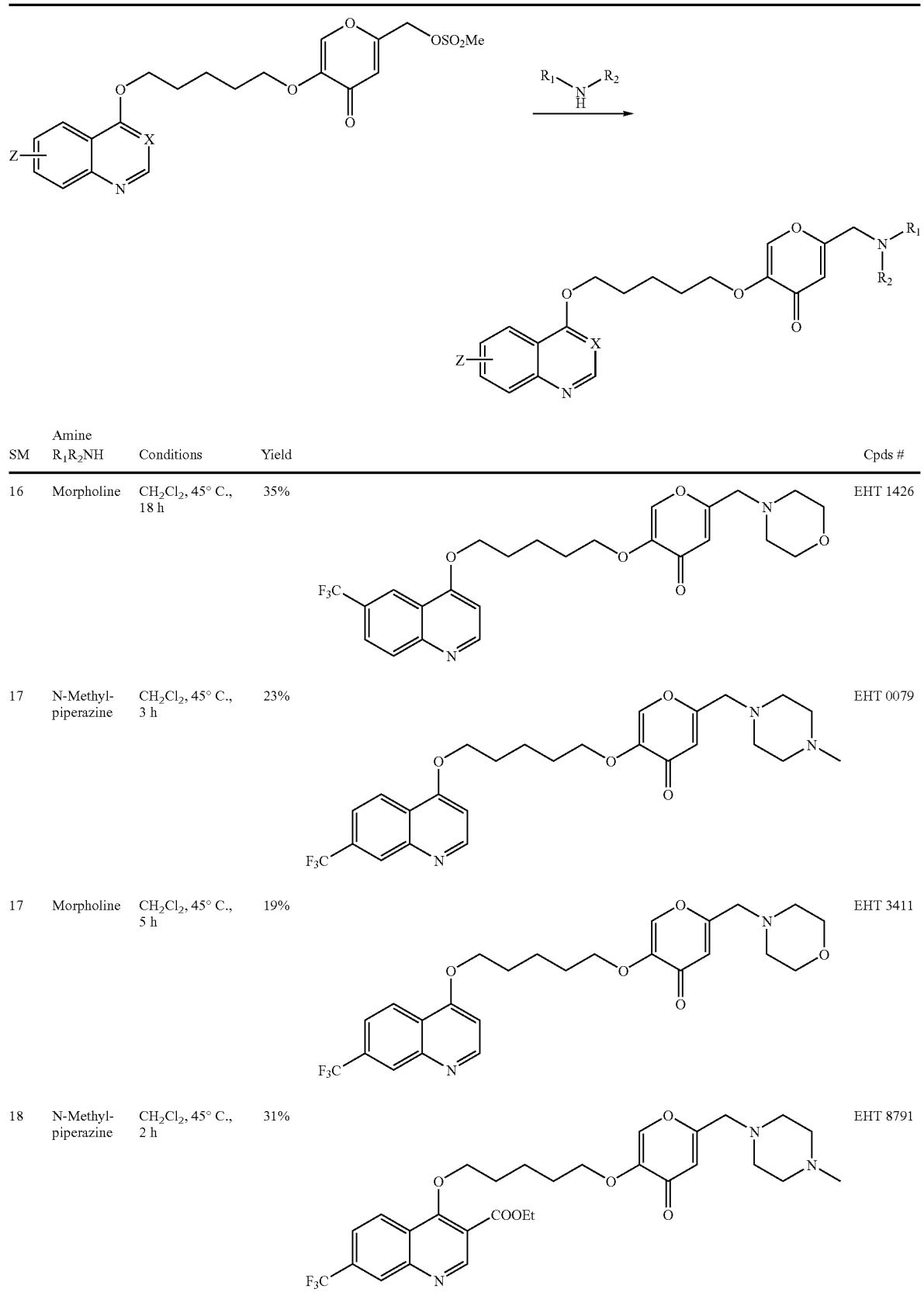
| SM | Amine $R_1R_2NH$ | Conditions | Yield | | Cpds # |
|---|---|---|---|---|---|
| 16 | Morpholine | $CH_2Cl_2$, 45° C., 18 h | 35% | | EHT 1426 |
| 17 | N-Methyl-piperazine | $CH_2Cl_2$, 45° C., 3 h | 23% | | EHT 0079 |
| 17 | Morpholine | $CH_2Cl_2$, 45° C., 5 h | 19% | | EHT 3411 |
| 18 | N-Methyl-piperazine | $CH_2Cl_2$, 45° C., 2 h | 31% | | EHT 8791 |

TABLE 6-continued

| SM | Amine R₁R₂NH | Conditions | Yield | | Cpds # |
|---|---|---|---|---|---|
| 18 | Morpholine | CH₂Cl₂, 45° C., 3 h | 55% | | EHT 8935 |
| 19 | N-Methyl-piperazine | CH₂Cl₂, 45° C., 1 h | 15% | | EHT 5847 |
| 19 | Morpholine | CH₂Cl₂, 45° C., 3 h | 50% | | EHT 4687 |
| 20 | Pyrrolidine | CH₂Cl₂, 45° C., 1.5 h | 35% | | EHT 5317 |

TABLE 6-continued

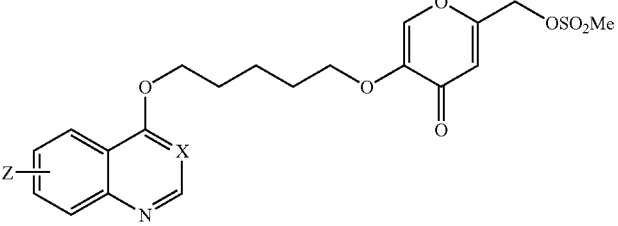

| SM | Amine $R_1R_2NH$ | Conditions | Yield | | Cpds # |
|---|---|---|---|---|---|
| 20 | Morpholine | $CH_2Cl_2$, 45° C., 3 h | 55% | 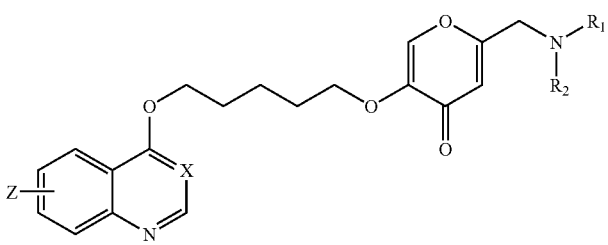 | EHT 3726 |
| 20 | N-Methyl-piperazine | $CH_2Cl_2$, 45° C., 1 h | 35% | 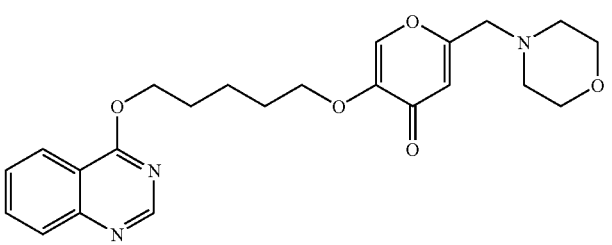 | EHT 4063 |

The last preferred chemical route to obtain the compounds of the invention was a convergent synthesis: reaction between halogenoalkylquinolines (Table 8) and appropriate substituted kojic acids (see their preparation in Table 7) allowed to get the compounds of the invention in better overall yields and by a shorter process.

In table 7 the first reaction is a bromination of kojic acid using the system $H_2SO_4/HBr/H_2O$ at 70° C. for 18 h to obtain the corresponding bromo derivative 21 as described in patent FR2751331. The bromo derivative 21 reacted with different amines (morpholine, N-methylpiperazine or N-Boc-piperazine) to yield to the corresponding substituted kojic acids 22-24.

TABLE 7

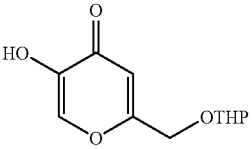

| X | Nucleophile Agent | Conditions | Yield | Cpds nb |
|---|---|---|---|---|
| — | HBr | Step a: H$_2$SO$_4$/HBr, H$_2$O, 70° C., 18 h | 63% | 21 |
|  | 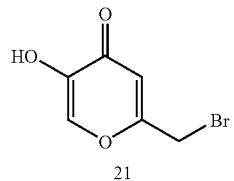 | Step b: CH$_3$CN, 80° C., 3 h | 72% | 22 |
|  | 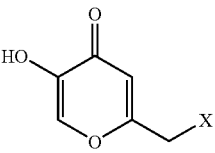 | Step b: THF, 75° C., 2 h | 83% | 23 |
| 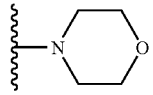 | 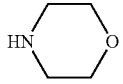 | Step b: TEA, CH$_3$CN, 90° C., 2 h | 78% | 24 |

In table 8, different conditions are used to obtain the various substituted quinolines intermediates 25-33. The alkylating agents reacted with 7-trifluoromethyl-4-quinoline-thiol in the presence of NaH in DMF to afford to 27 and 29 in poor yields (12 and 15%). Alkylation of 7-trifluoromethyl-4-quinoline-thiol was optimized using phase transfer conditions (CHCl$_3$/TBAB/H$_2$O) to yield to 25, 26, 28 and 30 in good yields (61-72%) using as base K$_2$CO$_3$/KOH, Cs$_2$CO$_3$ or no base at all. Intermediate 31 can be prepared from 7-trifluoromethyl-4-quinolinol and 1,2-dichloroethane in phase transfer conditions and fewer elimination product was observed. Derivative 33 can be obtained by alkylation of 7-chloro-4-quinolinol with 1,5-dibromopentane in the presence of Li$_2$CO$_3$ in NMP and major N-alkylated product was observed. Acylation of 4-amino-7-trifluoromethylquinoline in presence of triethylamine and 5-bromovaleryl chloride in CHCl$_3$ led to 32 in excellent yield (90%).

TABLE 8

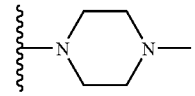

| Z | Y | Alkylating or Acylating Agents | Conditions | Linker—X | Yield | Cpds nb |
|---|---|---|---|---|---|---|
| CF$_3$ | S | 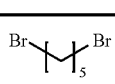 | TBAB, H$_2$O, 20° C., 48 h | 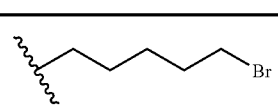 | 72% | 25 |

TABLE 8-continued

| Z | Y | Alkylating or Acylating Agents | Conditions | Linker—X | Yield | Cpds nb |
|---|---|---|---|---|---|---|
| $CF_3$ | S | 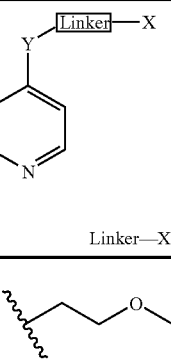 | $Cs_2CO_3$, NaI, TBAB, $CHCl_3/H_2O$, 20° C., 48 h | 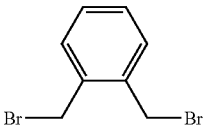 | 65% | 26 |
| $CF_3$ | S | 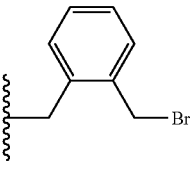 | NaH, DMF, 0 to 20° C., 1.5 h | 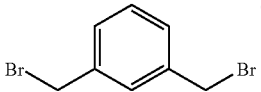 | 12% | 27 |
| $CF_3$ | S | 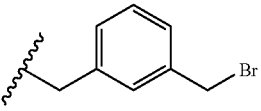 | TBAB, $CHCl_3/H_2O$, 20° C., 15 h |  | 61% | 28 |
| $CF_3$ | S | 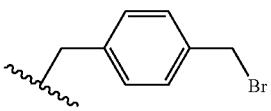 | NaH, DMF, 0 to 20° C., 2.5 h | 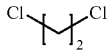 | 15% | 29 |
| $CF_3$ | S | 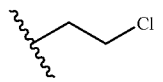 | $K_2CO_3$, KOH, TBAB, $H_2O$, 20° C., 5 h | 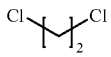 | 67% | 30 |
| $CF_3$ | O | 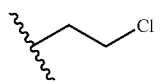 | $K_2CO_3$, KOH, TBAB, $H_2O$, 80° C., 5 h | 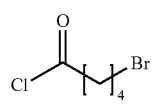 | 25% | 31 |
| $CF_3$ | NH | 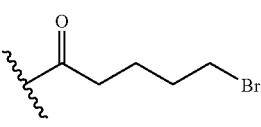 | TEA, $CHCl_3$, 20° C., 15 h | 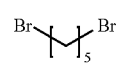 | 90% | 32 |
| Cl | O | 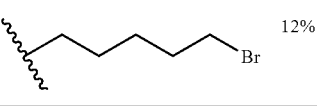 | $Li_2CO_3$, NMP, 90° C., 1 h | | 12% | 33 |

The convergent step (Table 9) was realized using the halogenoalkylquinolines series from table 8 and substituted kojic acids 21-24 from table 7 to obtain the corresponding compounds of the invention.

TABLE 9

| Z | Y | Linker—X | Nucleophile Agent | Conditions | W | Yield | Cpds nb |
|---|---|---|---|---|---|---|---|
| CF₃ | S | ⤳CH₂CH₂Cl | HO-pyranone-CH₂-O-THP | Cs₂CO₃, TBAB, CHCl₃/H₂O, 20° C., 15 h | OTHP | 5% | EHT 5575 |
| CF₃ | O | ⤳CH₂CH₂Cl | 22 | Cs₂CO₃, NaI, DMF, 90° C., 3 h | morpholine | 35% | EHT 6892 |
| CF₃ | S | ⤳(CH₂)₅Br | 22 | Cs₂CO₃, NaI, DMF, 90° C., 2 h | morpholine | 58% | EHT 1864 (2·HCl) |
| CF₃ | S | ⤳CH₂CH₂OCH₂CH₂Cl | 22 | Cs₂CO₃, NaI, DMF, 90° C., 2 h | morpholine | 56% | EHT 0371 |
| CF₃ | NH | ⤳C(O)(CH₂)₃Br | 22 | Cs₂CO₃, DMF, 90° C., 3 h | morpholine | 55% | EHT 6037 |
| CF₃ | S | ⤳CH₂-(1,2-C₆H₄)-CH₂Br | 22 | Cs₂CO₃, DMF, 0 to 20° C., 2 h | morpholine | 64% | EHT 9069 |
| CF₃ | S | ⤳CH₂-(1,3-C₆H₄)-CH₂Br | 22 | Cs₂CO₃, DMF, 0 to 20° C., 4 h | morpholine | 76% / 48% | EHT 2725 / EHT 0434 (2·HCl) |
| CF₃ | S | ⤳CH₂-(1,4-C₆H₄)-CH₂Br | 22 | Cs₂CO₃, DMF, 0 to 20° C., 2 h | morpholine | 46% | EHT 2218 |
| CF₃ | S | ⤳(CH₂)₅Br | 23 | Cs₂CO₃, DMF, 90° C., 3 h | N-Boc piperazine | 75% | EHT 9358 |

TABLE 9-continued

| Z | Y | Linker—X | Nucleophile Agent | Conditions | W | Yield | Cpds nb |
|---|---|---|---|---|---|---|---|
| Cl | O | ~~~~~Br | 23 | $Cs_2CO_3$, DMF, 90° C., 3 h | —N(piperazine)N-Boc | 72% | EHT 2580 |
| $CF_3$ | S | ~~~~~Br | 24 | $Cs_2CO_3$, DMF, 90° C., 2 h | —N(piperazine)N— | 38% | EHT 9241 (3•HCl) |

Most of these final compounds (EHT 6892, EHT 1864, EHT 0371, EHT 6037, EHT 9358, EHT 2580 and EHT 9241) were obtained according to alkylation conditions preferably conducted in DMF at 90° C. using as base $Cs_2CO_3$ and yields are generally comprised between 35 and 75%.

Some of the products bearing an aromatic spacer reacted to lower temperatures (EHT 9069, EHT 2725 and EHT 2218). EHT 5575 was obtained from chloro derivative 30 using phase transfert conditions ($CHCl_3$/TBAB/$H_2O$/$Cs_2CO_3$) in poor yield (5%) and a majority of an elimination product was observed.

The N-Boc-piperazine derivatives (EHT 9358 and EHT 2580) can be deprotected (Table 10) using a solution of HCl gas in ethanol at 50° C. to afford to the corresponding piperazino compounds (EHT 8560 and EHT 0872).

A series of compounds of the invention (EHT 3980, EHT 5743, EHT 0785, EHT 0566, EHT 8366, EHT 3664 and EHT 4495) were prepared (Table 11) starting from the free base of EHT 8560 by reactions with various acyl or carbamyl chloride, mesyl chloride and isocyanate in presence of triethylamine in $CHCl_3$ at 20° C. in good yields (71-98%) (Table 11).

TABLE 10

| Z | Y | Conditions | Yield | Cpds nb |
|---|---|---|---|---|
| Cl | O | Anhydrous HCl, Ethanol, 50° C., 2 h | 50% | EHT 0872 |
| $CF_3$ | S | Anhydrous HCl, Ethanol, 50° C., 3 h | 63% | EHT 8560 |

TABLE 11

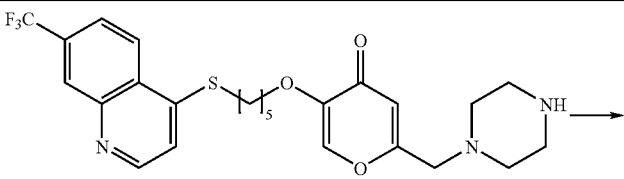

| Reactant | Conditions | R | Yield | Cpds nb |
|---|---|---|---|---|
| Acetyl chloride | TEA, CHCl$_3$, 20° C., 15 h | 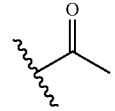 | 90% | EHT 3980 |
| Diethylcarbamyl chloride | TEA, CHCl$_3$, 20° C., 15 h | 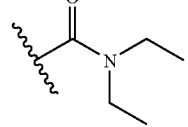 | 98% | EHT 5743 |
| Trimethylacetyl chloride | TEA, CHCl$_3$, 20° C., 15 h | 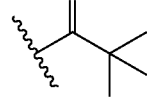 | 56% | EHT 0785 |
| Diisopropylcarbamyl chloride | TEA, CHCl$_3$, 20° C., 15 h | 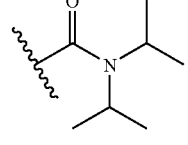 | 63% | EHT 0566 |
| Mesyl chloride | TEA, CHCl$_3$, 20° C., 15 h | 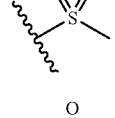 | 45% | EHT 8366 |
| tert-butyl isocyanate | TEA, CHCl$_3$, 20° C., 15 h | 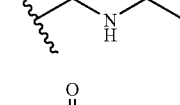 | 71% | EHT 3664 |
| Methylcarbamyl chloride | TEA, CHCl$_3$, 20° C., 15 h | 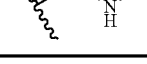 | 59% | EHT 4495 |

It should be understood that other ways of producing these compounds may be designed by the skilled person, based on common general knowledge and following guidance contained in this application.

As indicated above, a further object of this invention relates to a pharmaceutical composition comprising at least one compound of formula (I), as defined above, and a pharmaceutically acceptable vehicle or support.

The compounds may be formulated in various forms, including solid and liquid forms, such as capsules, tablets, gel, solution, syrup, suspension, powder, aerosol, oitment, etc.

The compositions of this invention may contain physiologically acceptable diluents, fillers, lubricants, excipients, solvents, binders, stabilizers, and the like. Diluents that may be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that may be used in the compositions include but are not limited to starch, gelatin and fillers such as sucrose, glucose, dextrose and lactose.

Natural and synthetic gums that may be used in the compositions include but are not limited to sodium alginate, ghatti gum, carboxymethyl cellulose, methyl cellulose, polyvinyl pyrrolidone and veegum. Excipients that may be used in the compositions include but are not limited to microcrystalline cellulose, calcium sulfate, dicalcium phosphate, starch, magnesium stearate, lactose, and sucrose. Stabilizers that may be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that may be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds of formula (I) are administered will vary according to the dosage form, mode of administration, the condition being treated and particulars of the patient being treated. Accordingly, optimal therapeutic concentrations will be best determined at the time and place through routine experimentation.

The compounds according to the invention can also be used enterally. Orally, the compounds according to the invention are suitable administered at the rate of 10 μg to 300 mg per day per kg of body weight. The required dose can be administered in one or more portions. For oral administration, suitable forms are, for example, capsules, tablets, gel, aerosols, pills, dragees, syrups, suspensions, emulsions, solutions, powders and granules; a preferred method of administration consists in using a suitable form containing from 1 mg to about 500 mg of active substance.

The compounds according to the invention can also be administered parenterally in the form of solutions or suspensions for intravenous, subcutaneous or intramuscular perfusions or injections. In that case, the compounds according to the invention are generally administered at the rate of about 10 μg to 10 mg per day per kg of body weight; a preferred method of administration consists of using solutions or suspensions containing approximately from 0.01 mg to 1 mg of active substance per ml.

The compounds according to the invention can also be administered in the eye in the form of solutions or suspensions for intravitreous or retro-orbitary injections. In that case, the compounds according to the invention are generally administered at the rate of about 10 μg to 10 mg per day per kg of body weight; a preferred method of administration consists of using solutions, suspensions or gel containing approximately from 0.01 mg to 1 mg of active substance per ml.

The compounds of formula (I) can be used in a substantially similar manner to other known anti-tumor agents for treating (both chemopreventively and therapeutically) various tumors or to other known agents for treating ocular diseases and especially anti-retinopathic or anti-arthritis agents. For the compounds of this invention, the dose to be administered, whether a single dose, multiple dose, or a daily dose, will of course vary with the particular compound employed because of the varying potency of the compound, the chosen route of administration, the size of the recipient, the type of disease (cancer, and in such a case the type of tumor, arthritis, ocular-diseases and especially retinopathies, and in such a case the type of retinopathy, especially diabetic retinopathy, retinal degenerative diseases, Age-Related Macular Degeneration (ARMD)) and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment or a doctor skilled in the art for ocular-diseases, diabetes or arthritis treatment will be able to ascertain, without undue experimentation, appropriate protocols for the effective administration of the compounds of this present invention, such as by referring to the earlier published studies on compounds found to have anti-tumor, anti-angiogenic and especially anti-retinopathic or anti-arthritis properties.

According to another aspect, the present invention relates to a method for the treatment of a disease associated with abnormal cell proliferation, comprising administering to a patient in need of such treatment an effective amount of at least one compound of general formula (I) as described above.

Preferred compounds for use according to the invention include any sub-group as defined above, and, as specific examples, the following compounds:

2-(Tetrahydro-pyran-2-yloxymethyl)-5-[5-(7-trifluoromethyl-quinolin-4-yloxy)-pentyloxy]-pyran-4-one (EHT 3788)

5-[5-6-Fluoro-2-methyl-quinolin-4-yloxy)-pentyloxy]-2-(tetrahydro-pyran-2-yloxymethyl)-4H-pyran-4-one (EHT 1593)

5-[5-(6-Fluoro-2-trifluoromethyl-quinolin-4-yloxy)-pentyloxy]-2-(tetrahydro-pyran-2-yloxymethyl)-4H-pyran-4-one (EHT 1074)

5-[5-(7-Propyl-quinolin-8-yloxy)-pentyloxy]-2-(tetrahydro-pyran-2-yloxymethyl)-4H-pyran-4-one (EHT 5810)

5-[5-(Benzo[b]thiophen-7-yloxy)-pentyloxy]-2-(tetrahydro-pyran-2-yloxymethyl)-4H-pyran-4-one (EHT 6060)

2-(Tetrahydro-pyran-2-yloxymethyl)-5-[5-(7-trifluoromethyl-quinolin-4-ylsulfanyl)-pentyloxy]-4H-pyran-4-one (EHT 9376)

2-(Tetrahydro-pyran-2-yloxymethyl)-5-[4-(7-trifluoromethyl-quinolin-4-ylsulfanyl)-butoxy]-4H-pyran-4-one (EHT 4745)

2-Tetrahydro-pyran-2-yloxymethyl)-5-[6-(7-trifluoromethyl-quinolin-4-ylsulfanyl)-hexyloxy]-4H-pyran-4-one (EHT 6271)

2-Hydroxymethyl-5-[5-(7-trifluoromethyl-quinolin-4-ylsulfanyl)-pentyloxy]-4H-pyran-4-one hydrochloride salt (EHT 1302)

2-Hydroxymethyl-5-[5-(7-trifluoromethyl-quinolin-4-ylsulfanyl)-pentyloxy]-4H-pyran-4-one (EHT 5909)

2-Methoxymethoxymethyl-5-[5-(7-trifluoromethyl-quinolin-4-ylsulfanyl)-pentyloxy]-4H-pyran-4-one (EHT 2168)

2-Chloromethyl-5-[5-(7-trifluoromethyl-quinolin-4-ylsulfanyl)-pentyloxy]-4H-pyran-4-one (EHT 1494)

2-(4-Methyl-piperazin-1-ylmethyl)-5-[5-(7-trifluoromethyl-quinolin-4-ylsulfanyl)-pentyloxy]-4H-pyran-4-one (EHT 7365)

2-Morpholin-4-ylmethyl-5-[5-(7-trifluoromethyl-quinolin-4-ylsulfanyl)-pentyloxy]-4H-pyran-4-one (EHT 7168)

5-(5-(7-(Trifluoromethyl)quinolin-4-ylthio)pentyloxy)-2-(fluoromethyl)-4H-pyran-4-one (EHT 8817)

5-(5-(7-(Trifluoromethyl)quinolin-4-ylthio)pentyloxy)-2-((piperidin-1-yl)methyl)-4H-pyran-4-one (EHT 9317)

5-(5-(7-(Trifluoromethyl)quinolin-4-ylthio)pentyloxy)-2-(thiomorpholino-methyl)-4H-pyran-4-one (EHT 5430)

2-((Diethylamino)methyl)-5-(5-(7-(trifluoromethyl)quinolin-4-ylthio)pentyloxy)-4H-pyran-4-one (EHT 7370)

5-(5-(Quinazolin-4-yloxy)pentyloxy)-2-(morpholinomethyl)-4H-pyran-4-one (EHT 3726)

5-(5-(Quinazolin-4-yloxy)pentyloxy)-2-((4-methylpiperazin-1-yl)methyl)-4H-pyran-4-one (EHT 4063)

4-[5-(6-Morpholin-4-ylmethyl-4-oxo-4H-pyran-3-yloxy)-pentyloxy]-7-trifluoromethyl-quinoline-3-carboxylic acid ethyl ester (EHT 8935)

5-(5-Quinazolin-4-yloxy)pentyloxy)-2-((pyrrolidin-1-yl)methyl)-4H-pyran-4-one (EHT 5317)

5-(5-(8-(Trifluoromethyl)quinolin-4-yloxy)pentyloxy)-2-((4-methylpiperazin-1-yl)methyl)-4H-pyran-4-one (EHT 5847)

5-(5-(8-(Trifluoromethyl)quinolin-4-yloxy)pentyloxy)-2-(morpholinomethyl)-4H-pyran-4-one (EHT 4687)

5-(5-(7-(Trifluoromethyl)quinolin-4-yloxy)pentyloxy)-2-(morpholinomethyl)-4H-pyran-4-one (EHT 3411)

5-(5-(7-(Trifluoromethyl)quinolin-4-yloxy)pentyloxy)-2-((4-methylpiperazin-1-yl)methyl)-4H-pyran-4-one (EHT 0079)

5-(5-(6-(Trifluoromethyl)quinolin-4-yloxy)pentyloxy)-2-(morpholinomethyl)-4H-pyran-4-one (EHT 1426)

4-[5-(6-(4-Methyl-piperazin-1-ylmethyl)-4-oxo-4H-pyran-3-yloxy)-pentyloxy]-7-trifluoromethyl-quinoline-3-carboxylic acid ethyl ester (EHT 8791)

4-[5-(6-(4-Methyl-piperazin-1-ylmethyl)-4-oxo-4H-pyran-3-yloxy)-pentyloxy]-7-trifluoromethyl-quinoline-3-carboxylic acid ethyl ester (EHT 2725)

5-((4-((7-(Trifluoromethyl)quinolin-4-ylthio)methyl)phenyl)methoxy)-2-(morpholinomethyl)-4H-pyran-4-one (EHT 2218)

5-((2-((7-(Trifluoromethyl)quinolin-4-ylthio)methyl)phenyl)methoxy)-2-(morpholinomethyl)-4H-pyran-4-one (EHT 9069)

5-(5-(7-(Trifluoromethyl)quinolin-4-ylthio)pentyloxy)-2-((4-acetylpiperazin-1-yl)methyl)-4H-pyran-4-one (EHT 3980)

4-((5-(5-(7-(Trifluoromethyl)quinolin-4-ylthio)pentyloxy)-4-oxo-4H-pyran-2-yl)methyl)-N,N-diethylpiperazine-1-carboxamide (EHT 5743)

5-(5-(7-(Trifluoromethyl)quinolin-4-ylthio)pentyloxy)-2-((4-(pivaloyl)piperazin-1-yl)methyl)-4H-pyran-4-one (EHT 0785)

4-((5-(5-(7-(Trifluoromethyl)quinolin-4-ylthio)pentyloxy)-4-oxo-4H-pyran-2-yl)methyl)-N,N-di-isopropylpiperazine-1-carboxamide (EHT 0566)

5-(5-(7-(Trifluoromethyl)quinolin-4-ylthio)pentyloxy)-2-((4-methylsulfonylpiperazin-1-yl)methyl)-4H-pyran-4-one (EHT 8366)

4-((5-(5-(7-(Trifluoromethyl)quinolin-4-ylthio)pentyloxy)-4-oxo-4H-pyran-2-yl)methyl)-N-tert-butylpiperazine-1-carboxamide (EHT 3664)

4-((5-(5-(7-(Trifluoromethyl)quinolin-4-ylthio)pentyloxy)-4-oxo-4H-pyran-2-yl)methyl)-N-methylpiperazine-1-carboxamide (EHT 4495)

5-(6-(Morpholinomethyl)-4-oxo-4H-pyran-3-yloxy)-N-(7-trifluoromethyl)quinolin-4-yl)pentanamide (EHT 6037)

5-(2-(2-(7-(Trifluoromethyl)quinolin-4-ylthio)ethoxy)ethoxy)-2-(morpholinomethyl)-4H-pyran-4-one (EHT 0371)

5-(5-(7-(Trifluoromethyl)quinolin-4-ylthio)pentyloxy)-2-(morpholinomethyl)-4H-pyran-4-one dihydrochloride (EHT 1864)

5-((3-((7-(Trifluoromethyl)quinolin-4-ylthio)methyl)phenyl)methoxy)-2-(morpholinomethyl)-4H-pyran-4-one dihydrochloride (EHT 0434)

tert-Butyl 4-((5-(5-(7-(trifluoromethyl)quinolin-4-ylthio)pentyloxy)-4-oxo-4H-pyran-2-yl)methyl)piperazine-1-carboxylate (EHT 9358)

tert-Butyl 4-((5-(5-(7-chloroquinolin-4-yloxy)pentyloxy)-4-oxo-4H-pyran-2-yl)methyl)piperazine-1-carboxylate (EHT 2580)

5-(5-(7-(Trifluoromethyl)quinolin-4-ylthio)pentyloxy)-2-((4-methylpiperazin-1-yl)methyl)-4H-pyran-4-one trihydrochloride (EHT 9241)

5-(5-(7-(Trifluoromethyl)quinolin-4-ylthio)pentyloxy)-2-((piperazin-1-yl)methyl)-4H-pyran-4-one trihydrochloride (EHT 8560)

5-(5-(7-Chloroquinolin-4-yloxy)pentyloxy)-2-((piperazin-1-yl)methyl)-4H-pyran-4-one (EHT 0872)

5-(2-(7-(Trifluoromethyl)quinolin-4-ylthio)ethoxy)-2-((tetrahydro-2H-pyran-2-yloxy)methyl)-4H-pyran-4-one (EHT 5575)

5-(8-(7-(Trifluoromethyl)quinolin-4-ylthio)octyloxy)-2-((tetrahydro-2H-pyran-2-yloxy)methyl)-4H-pyran-4-one (EHT 1006)

5-(7-(7-(Trifluoromethyl)quinolin-4-ylthio)heptyloxy)-2-((tetrahydro-2H-pyran-2-yloxy)methyl)-4H-pyran-4-one (EHT 8883)

5-(2-(7-(Trifluoromethyl)quinolin-4-yloxy)ethoxy)-2-(morpholinomethyl)-4H-pyran-4-one (EHT 6892).

A further object of this invention is the use of an effective amount of at least one compound of formula (I) as defined above for the preparation of pharmaceutical composition for the treatment of a disease associated with abnormal cell proliferation and of a disease associated with unregulated angiogenesis.

Because of their cell proliferation inhibitory activity, the compounds of this invention are suitable for treating a variety of diseases in a variety of conditions. In this regard, "treatment" or "treating" includes both therapeutic and prophylactic treatments. Accordingly, the compounds may be used at very early stages of a disease, or before early onset, or after significant progression, including metastasis. The term "treatment" or "treating" designates in particular a reduction of the burden in a patient, such as a reduction in cell proliferation rate, a destruction of diseased proliferative cells, an inhibition of the formation of vessel or vessel-like structure, a reduction of tumor mass or tumor size, a delaying of tumor progression, as well as a complete tumor suppression.

Typical examples of diseases associated with abnormal cell proliferation and/or with unregulated angiogenesis include cancers, restenosis, arthritis, diabetes, ocular-diseases and especially retinopathies, for instance. The compounds of this invention are particularly suited for the treatment of cancers, such as solid tumors or lymphoid tumors. Specific examples include prostate cancer, ovarian cancer, pancreas cancer, lung cancer, breast cancer, liver cancer, head and neck cancer, colon cancer, bladder cancer, non-Hodgkin's lymphoma cancer, leukemia (acute lymphoblastic leukemia, chronic myeloid leukemia, acute myeloid leukemia) and melanoma.

The compounds may be administered according to various routes, typically by oral route or by injection, such as local or systemic injection(s). Intratumoral injections are preferred for treating existing cancers. However, other administration routes may be used as well, such as intramuscular, intravenous, intradermic, subcutaneous, etc. Furthermore, repeated injections may be performed, if needed, although it is believed that limited number of injections will be needed in view of the efficacy of the compounds.

A further object of this invention is a composition for reducing cancer cell proliferation by administering in a subject having cancer an effective amount of compound of formula (I) as defined above.

A further object of this invention is a composition for treating metastatic cancers by administering in a subject in need of such treatment an effective amount of compound of formula (I) as defined above.

A further object of this invention is a composition for treating an eye-disease by administering in a subject in need of such treatment an effective amount of compound of formula (I) as defined above.

A further object of this invention is a composition for treating arthritis by administering in a subject in need of such treatment an effective amount of compound of formula (I) as defined above.

A further object of this invention is the use of a compound as defined above for the preparation of a pharmaceutical composition for treating metastatic cancers or for reducing cancer cell proliferation.

A further object of this invention is the use of a compound as defined above for the preparation of a pharmaceutical composition for treating an ocular-disease, especially retinopathies (including diabetic retinopathies, retinal degenerative diseases and Age-Related Macular Degeneration (ARMD)).

A further object of this invention is the use of a compound as defined above for the preparation of a pharmaceutical composition for treating arthritis.

Further aspects and advantages of this invention will be disclosed in the following examples, which should be regarded as illustrative and not limiting the scope of this application.

LEGEND TO THE TABLES AND FIGURES

Table 12: 6-day cell viability assay (MTT) in the presence of 10% Fetal Bovine Serum and 1% DMSO, in HMEC1, HCT116, MDA-MB-231, MCF7 and NIH3T3 cell lines. $3\ 10^3$ to $15\ 10^3$ cells were seeded in 48-well plates in growth medium containing 10% FBS, with or without various concentrations of test compounds. Cell cultures were fed every 3 days with the appropriate media. Cell viability was determined on day 6. Data were analyzed and IC50s were calculated from dose-response curves using GraphPad Prism. Results summarized in the tables are mean±SEM of 1 to 8 independent experiments.

Table 13: 6-day cell viability assay (MTT) in the presence of 0.5% Fetal Bovine Serum and 1% DMSO, in HCT116 and MDA-MB-231 cell lines. $7.5\ 10^4$ to $15\ 10^4$ cells were seeded in 48-well plates in growth medium containing 10% FBS, with or without various concentrations of test compounds. Cell cultures were fed every 3 days with the appropriate media. Cell viability was determined on day 6. Data were analyzed and IC50s were calculated from dose-response curves using GraphPad Prism. Results summarized in the tables are mean±SEM of 1 to 2 independent experiments.

Table 14: 3-day cell viability assay (MTT) in the presence of 10% Fetal Bovine Serum and 1% DMSO, in DLD1, HCT116, MDA-MB-231, MCF7 and HeLa cells. $7.5\ 10^3$ to $1.5\ 10^4$ cells were seeded in 48-well plates in growth medium containing 10% FBS, with or without various concentrations of test compounds. Data were analyzed and IC50s were calculated from dose-response curves using GraphPad Prism. Results summarized in the tables are mean±SEM of 1 to 7 independent experiments.

Table 15: 16-hour cell viability assay (MTT) in the presence of 10% Fetal Bovine Serum and 1% DMSO, in HCT116, MDA-MB-231, NIH3T3, HepG2 and primary hepatocytes. $5\ 10^4$ to $10\ 10^4$ cells were seeded in 48-well plates in growth medium containing 10% FBS, with or without various concentrations of test compounds. Data were analyzed and IC50s were calculated from dose-reponse curves using GraphPad Prism. Results summarized in the tables are mean±SEM of 1 to 2 independent experiments.

FIG. 1: Study of compounds effect on the actin cytoskeleton. Quiescent Swiss 3T3 cells were treated for 30 minutes with various concentrations of the compounds and were then submitted to osmotic shock by 10 min. incubation in a medium containing 50% $H_2O$. Cells were subsequently fixed, permeabilized and labeled with Phalloidin TRITC. 100 to 200 cells were counted under a microscope, and the percentage of cells displaying lamellipodia and ruffles was evaluated.

Figure 2:
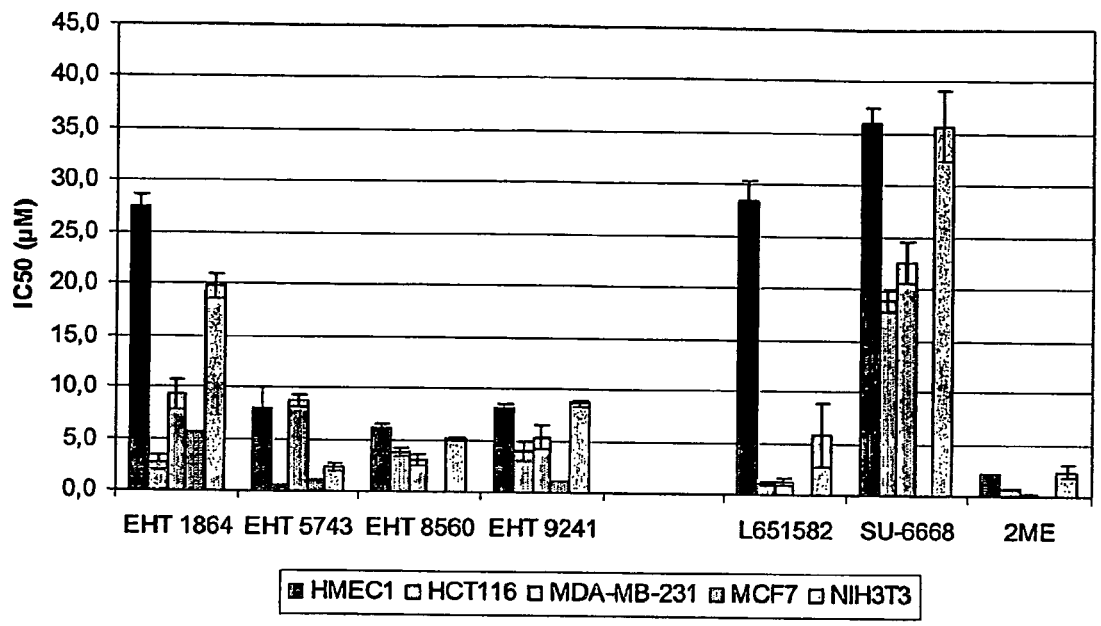
Figure 2:
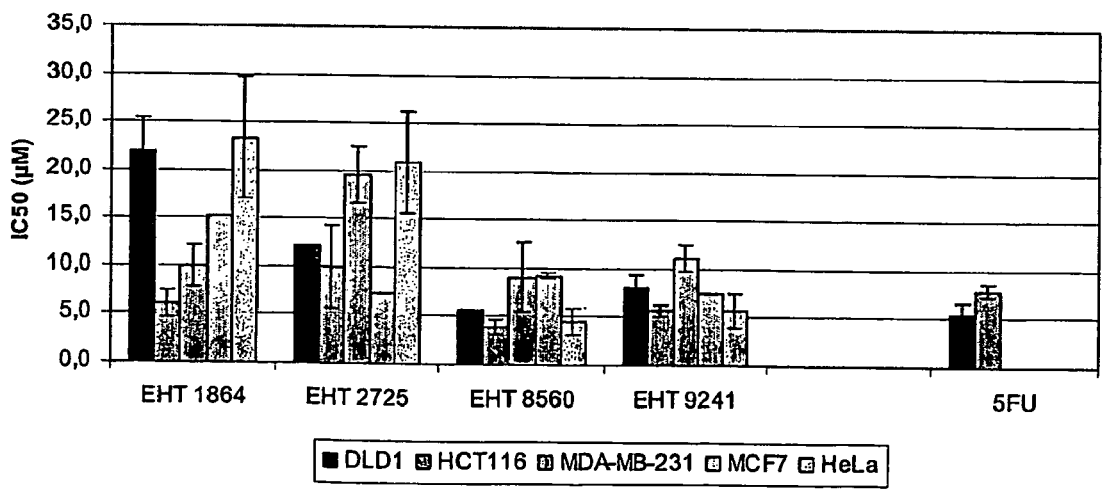

FIG. 2: MTT assays for best compounds after 6-(A) and 3-(B) day treatments. Cells were seeded in 48-well plates In growth medium containing 10% FBS, with or without various concentrations of test compounds. Cell cultures were fed every 3 days with the appropriate media. Cell viability was determined on days 3 or 6. Data were analyzed and IC50s were calculated from dose-reponse curves using GraphPad Prism. Data are mean±SEM of 1 to 8 independent experiments.

Figure 3:
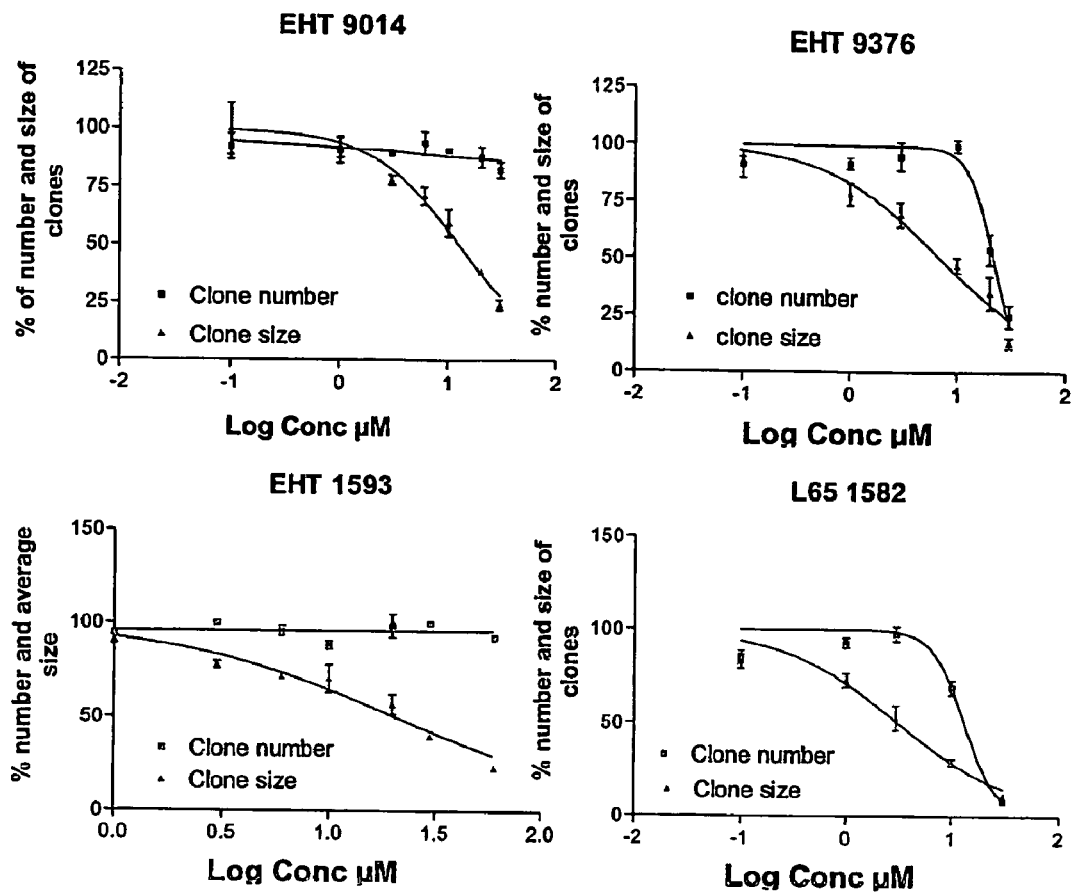
Figure 3:
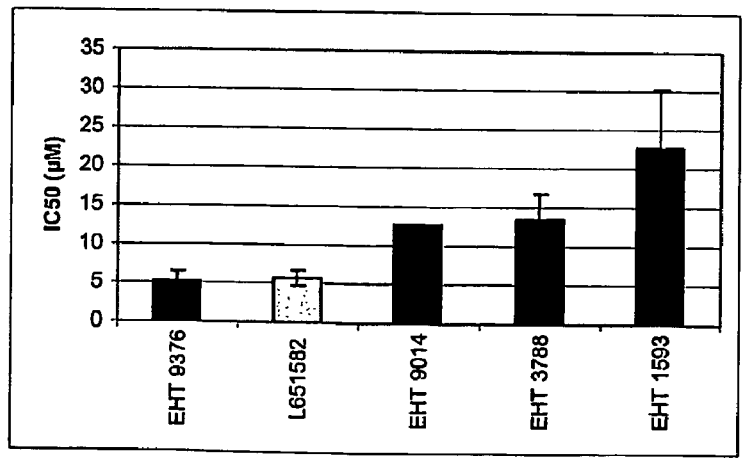

FIG. 3: Anchorage-independent growth assay in soft agar. $5\ 10^3$ cells were seeded in 24-well plates in 0.3% agar-containing medium supplemented with the designated amount of compounds. After 7 days of incubation at 37° C., pictures of each well were taken and analyzed using the ImageJ image analysis software. In particular, clone size and number were calculated. The data were analyzed using GraphPad Prism, and IC50 was calculated. Results displayed on the graph are mean±SEM of 1 to 3 experiments. (A) Typical dose-response curves obtained for clone size and number. (B) Bar graph displaying the IC50s calculated for each compound.

Figure 4:
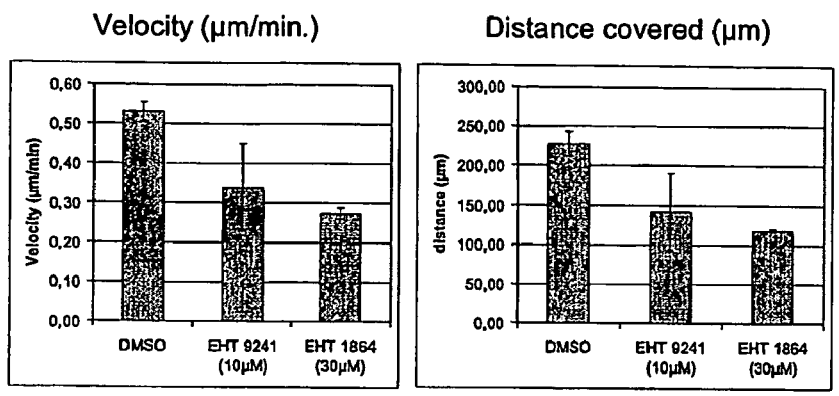
Figure 4:
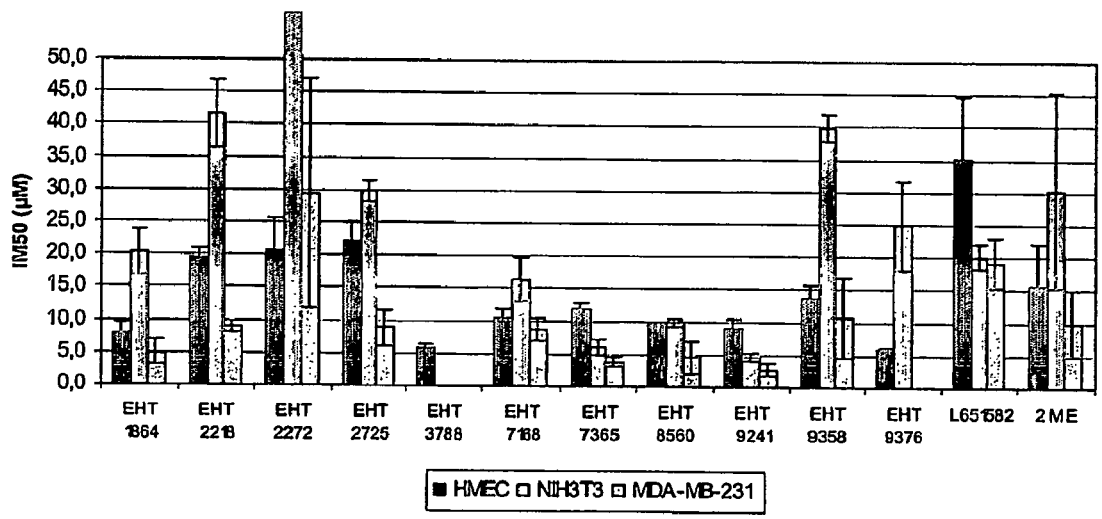

FIG. 4: Migration assays. (A) Wound healing assay in REF cells. $7.6\ 10^4$ cells were plated on coverslips 48 hours before the experiment. The cells were pre-treated for 30 min. with the compounds, and then a scrape was done using a pipette tip. The scraped coverslips in treatment medium were put under a thermostated microscope coupled to a video camera. Movies were analyzed as described in material and methods, and velocity and total distance covered by the cells were evaluated. Bar graphs represent the mean±SEM of 2 to 4 experiments. (B) Boyden chamber migration assay in HMEC1, NIH3T3 and MDA-MB-231 cells. $5\ 10^4$ to $7.5\ 10^4$ Cells, resuspended in culture medium with or without FBS and with different compound concentrations, were seeded in the upper Boyden blind well on top of 8 μm pore-sized filters. The ability of the cells to migrate through the filter was assayed in the absence or presence of FBS in the lower Boyden chamber. After 16 hours incubation, the medium was removed and replaced with calcein-AM containing medium. After labeling, cells were washed with HBSS and fluorescence was read in a fluorescence plate reader. Fluorescence values were normalized against the fluorescence obtained for the 1% DMSO control. The data plotted are the means±SEM of 2 to 4 independent experiments.

Figure 5:
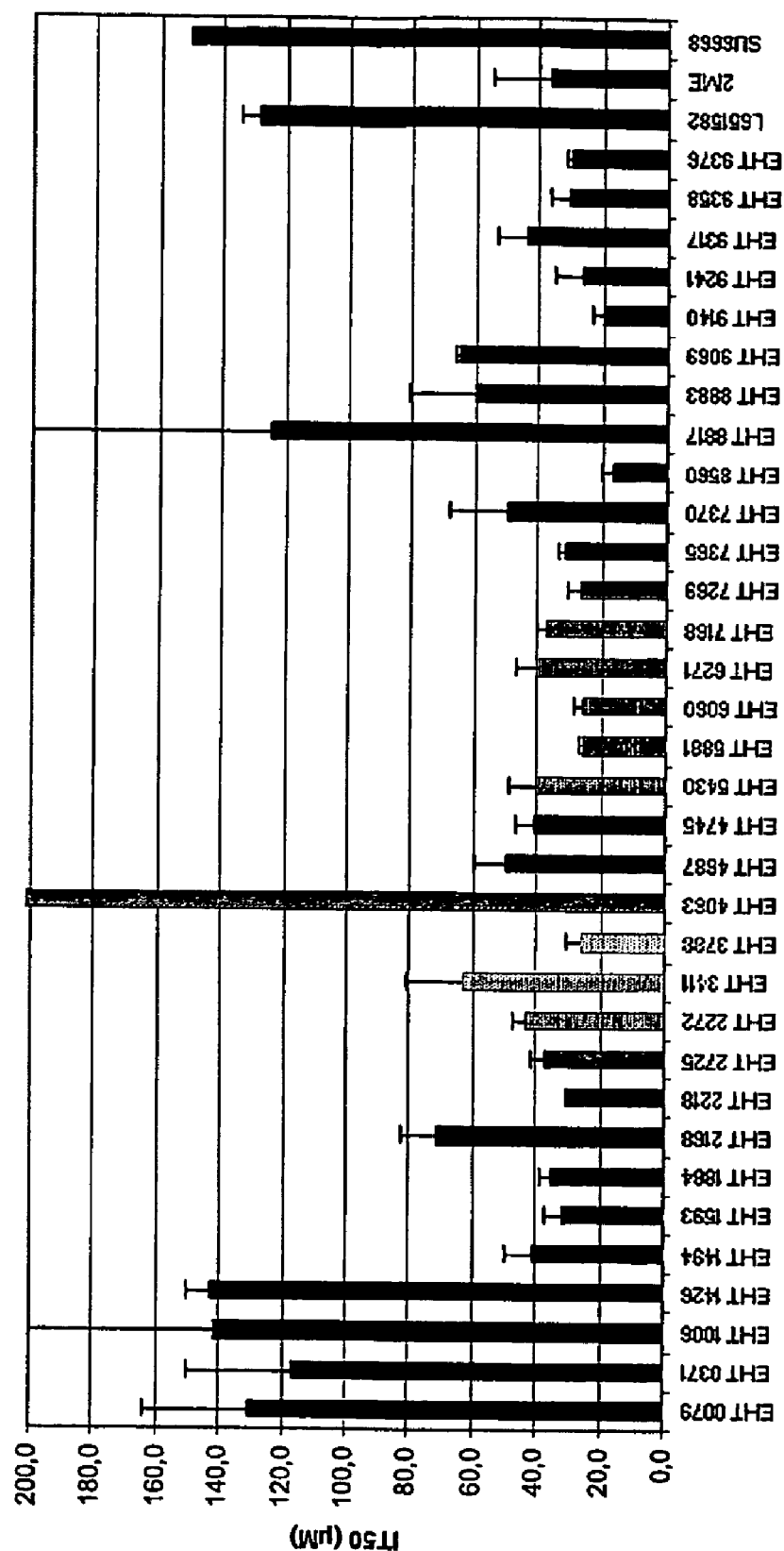

FIG. 5: Tubulogenesis assay (number of junctions). $2\ 10^4$ Cells were plated on Matrigel-coated wells as described in the material and methods. Pictures of each well were taken after a 7-hours incubation. The "number of junctions" parameter was quantitated using the AngioSys software and data were analyzed using GraphPad Prism for IT50 calculation. Values represent the mean±SEM of 2 to 30 independent experiments.

Figure 6:
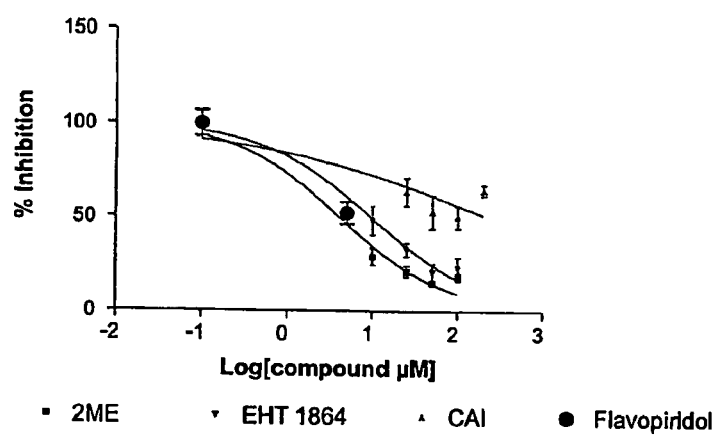

FIG. 6: In vivo zebrafish angiogenesis assay. 20 Hours post fertilization (hpf) embryos Were incubated with compounds and 1% DMSO for 28 hours. Vessels were stained with NBT/BCIP and morphometric analyses were done using the Adobe Photoshop software. For each condition, 10 embryos were analyzed and results were expressed as means±SEM. (A) dose response curves. (B) table presenting the 50% and max inhibition of intersegmental vessels formation together with the percentage of dead embryos (see material and methods).

EXAMPLES

Examples 1 to 50 disclose the synthesis and physicochemical properties of compounds according to this invention.

Example 51 discloses the biological activity of the compounds.

General $^1$H NMR spectra were recorded at ambient temperature with an Avance 300 (Bruker) spectrometer. The compounds were analyzed by reverse phase high performance liquid chromatography (HPLC) using a Waters Autopurification System equipped with a Waters 2525 Pump, a Waters 2696 photodiode array detector, and a XTerra column (Part. No. 186000482, 5 μm, C18, 4.5×50 mm). The HPLC method used was a gradient of 5% solvent B to 100% in 7 min. Solvent A was $H_2O$ with 0.05% TFA and solvent B was $CH_3CN$ with 0.05% TFA (Method A). Melting points were measured with a Büchi B-545 melting point apparatus and are uncorrected. To isolate reaction products the solvent were removed by evaporation using a vacuum rotatory evaporator, the water bath temperature not exceeding 40° C.

Preparation of EHT 3788, 1593, EHT 1074, EHT 5810, EHT 0470, EHT 6060 and EHT 9376

General Procedures

Method A (in THF):

In a 25 mL round-bottom flask equipped with a magnetic stirrer and under an inert atmosphere were charged successively one equivalent of NaH (60% in mineral oil), anhydrous THF (10 mL) and the monomer to be deprotonated (250 mg). The reaction mixture was abandoned until no evolution of gas was observed (between 3 and 5 hours). A solution 1 M of 5-(5-bromo-pentyloxy)-2-(tetrahydro-pyran-2-yloxymethyl)-4H-pyran-4-one 1 in THF (1 eq) was added and the reaction mixture was stirred 12 h at room temperature. The reaction mixture is evaporated in vacuo, the crude product is purified by a wash with a solution of aqueous NaOH 2N and/or by flaschromatography on silica.

Method B (in DMSO):

In a 50 mL round-bottom flask equipped with a magnetic stirrer and under an inert atmosphere were charged successively one equivalent of NaH (60% in mineral oil), DMSO (5 mL) and the monomer to be deprotonated (250 mg). The reaction mixture was heated at 60° C. for 3 hours. After cooling to room temperature, the 5-(5-bromo-pentyloxy)-2-(tetrahydro-pyran-2-yloxymethyl)-4H-pyran-4-one 1 (1 eq) was added (in one time) and the reaction mixture was heated at 60° C. for 12 h. After cooling, 50 mL of dichloromethane was added, the organic layer is washed with $H_2O$ (4×10 mL), dried over $MgSO_4$, filtered and evaporated in vacuo. The crude product is purified by a wash with a solution of aqueous NaOH 2N and/or by flaschromatography on silica.

5-(5-Bromo-pentyloxy)-2-(tetrahydro-pyran-2-yloxymethyl)-4H-pyran-4-one 1

The compound was prepared according to example 11 using 5-hydroxy-2-(tetrahydro-pyran-2-yloxymethyl)-4H-pyran-4-one (3.5 g, 15.5 mmol) in 20 mL of DMF, $Cs_2CO_3$ (5.04 g, 15.5 mmol) and 1,5-dibromopentane (8.8 g, 36.7 mmol). The sealed tube was heated at 90-95° C. for 1 h 40. A white solid 1 was obtained (5.30 g, 91% yield).

The structure of compound 1 is presented below:

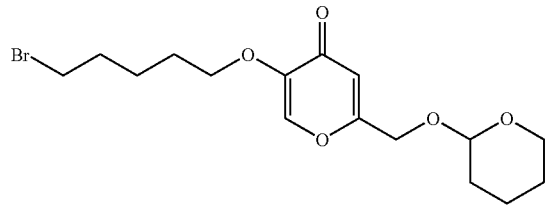

MW: 375.25; Yield: 91%; Yellow solid; Mp: 140.3° C. $R_f$: 0.36 ($CH_2Cl_2$:EtOAc=8:2). $^1$H-NMR ($CDCl_3$, δ): 1.53-1.84 (m, 12H, 6×$CH_2$), 3.52-3.57 (m, 1H, $OCH_2$), 3.77-3.84 (m, 1H, O—$CH_2$), 4.30 (d, $J_{BA}$=14.5 Hz, 1H, $OCH_2$), 4.48 (s, 2H, $OCH_2$), 4.50 (d, $J_{AB}$=14.5 Hz, 1H, $OCH_2$), 4.70 (t, J=3.1 Hz, 1H, OCHO), 5.07 (s, 2H, $BrCH_2$), 6.51 (s, 1H, —C═CH—), 7.36-7.42 (m, 4H, Ar—H), 7.53 (s, 1H, —C═CH—). MS-ESI m/z (rel. Int.): 374.9-376.9 ([MH]$^+$, 100). HPLC: Method A, Detection UV 254 nm, RT=5.73 min.

Example 1

2-(Tetrahydro-pyran-2-yloxymethyl)-5-[5-(7-trifluoromethyl-quinolin-4-yloxy)-pentyloxy]-pyran-4-one (EHT 3788)

The compound was prepared according to method A with 7-trifluoromethyl-quinolin-4-ol (0.25 g, 0.12 mmol). After purification by chromatography on silica using as eluent $CH_2Cl_2$:MeOH=95:5 a beige solid EHT 3788 (0.11 g, 18% yield) was obtained.

The structure of compound ex 1 is presented below:

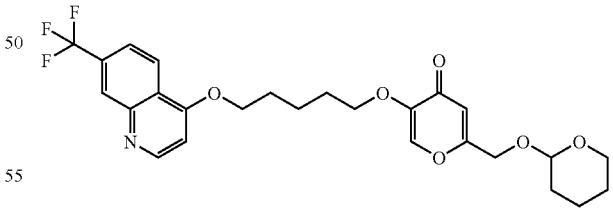

MW: 507.50; Yield 18%; beige solid. $^1$H-NMR ($CDCl_3$, δ): 1.50-2.12 (m, 12H, 6×$CH_2$), 3.50-3.58 (m, 1H, $CH_2CH_2O$), 3.75-3.85 (m, 1H, $CH_2CH_2O$), 3.96 (t, J=7.0 Hz, 2H, $OCH_2$), 4.27 (t, J=7.0 Hz, 2H, $OCH_2$), 4.34 (dd, $J_{BA}$=14.4 Hz, J=0.6 Hz, 1H, $CH_2O$), 4.52 (dd, $J_{AB}$=14.4 Hz, J=0.6 Hz, 1H, $CH_2O$), 4.73 (m, 1H, OCHO), 6.52 (d, J=0.6 Hz, 1H, —C═CH—), 6.83 (d, J=5.7 Hz, 1H, Ar—H), 7.59 (s, 1H, —C═CH—), 7.68 (d, J=9.6 Hz, 1H, Ar—H), 8.34 (m, 1H, Ar—H), 8.83 (dd, J=6.3 Hz, J=5.6 Hz, 1H, Ar—H).

Example 2

5-[5-(6-Fluoro-2-methyl-quinolin-4-yloxy)-pentyloxy]-2-(tetrahydro-pyran-2-yloxymethyl)-4H-pyran-4-one (EHT 1593)

The compound was prepared according to example 11 with 6-fluoro-2-methyl-quinolin-4-ol (0.25 g, 1.41 mmol). After purification by chromatography on silica using as eluent heptane:EtOAc=9:1 a brown oil EHT 1593 (0.13 g, 19.5% yield) was obtained.

The structure of compound ex 2 is presented below:

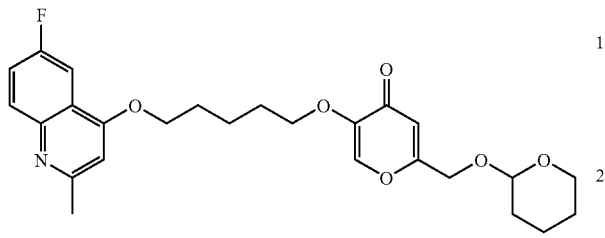

MW: 471.52; Yield 19.5%; Brown oil. $^1$H-NMR (CDCl$_3$, δ): 1.50-2.02 (m, 12H, 6×CH$_2$), 2.69 (s, 3H, CH$_3$), 3.50-3.58 (m, 1H, CH$_2$CH$_2$O), 3.75-3.85 (m, 1H, CH$_2$CH$_2$O), 3.68 (t, J=6.3 Hz, 2H, OCH$_2$), 4.21 (t, J=6.3 Hz, 2H, OCH$_2$), 4.34 (dd, J$_{BA}$=14.4 Hz, J=0.6 Hz, 1H, CH$_2$O), 4.53 (dd, J$_{AB}$=14.4 Hz, J=0.6 Hz, 1H, CH$_2$O), 5.32 (m, 1H, OCHO), 6.52 (s, 1H, —C=CH—), 6.63 (s, 1H, Ar—H), 7.38-7.46 (m, 1H, Ar—H), 7.60 (s, 1H, —C=CH—), 7.74 (dd, J=6.3 Hz, J=2.7 Hz, 1H, Ar—H), 7.93 (dd, J=6.3 Hz, J=5.1 Hz, 1H, Ar—H). MS-ESI m/z (rel. Int.): 472.1 ([MH]$^+$, 90), 388.0 (15), 295.1 (100), 227.0 (15), 211.1 (10), 178.0 (45). HPLC: Method A, detection UV 254 nm, EHT 1593 RT=4.62 min, peak area 95.7%

Example 3

5-[5(6-Fluoro-2-trifluoromethyl-quinolin-4-yloxy)-pentyloxy]-2-(tetrahydro-pyran-2-yloxymethyl)-4H-pyran-4-one (EHT 1074)

The compound was prepared according to method B with 6-fluoro-2-trifluoromethyl-quinolin-4-ol (0.25 g, 1.08 mmol). After purification by chromatography on silica using as eluent CH$_2$Cl$_2$:MeOH=98:2 a grey solid EHT 1074 (0.07 g, 12% yield) was obtained.

The structure of compound ex 3 is presented below:

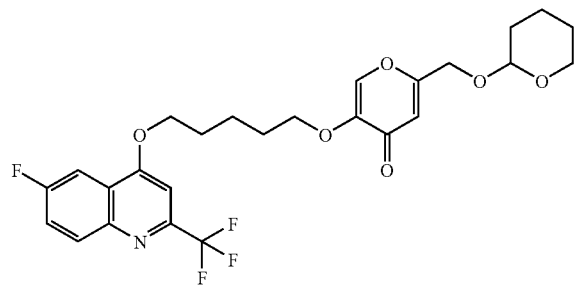

MW: 525.49; Yield: 12%; Grey solid. $^1$H-NMR (CD$_3$Cl, δ): 1.50-1.92 (m, 8H, 4×CH$_2$), 1.92-2.12 (m, 4H, 2×CH$_2$), 3.52-3.59 (m, 1H, CH$_2$O), 3.83-3.90 (m, 1H, CH$_2$O), 3.97 (t, J=6.3 Hz, 2H, OCH$_2$), 4.32 (t, J=5.7 Hz, 2H, OCH$_2$), 4.34 (dd, J$_{BA}$=14.4 Hz, J=0.6 Hz, 1H, =CCH$_2$O), 4.53 (dd, J$_{AB}$=14.4 Hz, J=0.6 Hz, 1H, =CCH$_2$O), 4.72 (t, J=3.0 Hz, 1H, OCH$_2$O), 6.52 (d, J=0.6 Hz, 1H, —CH=), 7.06 (s, 1H, Ar—H), 7.56 (m, 1H, Ar—H), 7.61 (s, 1H, —CH=), 7.85 (dd, J=9.3 Hz, J=3.0 Hz, 1H, Ar—H), 8.16 (dd, J=9.3 Hz, J=5.1 Hz, 1H, Ar—H).

Example 4

5-[5-(7-Propyl-quinolin-8-yloxy)-pentyloxy]-2-(tetrahydro-pyran-2-yloxymethyl)-4H-pyran-4-one (EHT 5810)

The compound was prepared according to method B with 7-propyl-quinolin-8-ol (0.25 g, 1.33 mmol). After purification by chromatography on silica using as eluent CH$_2$Cl$_2$:MeOH=98:2 a green oil EHT 5810 (0.16 g, 25% yield) was obtained.

The structure of compound ex 4 is presented below:

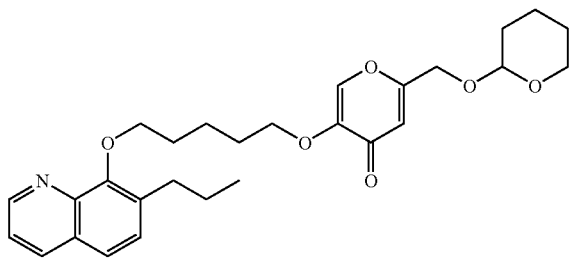

MW: 481.58; Yield: 25%; Green oil. $^1$H-NMR (CD$_3$Cl, δ): 1.00 (t, J=7.2 Hz, 3H, Me), 1.50-1.92 (m, 10H, 5×CH$_2$), 1.92-2.10 (m, 4H, 2×CH$_2$), 2.84 (t, J=7.2 Hz, 2H, =C—CH$_2$CH$_2$CH$_3$), 3.52-3.59 (m, 1H, CH$_2$O), 3.83-3.90 (m, 1H, CH$_2$O), 3.94 (t, J=6.6 Hz, 2H, OCH$_2$O), 4.32 (t, J=6.6 Hz, 2H, OCH$_2$), 4.34 (dd, J$_{BA}$=14.4 Hz, J=0.6 Hz, 1H, =CCH$_2$O), 4.52 (dd, J$_{AB}$=14.4 Hz, J=0.6 Hz, 1H, =CCH$_2$O), 4.73 (t, J=3.0 Hz, 1H, OCH$_2$O), 6.52 (d, J=0.6 Hz, 1H, —C=CH—), 7.33 (dd, J=8.1 Hz, J=4.2 Hz, 1H, Ar—H), 7.38 (d, J$_{BA}$=8.4 Hz, 1H, Ar—H), 7.50 (d, J$_{BA}$=8.4 Hz, 1H, Ar—H), 7.59 (s, 1H, —C=CH—), 8.09 (d, J=1.8 Hz, 1H, Ar—H), 8.16 (dd, J=4.2 Hz, J=1.8 Hz, 1H, Ar—H).

Example 5

5-[5-(Benzo[b]thiophen-7-yloxy)-pentyloxy]-2-(tetrahydro-pyran-2-yloxymethyl)-4H-pyran-4-one (EHT 6060)

The compound was prepared according to method A with benzo[b]thiophen-7-ol (0.25 g, 1.66 mmol). After purification by chromatography on silica using as eluent CH$_2$Cl$_2$:MeOH=95:5 a yellow oil EHT 6060 (0.02 g, 3% yield) was obtained.

The structure of compound ex 5 is presented below:

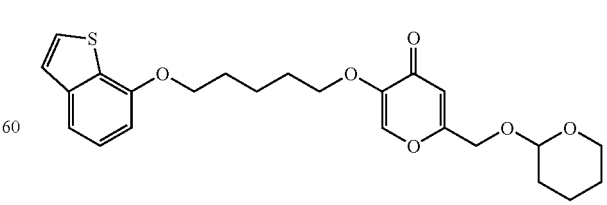

MW: 444.54; Yield: 3%; Yellow oil. $^1$H-NMR (CDCl$_3$, δ): 1.50-2.00 (m, 12H, 6×CH$_2$), 3.52-3.60 (m, 1H, CH$_2$CH$_2$O), 3.82-3.90 (m, 1H, CH$_2$CH$_2$O), 3.94 (t, 2H, J=6.6 Hz, OCH$_2$), 4.27 (t, J=6.3 Hz, 2H, OCH$_2$), 4.34 (dd, J$_{BA}$=14.4 Hz, J=0.6 Hz, 1H, CH$_2$O), 4.64 (dd, J$_{AB}$=14.4 Hz, J=0.6 Hz, 1H, CH$_2$O), 4.72-4.77 (m, 1H, OCHO), 6.52 (d, J=0.6 Hz, 1H, —C=CH—), 6.70 (d, J=5.4 Hz, 1H, Ar—H), 7.53 (d, J=5.4 Hz, 1H, Ar—H), 7.59 (s, 1H, —C=CH—), 7.68 (d, J=5.4 Hz, 1H, Ar—H), 8.57 (d, J=5.4 Hz, 1H, Ar—H).

Example 6

2-(Tetrahydro-pyran-2-yloxymethyl)-5-[5-(7-trifluoromethyl-quinolin-4-ylsulfanyl)-pentyloxy]-4H-pyran-4-one (EHT 9376)

The compound was prepared according to method A with 7-trifluoromethyl-quinoline-4-thiol (0.25 g, 1.09 mmol). After purification by chromatography on silica using as eluent CH$_2$Cl$_2$:MeOH=99:1 a yellow solid EHT 9376 (0.27 g, 47% yield) was obtained.

The structure of compound ex 6 is presented below:

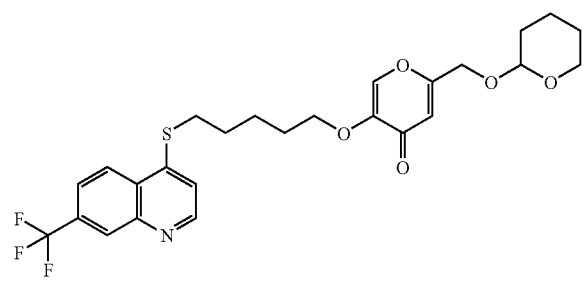

MW: 523.57; Yield: 47%; Yellow solid; Mp=86.4° C. $^1$H-NMR (CD$_3$Cl, δ): 1.49-1.90 (m, 12H, 6×CH$_2$), 3.16 (t, J=7.2 Hz, 2H, CH$_2$S), 3.50-3.58 (m, 1H, CH$_2$O), 3.83-3.91 (m, 1H, CH$_2$O), 3.91 (t, J=6.3 Hz, 2H, CH$_2$O), 4.33 (dd, J$_{BA}$=14.4 Hz, J=0.6 Hz, 1H, CH$_2$O), 4.52 (dd, J$_{BA}$=14.4 Hz, J=0.6 Hz, 1H, CH$_2$O), 4.73 (m, 1H, OCHO), 6.52 (s, 1H, —C=CH—), 7.28 (d, J=4.8 Hz, 1H, Ar—H), 7.58 (s, 1H, —C=CH—), 7.72 (dd, J=8.7 Hz, J=1.8 Hz, 1H, Ar—H), 8.25 (d, J=8.7 Hz, 1H, Ar—H), 8.37 (s, 1H, Ar—H), 8.80 (d, J=4.8 Hz, 1H, Ar—H).

Synthesis of EHT 4745, EHT 6271, EHT 1302

5-(4-Bromo-butoxy)-2-(tetrahydro-pyran-2-yloxymethyl)-4H-pyran-4-one 2

The compound was prepared according to example 11 using 5-hydroxy-2-(tetrahydro-pyran-2-yloxymethyl)-4H-pyran-4-one (1.00 g, 4.42 mmol), Cs$_2$CO$_3$ (1.58 g, 4.86 mmol) and 1,4-dibromobutane (2.00 mL, 16.7 mmol). The sealed tube was heated at 80° C. for 2 h 30. A white solid 2 was obtained (1.14 g, 71% yield).

The structure of compound 2 is presented below:

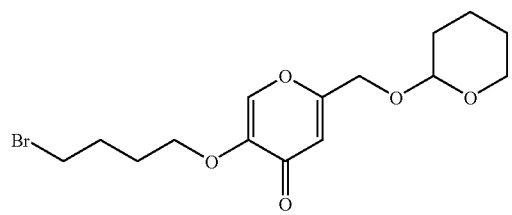

MW: 361.23; Yield: 71%, White solid, Mp=71.5° C. $^1$H-NMR (CDCl$_3$, δ): 1.49-1.91 (m, 6H, 3×CH$_2$), 1.91-2.10 (m, 4H, 2×CH$_2$), 3.48 (t, J=6.5 Hz, 2H, BrCH$_2$), 3.50-3.59 (m, 1H, OCH$_2$), 3.76-3.88 (m, 1H, OCH$_2$), 3.92 (t, J=6.1 Hz, 2H, OCH$_2$), 4.32 (d, J$_{BA}$=14.4 Hz, 1H, =CCH$_2$O), 4.51 (d, J$_{AB}$=14.4 Hz, 1H, =CCH$_2$O), 4.70-4.75 (m, 1H, OCHO), 6.50 (s, 1H, —C=CH—), 7.58 (s, 1H, —C=CH—).

Example 7

2-(Tetrahydro-pyran-2-yloxymethyl)-5-[4-(7-trifluoromethyl-quinolin-4-ylsulfanyl)-butoxy]-4H-pyran-4-one (EHT 4745)

7-Trifluoromethyl-4-quinoline-thiol (0.19 g, 0.87 mmol) was charged in a 25 mL round-bottomed flask equipped with a magnetic stirrer and under inert atmosphere. Anhydrous DMF (10 mL) and NaH 60% dispersion in oil (35 mg, 0.87 mmol) were successively added. After 30 min a solution of 5-(4-bromo-butoxy)-2-(tetrahydro-pyran-2-yloxymethyl)-4H-pyran-4-one 2 (0.30 g, 0.83 mmol) was added at room temperature. The reaction mixture was stirred for 2 h at room temperature. The reaction mixture was poured in 200 mL of H$_2$O, extracted with EtOAc (3×75 mL). The organic layer was washed with brine (4×250 mL), dried over MgSO$_4$, filtered and evaporated to dryness. The crude compound was recrystallized in diethyl ether to give after filtration EHT 4745 (271 mg, 64% yield) as a yellow solid.

The structure of compound ex 7 is presented below:

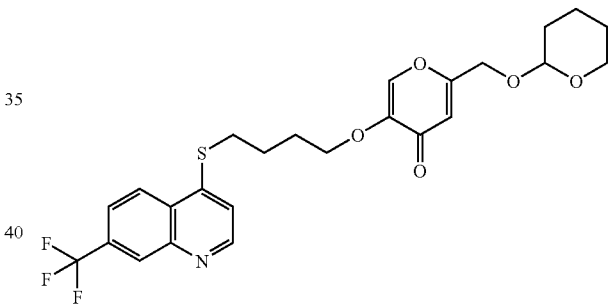

MW: 508.55; Yield: 64%; Yellow pale solid; Mp: 97.3° C. (dec.). R$_f$: 0.12 (AcOEt). $^1$H-NMR (CD$_3$Cl, δ): 1.45-1.92 (m, 6H, 3×CH$_2$), 1.98-2.12 (m, 4H, 2×CH$_2$), 3.19-3.28 (t, J=6.8 Hz, 2H, CH$_2$S), 3.52-3.59 (m, 1H, CH$_2$O), 3.92-4.01 (m, 1H, CH$_2$O), 4.32 (dd, J$_{BA}$=14.4 Hz, J=0.5 Hz, 1H, =CCH$_2$O), 4.52 (dd, J$_{AB}$=14.4 Hz, J=0.5 Hz, 1H, =CCH$_2$O), 4.72 (t, J=3.1 Hz, 2H, OCH$_2$O), 6.52 (s, 1H, —C=CH—), 7.32 (d, J=4.8 Hz, 1H, Ar—H), 7.59 (s, 1H, —C=CH—), 7.71 (dd, J=8.8 Hz, J=1.7 Hz, 1H, Ar—H), 8.24 (d, J=8.8 Hz, 1H, Ar—H), 8.36 (s, 1H, Ar—H), 8.80 (d, J=4.8 Hz, 1H, Ar—H). MS-ESI m/z (rel. Int.): 510 ([MH]$^+$, 30), 426 (100). HPLC: Method A, detection UV 254 nm, EHT 4745 RT=5.33 min, peak area 99.9%.

5-(5-Bromo-hexyloxy)-2-(tetrahydro-pyran-2-yloxymethyl)-4H-pyran-4-one 3

5-Hydroxy-2-(tetrahydro-pyran-2-yloxymethyl)-4H-pyran-4-one (1.50 g, 6.60 mmol) was charged in a 30 mL sealed tube equipped with a magnetic stirrer and under inert atmosphere. Anhydrous DMF (10 mL), Cs$_2$CO$_3$ (2.30 g, 7.00 mmol) and 1,6-dibromo-hexane (3.20 g, 13.30 mmol) were successively added. The reaction mixture was stirred 2 h at 60° C. After evaporation of DMF, the crude compound was purified by column chromatography (SiO$_2$; CH$_2$Cl$_2$: EtOAc=8:2) to give after evaporation 5-(6-bromo-hexyloxy)-2-(tetrahydro-pyran-2-yloxymethyl)-4H-pyran-4-one 3 as an oil (190 mg, 52% yield).

The structure of compound 3 is presented below:

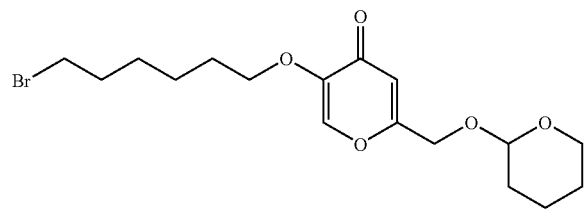

MW: 389.28; Yield: 52%; Oil. $^1$H-NMR (CDCl$_3$, δ): 1.40-1.95 (m, 14H, 7×CH$_2$), 3.45 (t, J=6.7 Hz, 2H, BrCH$_2$), 3.52-3.64 (m, 1H, OCH$_2$), 3.82-3.92 (m, 1H, OCH$_2$), 3.90 (t, J=6.5 Hz, 2H, OCH$_2$), 4.36 (d, J$_{BA}$=14.4 Hz, 1H, =CCH$_2$O), 4.56 (d, J$_{AB}$=14.4 Hz, 1H, =CCH$_2$O), 4.74-4.79 (m, 1H, OCHO), 6.54 (s, 1H, —C=CH—), 7.60 (s, 1H, —C=CH—). MS-ESI m/z (rel. Int.): 389-391 ([MH]$^+$, 97-100).

Example 8

2-(Tetrahydro-pyran-2-yloxymethyl)-5-[6-(7-trifluoromethyl-quinolin-4-ylsulfanyl)-hexyloxy]-4H-pyran-4-one (EHT 6271)

7-Trifluoromethyl-4-quinoline-thiol (0.62 g, 2.70 mmol) was charged in a 50 mL round-bottomed flask equipped with a magnetic stirrer and under inert atmosphere. Anhydrous DMF (20 mL) and NaH 60% dispersion in oil (110 mg, 2.70 mmol) were successively added. After 30 min a solution of 5-(6-bromo-hexyloxy)-2-(tetrahydro-pyran-2-yloxymethyl)-4H-pyran-4-one 3 (1.00 g, 2.57 mmol) was added at room temperature. The reaction mixture was stirred for 2 h at room temperature. The reaction mixture was poured in 200 mL of H$_2$O, extracted with EtOAc (3×80 mL). The organic layer was washed with brine (2×20 mL), dried over MgSO$_4$, filtered and evaporated to dryness. The crude compound was purified by column chromatography (SiO$_2$; CH$_2$Cl$_2$: MeOH=98:2 to 9:1) to give after recrystallisation in diethyl ether EHT 6271 (370 mg, 33% yield) as a white solid.

The structure of compound ex 8 is presented below:

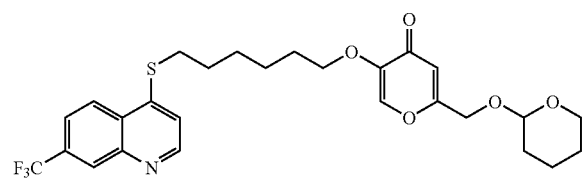

MW: 537.59; Yield: 33%; White solid; Mp: 67.8° C. R$_f$: 0.20 (EtOAc). $^1$H-NMR (CDCl$_3$, δ): 1.56-1.90 (m, 14H, 7×CH$_2$), 3.13 (t, J=7.3 Hz, 2H, CH$_2$S), 3.53-3.57 (m, 1H, O—CH$_2$), 3.79-3.84 (m, 1H, O—CH$_2$), 3.88 (t, J=6.4 Hz, 2H, CH$_2$O), 4.32 (d, J$_{BA}$=14.4 Hz, 1H, O—CH$_2$), 4.52 (d, J$_{AB}$=14.4 Hz, 1H, O—CH$_2$), 4.37 (s, 2H, CH$_2$O), 4.72 (t, J=3.0 Hz, 1H, CH), 6.51 (s, 1H, —C=CH), 7.26 (d, J=4.8 Hz, 1H, Ar—H), 7.56 (s, 1H, —C=CH), 7.71 (dd, J=8.8 Hz, J=1.7 Hz, 1H, Ar—H), 8.24 (d, J=8.7 Hz, 1H, Ar—H); 8.36 (s, 1H, Ar—H), 8.79 (d, J=4.8 Hz, 1H, Ar—H). MS-ESI m/z (rel. Int.): 538.0 ([MH]$^+$, 100). HPLC: Method A, detection UV 254 nm, EHT 6271, RT=5.80 min, peak area 99.8%.

Example 9

2-Hydroxymethyl-5-[5-(7-trifluoromethyl-quinolin-4-ylsulfanyl)-pentyloxy]-4H-pyran-4-one hydrochloride salt (EHT 1302)

EHT 9376 (40.6 mg, 0.0077 mmol) was charged in a 5 mL vial equipped with a magnetic stirrer. 2 mL of MeOH and activated DOWEX (50WX8) (50 mg) were added. The reaction mixture was stirred 2 h at room temperature. The suspension was filtered and the precipitate was washed with a solution of MeOH:HCl 1M=9:1. After evaporation a viscous yellow pale oil 2-hydroxymethyl-5-[5-(7-trifluoromethyl-quinolin-4-ylsulfanyl)-pentyloxy]-4H-pyran-4-one hydrochloride salt EHT 1302 (7 mg, 19% yield) was obtained.

The structure of compound ex 9 is presented below:

MW: 475.91 (HCl salt); Yield: 19%; Yellow pale oil. $^1$H-NMR (CD$_3$OD, δ): δ 1.60-2.00 (m, 6H, 3×CH$_2$), 3.42 (t, J=7.1 Hz, 2H, CH$_2$S), 3.83 (t, J=5.8 Hz, 2H, CH$_2$O), 4.31 (s, 2H, CH$_2$OH), 6.38 (s, 1H, —C=CH—), 7.92 (s, 2H, —C=CH— and Ar—H), 8.05 (d, J=8.8 Hz, 1H, Ar—H), 8.33 (s, 1H, Ar—H), 8.57 (d, J=8.8 Hz, 1H, Ar—H), 8.88 (d, J=6.0 Hz, 1H, Ar—H). $^{13}$C-NMR (CD$_3$OD): 176.79, 170.72, 166.95, 148.95, 144.63, 144.54, 136.75, 136.68, 136.30, 128.86, 127.64, 126.15, 122.52, 120.24, 120.18, 118.24, 111.70, 70.40, 61.06, 32.84, 29.44, 28.34, 26.42. MS-ESI m/z (rel. Int.): 439.95 ([MH]$^+$, 100), 306.08 (10). HPLC: Method A, detection UV 254 nm, EHT 1302 RT=4.63 min, peak area 99.0%.

Preparation of EHT 5909, EHT 2168, EHT 1494, EHT 7365 and EHT 7168

5-(5-Bromo-pentyloxy)-2-(tert-butyl-dimethyl-silanyloxymethyl)-4H-pyran-4-one 7

2-(tert-Butyl-dimethyl-silanyloxymethyl)-5-hydroxy-4H-pyran-4-one 6 (1.50 g, 5.85 mmol) was charged in a 100 mL round-bottomed flask equipped with a magnetic stirrer and under inert atmosphere. Anhydrous DMF (25 mL) and Cs$_2$CO$_3$ (2.10 g, 6.44 mmol) were successively added. After 5 min, 1,5-dibromopentane (2.39 mL, 17.55 mmol) was added via syringe at room temperature. The reaction mixture Novas heated at 50° C. for 3 h. After cooling and filtration DMF was removed in vacuo. The crude oil was purified by chromatography on silica using as eluent EtOAc:cyclohexane=20:80 then 30:70. After evaporation, 5-5-bromo-pentyloxy)-2-(tert-butyl-dimethyl-silanyloxymethyl)-4H-pyran-4-one 7 was obtained (1.25 g, 53% yield) as a white solid.

The structure of compound 7 is presented below:

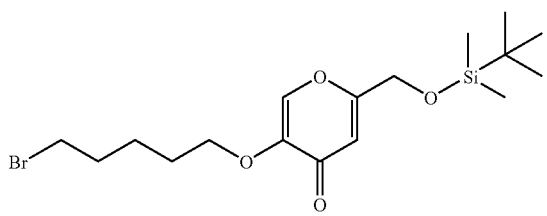

MW: 405.40; Yield: 53%; White solid; Mp=65.3° C. $R_f$: 0.65 (AcOEt:Cyclohexane=50:50). $^1$H-NMR (CD$_3$Cl, δ): 0.11 (s, 6H, 2×CH$_3$), 0.93 (s, 9H, 3×CH$_3$), 1.52-1.68 (m, 2H, CH$_2$), 1.79-1.97 (m, 4H, 2×CH$_2$), 3.43 (t, J=6.7 Hz, 2H, CH$_2$Br), 3.88 (t, J=6.4 Hz, 2H, CH$_2$O), 4.46 (s, 2H, CH$_2$OSi), 6.50 (d, J=0.5 Hz, 1H, —C=CH—), 7.54 (s, 1H, —C=CH). $^{13}$C-NMR (CD$_3$Cl): 174.58, 166.84, 147.81, 139.00, 111.71, 69.38, 61.21, 33.53, 32.36, 28.21, 25.73, 24.58, 18.26, −5.48.

2-(tert-Butyl-dimethyl-silanyloxymethyl)-5-[5-(7-trifluoromethyl-quinolin-4-ylsulfanyl)-pentyloxy]-4H-pyran-4-one 8

7-Trifluoromethyl)-4-quinoline-thiol (0.77 g, 3.37 mmol) was charged in a 100 mL round-bottomed flask equipped with a magnetic stirrer and under inert atmosphere. Anhydrous DMF (20 mL) and NaH 60% dispersion in oil (135 mg, 3.37 mmol) were successively added. After 40 min a solution of 5-(5-bromo-pentyloxy)-2-(tert-butyl-dimethyl-silanyloxymethyl)-4H-pyran-4-one 7 (1.24 g, 3.06 mmol) in 10 mL DMF was added via syringe at room temperature. The reaction mixture was stirred for 2 h at room temperature. The reaction mixture was poured in 500 mL of H$_2$O, extracted with EtOAc (3×150 mL). The organic layer was washed with brine (4×250 mL), dried over MgSO$_4$, filtered and evaporated in vacuo. The crude yellow solid was purified by chromatography on silica using as eluent EtOAc:cyclohexane=50:50 then 60:40. After evaporation, 2-(tert-butyl-dimethyl-silanyloxymethyl)-5-[5-(7-trifluoromethyl-quinolin-4-ylsulfanyl)-pentyloxy]-4H-pyran-4-one 8 was obtained (1.27 g, 75% yield) as a yellow solid.

The structure of compound 8 is presented below:

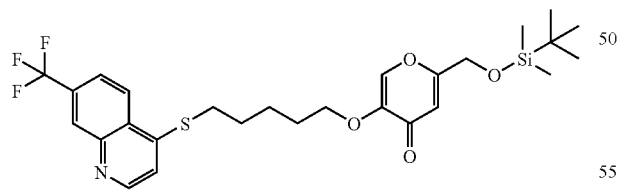

MW: 553.71; Yield: 75%; Yellow solid. $R_f$: 0.31 (EtOAc:cyclohexane=60:40). $^1$H-NMR (CD$_3$Cl, δ): 0.11 (s, 6H, 2×CH$_3$), 0.93 (s, 9H, 3×CH$_3$), 1.60-1.78 (m, 2H, CH$_2$), 1.80-1.95 (m, 4H, 2×CH$_2$), 3.15 (t, J=7.2 Hz, 2H, CH$_2$S), 3.89 (t, J=6.2 Hz, 2H, CH$_2$O), 4.46 (s, 2H, CH$_2$OSi), 6.51 (d, J=0.8 Hz, 1H, —C=CH—), 7.26 (d, J=4.8 Hz, 1H, Ar—H), 7.53 (s, 1H, —C=CH), 7.71 (dd, J=8.8 Hz, J=1.4 Hz, 1H, Ar—H), 8.23 (d, J=8.8 Hz, 1H, Ar—H), 8.36 (s, 1H, Ar—H), 8.79 (d, J=4.8 Hz, 1H, Ar—H). MS-ESI m/z (rel. Int.): 554.0 ([MH]$^+$, 100). HPLC: Method A, detection UV 254 nm, RT=6.57 min.

Example 10

2-Hydroxymethyl-5-[5-(7-trifluoromethyl-quinolin-4-ylsulfanyl)-pentyloxy]-4H-pyran-4-one (EHT 5909)

In a 50 mL round-bottomed flask 2-(tert-butyl-dimethyl-silanyloxymethyl)-5-[5-(7-trifluoromethyl-quinolin-4-ylsulfanyl)-pentyloxy]-4H-pyran-4-one 8 (1.20 g, 2.17 mmol) was dissolved in 25 mL of THF. A solution of n-tetrabutylammonium fluoride in THF (2.38 mL, 2.38 mmol) was added via syringe. The reaction mixture was stirred 1 h at RT. The reaction mixture was evaporated in vacuo and the crude product was purified by chromatography on silica using as eluent CH$_2$Cl$_2$:MeOH=95:5. After evaporation a yellow light solid EHT 5909 (0.73 g, 77% yield) was obtained.

The structure of compound ex 10 is presented below:

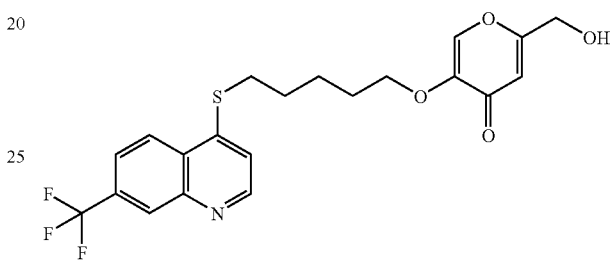

MW: 439.11; Yield: 77%; Yellow pale solid; Mp=133.2° C. (dec., EtOAc). $R_f$: 0.23 (CH$_2$Cl$_2$:MeOH=95:5). $^1$H-NMR (CD$_3$Cl, δ): 1.65-1.76 (m, 2H, CH$_2$), 1.77-1.95 (m, 4H, 2×CH$_2$), 3.14 (t, J=7.2 Hz, 2H, CH$_2$S), 3.86 (t, J=8.2 Hz, 2H, CH$_2$O), 4.12 (s broad, 1H, OH), 4.49 (s, 2H, CH$_2$OH), 6.52 (s, 1H, —C=CH—), 7.26 (d, J=4.8 Hz, 1H, Ar—H), 7.54 (s, 1H, —C=CH—), 7.70 (dd, J=8.8 Hz, J=1.7 Hz, 1H, Ar—H), 8.22 (d, J=8.8 Hz, 1H, Ar—H), 8.33 (s, 1H, Ar—H), 8.74 (d, J=4.8 Hz, 1H, Ar—H). $^{13}$C-NMR (CD$_3$Cl): 174.70, 167.23, 150.42, 148.56, 147.79, 146.39, 139.29, 128.14, 127.50, 125.00, 121.89, 117.26, 111.98, 69.29, 60.81, 30.99, 28.55, 27.76, 25.40. MS-ESI m/z (rel. Int.): 439.9 (([MH]$^+$, 100), 298.08 (5), 211 (10), 142.9 (5). HPLC: Method A, detection UV 254 nm, EHT 5909 RT=4.60 min, peak area 99.9%.

Example 11

2-Methoxymethoxymethyl-5-[5-(7-trifluoromethyl-quinolin-4-ylsulfanyl)-pentyloxy]-4H-pyran-4-one (EHT 2168)

2-Hydroxymethyl-5-[5-(7-trifluoromethyl-quinolin-4-ylsulfanyl)-pentyloxy]-4H-pyran-4-one EHT 5909 (0.10 g, 0.227 mmol) was charged in a 25 mL three necked round bottom flask equipped with a magnetic stirrer and under a nitrogen atmosphere. THF (6 mL) and NaH (60% dispersion in oil, 10 mg, 0.25 mmol) were added at room temperature. After the reaction mixture was stirred for 5 min, methyl choromethyl ether (18.1 µl, 0.24 mmol, 1.05 eq.) was added via syringe and the reaction mixture was stirred for 2 h 30 at room temperature. The reaction mixture was poured in H$_2$O (60 mL) and extracted with EtOAc (3×20 mL). The organic layer was dried over MgSO$_4$, filtered and evaporated in vacuo. The crude product was purified by chromatography on silica using as eluent MeOH:CH$_2$Cl$_2$=2:98. After evaporation and drying to the vacuum pump a white pale yellow solid EHT 2168 was obtained (74 mg, 67% yield).

The structure of compound ex 11 is presented below:

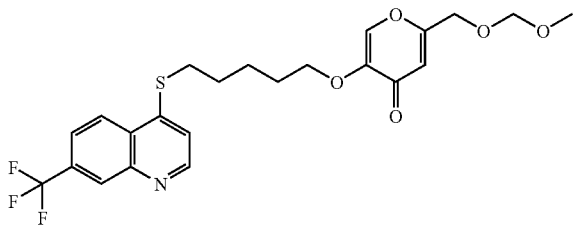

MW: 483.50; Yield: 67%; Yellow pale solid; Mp: 88.1° C. $R_f$: 0.42 ($CH_2Cl_2$:MeOH=95:5). $^1$H-NMR ($CD_3Cl$, δ): 1.73-1.80 (m, 2H, $CH_2$—$CH_2$—$CH_2$), 1.82-1.98 (m, 4H, $CH_2$—$CH_2$—$CH_2$), 3.15 (t, J=7.2 Hz, 2H, $CH_2S$), 3.40 (s, 3H, MeO), 3.89 (t, J=6.2 Hz, 2H, $CH_2O$), 4.37 (s, 2H, $CH_2O$), 4.70 (s, 2H, $CH_2O$), 6.48 (s, 1H, —C═CH—), 7.26 (d, J=4.8 Hz, 1H, Ar—H), 7.56 (s, 1H, —C═CH—), 7.71 (dd, J=8.8 Hz, J=1.7 Hz, 1H, Ar—H), 8.23 (d, J=8.8 Hz, 1H, Ar—H), 8.35 (s, 1H, Ar—H), 8.79 (d, J=4.8 Hz, 1H, Ar—H). MS-ESI m/z (rel. Int.): 484.1 ([MH]$^+$, 100), 255 (5). HPLC: Method A, detection UV 254 nm, EHT 2168 RT=5.19 min, peak area 99.9%

Methanesulfonic acid 4-oxo-5-[5-(7-trifluoromethyl-quinolin-4ylsulfanyl)-pentyloxy]-4H-pyran-2-ylmethyl ester 9

To a suspension of 2-hydroxymethyl-5-[5-(7-trifluoromethyl-quinolin-4-ylsulfanyl)-pentyloxy]-4H-pyran-4-one EHT 5909 (0.10 g, 0.23 mmol) in 4 mL of dichloromethane at 5° C. were added triethylamine (35 µl, 0.25 mmol) and methanesulfonyl chloride (19.4 µl, 0.25 mmol). The reaction mixture was stirred 18 h at room temperature. Dichloromethane (20 mL) was added and the solution was washed with aqueous $NaHCO_3$ 10% (2×30 mL). The organic layer was dried over $MgSO_4$, filtered and evaporated in vacuo. The crude product was purified by chromatography on silica using as eluent $CH_2Cl_2$:MeOH=98:2. After evaporation methanesulfonic acid 4-oxo-5-[6-(7-trifluoromethyl-quinolin-4-ylsulfanyl)-hexyloxy]-4H-pyran-2-ylmethyl ester 9 (83 mg, 69%) was obtained as a white solid.

The structure of compound 9 is presented below:

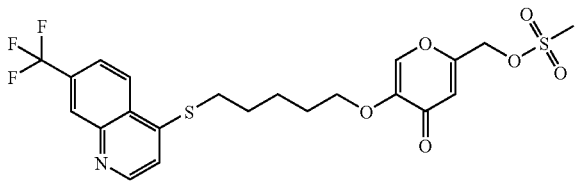

MW: 517.54; Yield: 69%; White solid; Mp=122.1° C. (dec.). $R_f$: 0.44 ($CH_2Cl_2$:MeOH=95:5). $^1$H-NMR ($CD_3Cl$, δ): 1.63-1.78 (m, 2H, $CH_2$), 1.80-1.95 (m, 4H, 2×$CH_2$), 3.11 (s, 3H, MeS); 3.15 (t, J=7.2 Hz, 2H, $CH_2S$), 3.90 (t, J=6.2 Hz, 2H, $CH_2O$), 4.98 (s, 2H, $CH_2OH$), 6.52 (s, 1H, —C═CH—), 7.26 (d, J=4.8 Hz, 1H, Ar—H), 7.60 (s, 1H, —C═CH—), 7.71 (dd, J=8.8 Hz, J=1.8 Hz, 1H, Ar—H), 8.23 (d, J=8.8 Hz, 1H, Ar—H), 8.35 (s, 1H, Ar—H), 8.79 (d, J=4.8 Hz, 1H, Ar—H). MS-ESI m/z (rel. Int.): 517.81 ([MH]$^+$, 100). HPLC: Method A, detection UV 254 nm, RT=5.04 min, peak area 97.0%.

Example 12

2-Chloromethyl-5-[5-(7-trifluoromethyl-quinolin-4-ylsulfanyl)-pentyloxy]-4H-pyran-4-one (EHT 1494)

The compound was prepared according the above procedure from EHT 5909 instead that after the reaction, the mixture was evaporated to dryness and let 18 h at room temperature (a spontaneous reaction between the mesylate and triethylamine hydrochloride occurred). Purification by preparative HPLC ($CH_3CH$:$H_2O$:TFA 1/1000 gradient) yielded to EHT 1494 (43%) as a yellow solid.

The structure of compound ex 12 is presented below:

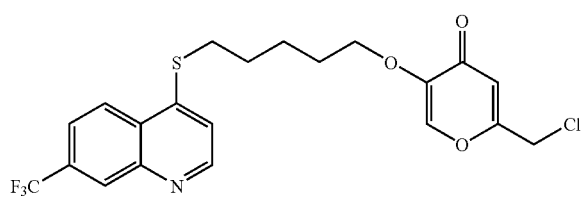

MW: 457.89; Yield: 43%; Yellow solid; Mp: 38.2° C. $R_f$: 0.35 ($CH_2Cl_2$:MeOH=9:1). $^1$H-NMR ($CDCl_3$, δ): 1.70-2.00 (m, 6H, $CH_2$), 3.26 (t, J=6.9 Hz, 2H, $CH_2S$), 3.92 (t, J=5.8 Hz, 2H, $CH_2O$), 4.33 (s, 2H, Cl—$CH_2$), 6.50 (s, 1H, —C═CH), 7.50 (m, 1H, Ar—H), 7.61 (s, 1H, —C═CH), 7.83 (d, J=8.8 Hz, 1H, Ar—H), 8.33 (d, J=8.8 Hz, 1H, Ar—H), 8.59 (s, 1H, Ar—H), 8.92 (m, 1H, Ar—H). MS-ESI m/z (rel. Int.): 457.9-459.8 ([MH]$^+$, 100). HPLC: Method A, Detection UV 254 nm, EHT 1494, RT=5.39 min, purity 94.7%.

Example 13

2-(4-Methyl-piperazin-1-ylmethyl)-5-[5-(7-trifluoromethyl-quinolin-4-ylsulfanyl)-pentyloxy]-4H-pyran-4-one (EHT 7365)

Methanesulfonic acid 4-oxo-5-[6-(7-trifluoromethyl-quinolin-4-ylsulfanyl)-hexyloxy]-4H-pyran-2-ylmethyl ester 9 (82 mg, 0.16 mmol) in 1.5 mL of dichloromethane was charged in a 10 mL round-bottomed flask equipped with a magnetic stirrer and under $N_2$ atmosphere. 1-Methylpiperazine (35.1 µl, 0.32 mmol) was added via syringe and the reaction mixture was heated at 45° C. for 2 h 40. The reaction mixture was evaporated to dryness, recrystallized in EtOAc, washed by $Et_2O$. 40 mL of dichloromethane were added and the solution was washed with successively $NaHCO_3$ at 5% (40 mL) and brine (40 mL). The solution was dried over $MgSO_4$, filtered and evaporated to give a pale yellow solid EHT 7365 (59 mg, 72% yield).

The structure of compound ex 13 is presented below:

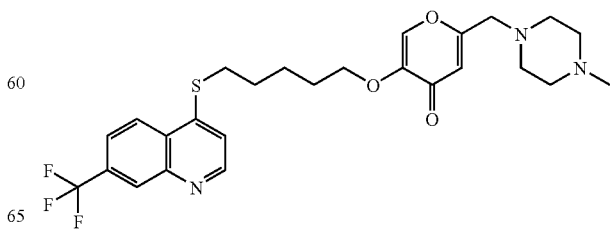

MW: 521.59; Yield: 72%; Yellow pale solid; Mp: 112.6° C. (dec.). $R_f$: 0.26 (CH$_2$Cl$_2$:MeOH=90:10). $^1$H-NMR (CD$_3$Cl, δ): 1.61-1.79 (m, 2H, CH$_2$—CH$_2$—CH$_2$), 1.82-1.98 (m, 4H, CH$_2$—CH$_2$—CH$_2$), 2.31 (s, 3H, CH$_3$N), 2.20-2.75 (m, 8H, CH$_2$—N—CH$_2$ and CH$_2$—N(CH$_3$)—CH$_2$), 3.15 (t, J=7.2 Hz, 2H, CH$_2$S), 3.37 (s, 2H, =CCH$_2$N), 3.89 (t, J=6.2 Hz, 2H, CH$_2$O), 6.45 (s, 1H, —C=CH—), 7.26 (d, J=4.8 Hz, 1H, Ar—H), 7.56 (s, 1H, —C=CH—), 7.71 (dd, J=8.8 Hz J=1.7 Hz, 1H, Ar—H), 8.23 (d, J=8.8 Hz, 1H, Ar—H), 8.35 (s, 1H, Ar—H), 8.79 (d, J=4.8 Hz, 1H, Ar—H). MS-ESI m/z (rel. Int.): 521.9 ([MH]$^+$, 100); 297.9 (20), 282.1 (20), 229.9 (30). HPLC: Method A, detection UV 254 nm, EHT 7365 RT=4.12 min, peak area 98.4%, impurity RT=5.24, 1.6%.

Example 14

2-Morpholin-4-ylmethyl-5-[5-(7-trifluoromethyl-quinolin-4-ylsulfanyl)-pentyloxy]-4H-pyran-4-one (EHT 7168)

Methanesulfonic acid 4-oxo-5-[6-(7-trifluoromethyl-quinolin-4-ylsulfanyl)-hexyloxy]-4H-pyran-2-ylmethyl ester 9 (96 mg, 0.184 mmol) in 1.8 mL of dichloromethane was charged in a 10 mL round-bottomed flask equipped with a magnetic stirrer and under N$_2$ atmosphere. Morpholine (41 μl, 0.46 mmol) was added via syringe and the reaction mixture was heated at 45° C. for 3 h 30. The reaction mixture was evaporated to dryness, recrystallized in EtOAc, washed by Et$_2$O. 40 mL of dichloromethane were added and the solution was washed with successively NaHCO$_3$ at 5% (40 mL) and brine (40 mL). The solution was dried over MgSO$_4$, filtered and evaporated to give a pale yellow solid EHT 7168 (60 mg, 64% yield).

The structure of compound ex 14 is presented below:

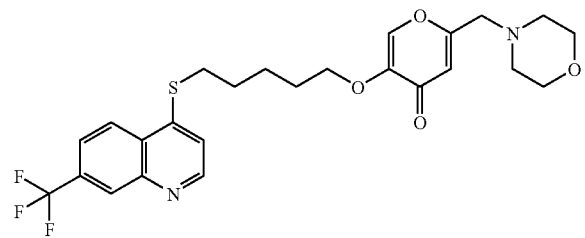

MW: 508.55; Yield: 64%; Yellow light solid; Mp=93.3° C. $R_f$: 0.33 (EtOAc) $^1$H-NMR (CDCl$_3$, δ): 1.72-1.74 (m, 2H, CH$_2$), 1.88-1.92 (m, 4H, 2×CH$_2$), 2.51-2.52 (m, 4H, CH$_2$—N—CH$_2$), 3.13-3.18 (t, J=7.0 Hz, 2H, —SCH$_2$), 3.36 (s, 2H, —NCH$_2$), 3.72-3.73 (m, 4H, CH$_2$—O—CH$_2$), 3.87-3.91 (t, J=6.0 Hz, 2H, O—CH$_2$), 6.47 (s, 1H, —CH=C), 7.26 (m, 1H, Ar—H), 7.56 (s, 1H, —CH=C), 7.69-7.72 (d, J=8.8 Hz, 1H, Ar—H), 8.23-8.25 (d, J=8.7 Hz, 1H, Ar—H), 8.36 (s, 1H, Ar—H), 8.78-8.80 (d, J=4.7 Hz, 1H, Ar—H). MS-ESI m/z (rel. Int.): 509.1 ([MH]$^+$, 100). HPLC: Method A, detection UV 254 nm, EHT 7168 RT=4.37 min, peak area 99.9%.

Preparation of EHT 8883 and EHT 1006

5-(7-Bromo-heptyloxy)-2-(tetrahydro-pyran-2-yloxymethyl)-4H-pyran-4-one 4

The compound was prepared according to example 11 procedure using 5-hydroxy-2-(tetrahydro-pyran-2-yloxymethyl)-4H-pyran-4-one (1.00 g, 4.42 mmol), Cs$_2$CO$_3$ (1.58 g, 4.86 mmol) and 1,7-dibromoheptane (2.5 mL, 14.6 mmol). The sealed tube was heated at 80° C. for 2 h 30. A white solid 5-(7-bromo-heptyloxy)-2-(tetrahydro-pyran-2-yloxymethyl)-4H-pyran-4-one 4 was obtained (1.40 g, 78% yield).

The structure of compound 4 is presented below:

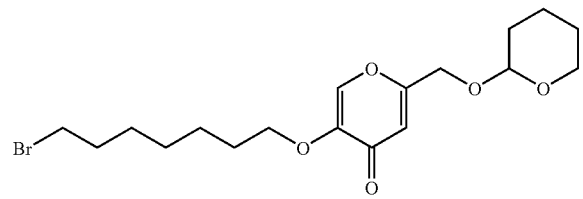

MW: 403.31; Yield: 78%, White solid. $^1$H-NMR (CDCl$_3$, δ): 1.25-1.92 (m, 16H, 8×CH$_2$), 3.40 (t, J=6.8 Hz, 2H, BrCH$_2$), 3.50-3.59 (m, 1H, OCH$_2$), 3.78-3.88 (m, 1H, OCH$_2$), 3.85 (t, J=6.6 Hz, 2H, OCH$_2$), 4.32 (d, $J_{BA}$=14.4 Hz, 1H, =CCH$_2$O), 4.51 (d, $J_{AB}$=14.4 Hz, 1H, =CCH$_2$O), 4.70-4.75 (m, 1H, OCHO), 6.50 (s, 1H, —C=CH—), 7.55 (s, 1H, —C=CH—).

Example 15

5-(7-(7-(Trifluoromethyl)quinolin-4-ylthio)heptyloxy)-2-((tetrahydro-2H-pyran-2-yloxy)methyl)-4H-pyran-4-one (EHT 8883)

7-Trifluoromethyl-4quinoline-thiol (320 mg, 1.4 mmol) was charged in a 50 mL round-bottomed flask equipped with a magnetic stirrer and under inert atmosphere. Anhydrous DMF (10 mL) and NaH 60% dispersion in oil (55 mg, 1.4 mmol) were successively added at 4° C. After 30 min a solution of 5-(7-bromo-heptyloxy)-2-(tetrahydro-pyran-2-yloxymethyl)-4H-pyran-4-one 4 (520 mg, 1.3 mmol) in DMF (6 mL) was added at room temperature. The reaction mixture was stirred for 2 h at room temperature. The reaction mixture was poured in 150 mL of H$_2$O, extracted with EtOAc (3×80 mL). The organic layer was washed with brine (2×20 mL), dried over MgSO$_4$, filtered and evaporated to dryness. The crude compound was purified by column chromatography (SiO$_2$; CH$_2$Cl$_2$:MeOH=95:5 to 98:2) to give 5-(7-(7-(trifluoromethyl)quinolin-4-ylthio)heptyloxy)-2-((tetrahydro-2H-pyran-2-yloxy)methyl)-4H-pyran-4-one EHT 8883 (310 mg, 43% yield) as an oil.

The structure of compound ex 15 is presented below:

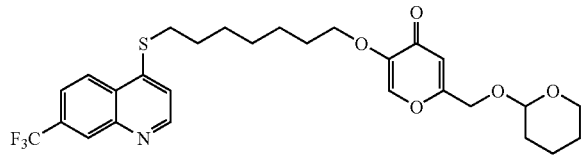

MW: 551.62; Yield: 43%; Oil. $R_f$: 0.23 (CH$_2$Cl$_2$: MeOH=97:3). $^1$H-NMR (CDCl$_3$, δ): 1.40-1.88 (m, 16H, CH$_2$), 3.12 (t, J=7.3 Hz, 2H, S—CH$_2$), 3.53-3.57 (m, 1H, O—CH$_2$), 3.79-3.88 (m, 1H, O—CH$_2$), 3.86 (t, J=6.5 Hz, 2H, O—CH$_2$), 4.32 (d, $J_{BA}$=14.4 Hz, 1H, O—CH$_2$), 4.52 (d, $J_{AB}$=14.4 Hz, 1H, O—CH$_2$), 4.72 (t, J=3.0 Hz, 1H, CH), 6.51 (s, 1H, —C=CH), 7.27 (d, J=5.8 Hz, 1H, Ar—H), 7.55 (s, 1H, —C=CH), 7.71 (dd, J=8.8 Hz, J=1.8 Hz, 1H, Ar—H), 8.24 (d, J=8.8 Hz, 1H, Ar—H), 8.36 (s, 1H, Ar—H), 8.79 (d, J=4.8 Hz, 1H, Ar—H). MS-ESI m/z (rel. int.): 552.0 ([MH]$^+$, 100). HPLC: Method A, detection UV 254 nm, EHT 8883 RT=5.90 min, peak area 99.2%.

5-(8-Bromo-octyloxy)-2-(tetrahydro-pyran-2-yloxymethyl)-4H-pyran-4-one 5

The compound was prepared according to the example 11 procedure using 5-hydroxy-2-(tetrahydro-pyran-2-yloxymethyl)-4H-pyran-4-one (1.00 g, 4.42 mmol), Cs$_2$CO$_3$ (1.58 g, 4.86 mmol) and 1,8-dibromooctane (4.12 mL, 22.1 mmol). The sealed tube was heated at 80° C. for 2 h 30. A white solid 5 was obtained (1.40 g, 78% yield).

The structure of compound 5 is presented below:

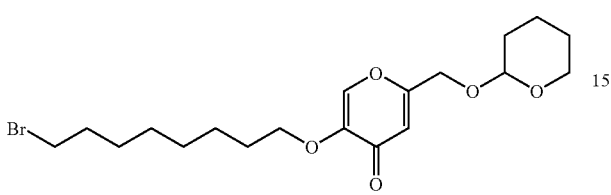

MW: 417.33; Yield: 62%; Yellow oil. $^1$H-NMR (CDCl$_3$, δ): 1.25-1.92 (m, 18H, 9×CH$_2$), 3.40 (t, J=6.8 Hz, 2H, BrCH$_2$), 3.50-3.59 (m, 1H, OCH$_2$), 3.78-3.88(m, 1H, OCH$_2$), 3.85 (t, J=6.6 Hz, 2H, OCH$_2$), 4.32 (d, J$_{BA}$=14.4 Hz, 1H, =CCH$_2$O), 4.51 (d, J$_{AB}$=14.4 Hz, 1H, =CCH$_2$O), 4.70-4.75 (m, 1H, OCHO), 6.50 (s, 1H, —C=CH—), 7.55 (s, 1H, —C=CH—).

Example 16

5-(8-(7-(Trifluoromethyl)quinolin-4-ylthio)octyloxy)-2-((tetrahydro-2H-pyran-2-yloxy)methyl)-4H-pyran-4-one (EHT 1006)

7-Trifluoromethyl-4-quinoline-thiol (300 mg, 1.3 mmol) was charged in a 50 mL round-bottomed flask equipped with a magnetic stirrer and under inert atmosphere. Anhydrous DMF (10 mL) and NaH 60% dispersion in oil (53 mg, 1.3 mmol) were successively added at 4° C. After 30 min a solution of 5-(8-bromo-octyloxy)-2-(tetrahydro-pyran-2-yloxymethyl)-4H-pyran-4-one 5 (500 mg, 1.2 mmol) in DMF (5 mL) was added at room temperature. The reaction mixture was stirred for 2 h at room temperature. The reaction mixture was poured in 150 mL of H$_2$O, extracted with EtOAc (3×80 mL). The organic layer was washed with brine (2×20 mL), dried over MgSO$_4$, filtered and evaporated to dryness. The crude compound was purified by column chromatography (SiO$_2$; CH$_2$Cl$_2$:MeOH=95:5 to 98:2) to give 5-(8-(7-(trifluoromethyl)quinolin-4-ylthio)octyloxy)-2-((tetrahydro-2H-pyran-2-yloxy)methyl)-4H-pyran-4-one EHT 1006 (320 mg, 47% yield) as a white solid.

The structure of compound ex 16 is presented below:

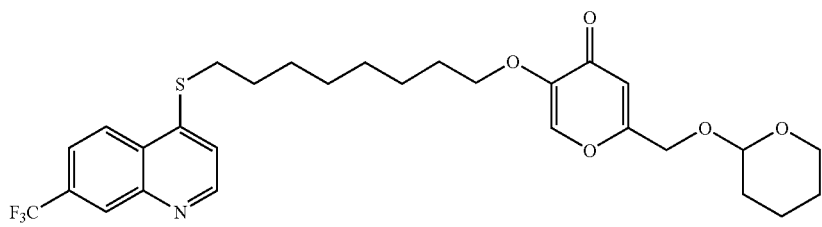

MW: 565.64; Yield: 47%; White solid; Mp: 66.1° C. R$_f$: 0.25 (CH$_2$Cl$_2$:MeOH=97:3). $^1$H-NMR (CDCl$_3$, δ): 1.39-1.85 (m, 18H, CH$_2$), 3.12 (t, J=7.3 Hz, 2H, S—CH$_2$), 3.53-3.57 (m, 1H, O—CH$_2$), 3.79-3.87 (m, 1H, O—CH$_2$), 3.85 (t, J=6.4 Hz, 2H, O—CH$_2$), 4.32 (d, J$_{BA}$=14.4 Hz, 1H, O—CH$_2$), 4.52 (d, J$_{AB}$=14.4 Hz, 1H, O—CH$_2$), 4.72 (t, J=3.0 Hz, 1H, CH), 6.51 (s, 1H, —C=CH), 7.27 (d, J=5.1 Hz, 1H, Ar—H), 7.55 (s, 1H, —C=CH), 7.71 (dd, J=8.7 Hz, J=1.7 Hz, 1H, Ar—H), 8.24 (d, J=8.7 Hz, 1H, Ar—H); 8.36 (s, 1H, Ar—H), 8.79 (d, J=4.8 Hz, 1H, Ar—H). MS-ESI m/z (rel. int.): 566.0 ([MH]$^+$, 100). HPLC: Method A, detection UV 254 nm, EHT 1006 RT=6.10 min, peak area 99.5%.

Preparation of Intermediates Compounds 10-15

5-(5-Bromopentyloxy)-2-(hydroxymethyl)-4H-pyran-4-one 10

Kojic acid (2 g, 14.1 mmol), Cs$_2$CO$_3$ (4.6 g, 14.1 mmol) and DMF (12 mL) were charged in a 100 ml round-bottomed flask equipped with a magnetic stirrer. 1,5-Dibromopentane (8.1 g, 35.2 mmol) was added and the reaction mixture was stirred for 2 h at 110° C. After evaporation of DMF, the reaction mixture was poured in 50 mL of H$_2$O, extracted with CH$_2$Cl$_2$ (2×100 mL). The organic layer was washed with brine (2×20 mL), dried over MgSO$_4$, filtered and evaporated to dryness. The crude compound was purified by column chromatography (SiO$_2$; CH$_2$Cl$_2$:MeOH 99:1 to 95:5) to give after evaporation 5-(5-bromopentyloxy)-2-(hydroxymethyl)-4H-pyran-4-one 10 (1.9 g, 46% yield) as a brown oil.

The structure of compound 10 is presented below:

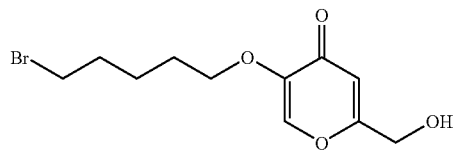

MW: 291.14; Yield: 46%; Brown oil. R$_f$: 0.60 (CH$_2$Cl$_2$:MeOH=9:1). $^1$H-NMR (CDCl$_3$, δ): 1.57-1.63 (m, 2H, CH$_2$), 1.81-1.94 (m, 4H, CH$_2$), 3.43 (t, J=6.7 Hz, 2H, Br—CH$_2$), 3.85 (t, J=6.4 Hz, 2H, O—CH$_2$), 4.48 (s, 2H, O—CH$_2$), 6.52 (s, 1H, —C=CH), 7.61 (s, 1H, —C=CH). $^{13}$C-NMR (CDCl$_3$, δ): 22.28, 24.50, 28.10, 32.29, 33.61, 60.56, 69.27, 111.44, 139.24, 147.58, 168.28, 175.03. MS-ESI m/z (rel. Int.): 291.0/293.0 ([MH]$^+$). HPLC: Method A, detection UV 254 nm, RT=4.5 min, peak area 98.0%.

5-(5-(6-(trifluoromethyl)quinolin-4-yloxy)pentyloxy)-2-(hydroxymethyl)-4H-pyran-4-one 11

6-Trifluoromethyl-quinolin-4-ol (0.23 g, 1.08 mmol) was dissolved in DMF (3 mL). $Cs_2CO_3$ (0.35 g, 1.08 mmol) was added at RT and the mixture was stirred for 10 min. A solution of 5-(5-bromo-pentyloxy)-2-hydroxymethyl-pyran-4-one 10 (0.30 g, 1.03 mmol) in DMF (2 mL) was added via syringe. This mixture was stirred at 50° C. for 1 h. Water (10 mL) was added and the mixture extracted with EtOAc (2×50 mL), washed with water (3×50 mL), brine (3×50 mL) dried over $MgSO_4$, filtered and evaporated. The crude product was purified by column chromatography on silica using as eluent ($CH_2Cl_2$:MeOH)=90:10. 5-(5-(6-(trifluoromethyl)quinolin-4-yloxy)pentyloxy)-2-(hydroxymethyl)-4H-pyran-4-one 11 was obtained (93 mg, 21% yield) as a yellow oil.

The structure of compound 11 is presented below:

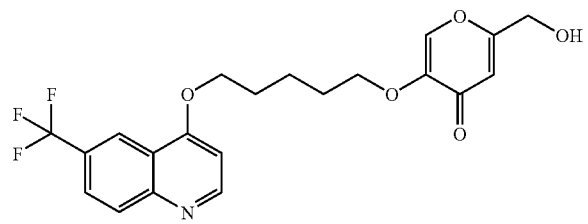

MW: 423.38; Yield: 21%; Yellow oil. $R_f$: 0.2 ($CH_2Cl_2$:MeOH=90:10). $^1$H-NMR ($CDCl_3$, d): 1.70-1.81 (m, 2H, $CH_2$), 1.88-2.10 (m, 4H, 2×$CH_2$), 3.90 (t, 2H, J=6.2 Hz, —$CH_2$—O), 4.20 (t, 2H, J=6.4 Hz, —O—$CH_2$), 4.52 (s, 2H, —$CH_2$O), 6.52 (s, 1H, —CH=C), 6.81 (d, 1H, J=5.4 Hz, ArH), 7.58 (s, 1H, —CH=C), 7.87 (dd, 1H, J=8.8 Hz J=2.0 Hz, ArH), 8.14 (d, 1H, J=8.8 Hz, ArH), 8.51 (s, 1H, ArH), 8.80 (d, 1H, J=5.3 Hz, ArH). MS-ESI m/z (rel. Int.): 423.83 ([MH]$^+$, 30), 210.97 (100). HPLC: Method A, detection UV 254 nm, RT=4.30 min, peak area 88.0%.

5-(5-(7-(Trifluoromethyl)quinolin-4-yloxy)pentyloxy)-2-(hydroxymethyl)-4H-pyran-4-one 12

7-Trifluoromethyl-4-quinolinol (320 mg, 1.5 mmol), $Cs_2CO_3$ (500 mg, 1.5 mmol) and anhydrous DMF (3 mL) were stirred at 70° C. in a 50 ml round-bottomed flask equipped with a magnetic stirrer. After 20 min, 5-(5-bromopentyloxy)-2-(hydroxymethyl)-4H-pyran-4-one 10 (420 mg, 1.4 mmol) in DMF (2 mL) was added and the reaction mixture was stirred for 15 h at 75° C. DMF was evaporated at 60° C. and the reaction mixture was poured in 20 mL of $H_2O$ and extracted with EtOAc (3×100 mL). The organic layer was washed with brine (10 mL), dried over $MgSO_4$, filtered and evaporated to dryness. The crude compound was purified by column chromatography ($SiO_2$; $CH_2Cl_2$:MeOH=98:2 to 90:10) to give after evaporation 5-(5-(7-(trifluoromethyl)quinolin-4-yloxy)pentyloxy)-2-(hydroxymethyl)-4H-pyran-4-one 12 (300 mg, 47% yield) as a white solid.

The structure of compound 12 is presented below:

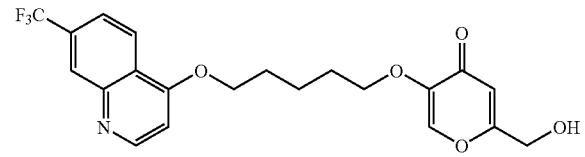

MW: 423.38; Yield: 47%; White solid; Mp: 116.1° C. $R_f$: 0.25 ($CH_2Cl_2$:MeOH=95:5). $^1$H-NMR ($CDCl_3$, δ): 1.68-1.73 (m, 2H, C—$CH_2$), 1.86-2.01 (m, 4H, C—$CH_2$), 3.88 (t, J=6.2 Hz, 2H, O—$CH_2$), 4.21 (t, J=6.3 Hz, 2H, O—$CH_2$), 4.50 (s, 2H, O—$CH_2$), 6.57 (s, 1H, C=CH), 6.81 (d, 1H J=5.3Hz, ArH), 7.57 (s, 1H, C=CH), 7.65 (dd, 1H J=8.7 Hz, J=1.5 Hz, ArH), 8.27-8.32 (m, 2H, ArH), 8.76 (d, 1H, J=5.2 Hz, ArH). $^{13}$C-NMR ($CDCl_3$, δ): 22.61, 28.44, 28.67, 60.69, 68.56, 69.36, 102.20, 111.82, 119.55, 121.23, 122.11, 123.18, 123.46, 126.27, 131.82, 139.17, 147.76, 152.70, 161.55, 167.69, 174.84. MS-ESI m/z (rel. Int.): 424.0 ([MH]$^+$). HPLC: Method A, detection UV 254 nm, RT=4.30 min, peak area 99.5%.

4-[5-(6-Hydroxymethyl-4-oxo-4H-pyran-3-yloxy)-pentyloxy]-7-trifluoromethyl-quinoline-3-carboxylic acid ethyl ester 13

4-Hydroxy-7-trifluoromethyl-quinoline-3-carboxylic acid ethyl ester (0.86 g, 3.02 mmol) was dissolved in DMF (10 mL). $Cs_2CO_3$ (0.98 g, 3.02 mmol) was added at RT and the mixture was stirred for 10 min. A solution of 5-(5-bromo-pentyloxy)-2-hydroxymethyl-pyran-4-one 10 (0.86 g, 3.02 mmol) in DMF (5 mL) was added via syringe. This mixture was stirred at 50° C. for 22 h. Water (10 mL) was added and the mixture extracted with EtOAc (2×50 mL), washed with water (3×50 mL), brine (3×50 mL) dried over $MgSO_4$, filtered and evaporated. The crude product was purified by column chromatography on silica using as eluent ($CH_2Cl_2$:MeOH)=90:10. 4-[5-(6-Hydroxymethyl-4-oxo-4H-pyran-3-yloxy)-pentyloxy]-7-trifluoromethyl-quinoline-3-carboxylic acid ethyl ester 13 was obtained (0.43 g, 31% yield) as a pale yellow foam.

The structure of compound 13 is presented below:

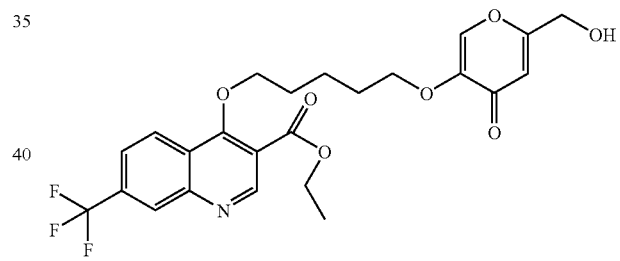

MW: 495.45; Yield: 31%; pale yellow foam. Rf: 0.5 ($CH_2Cl_2$:MeOH=9:1). MS-ESI m/z (rel. Int.): 495.86 ([MH]$^+$, 100). HPLC: Method A, detection UV 254 nm, RT=4.91 min, peak area 98.1%.

5-(5-(8-(Trifluoromethyl)quinolin-4-yloxy)pentyloxy)-2-(hydroxymethyl)-4H-pyran-4-one 14

8-Trifluoromethyl-quinolin-4-ol (0.84 g, 2.88 mmol) was dissolved in DMF (5 mL). $Cs_2CO_3$ (0.98 g, 3.02 mmol) was added at room temperature and the mixture was stirred for 10 min. A solution of 5-(5-bromo-pentyloxy)-2-hydroxymethyl-pyran-4-one 10 (0.86 g, 3.02 mmol) in DMF (5 mL) was added via syringe. This mixture was stirred at 50° C. for 18 h. Water (10 mL) was added and the mixture extracted with EtOAc (2×50 mL), washed with water (3×50 mL), brine (3×50 mL) dried over $MgSO_4$, filtered and evaporated. The crude product was purified by column chromatography on silica using as eluent ($CH_2Cl_2$:MeOH)=90:10. 5-(5-(8-(Trifluoromethyl)quinolin-4-yloxy)pentyloxy)-2-(hydroxymethyl)-4H-pyran-4-one 14 was obtained (0.53 g, 35% yield) as a pale yellow foam.

The structure of compound 14 is presented below:

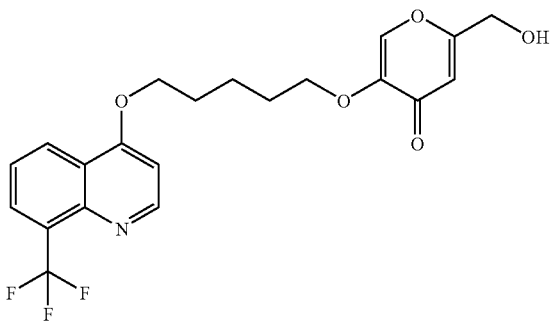

MW: 423.38; Yield: 35%; Pale yellow foam. Rf: 0.2 (CH$_2$Cl$_2$:MeOH=9:1). MS-ESI m/z (rel. Int.): 423.89 ([MH]$^+$, 55), 211 (100). HPLC: Method A, detection UV 254 nm, RT=4.60 min, peak area 87.9%.

5-(5-(quinazolin-4-yloxy)pentyloxy)-2-(hydroxymethyl)-4H-pyran-4-one 15

Quinazolin-4-ol (1.0 g, 6.84 mmol) was dissolved in DMF (7 mL). Cs$_2$CO$_3$ (2.23 g, 6.84 mmol) was added at RT and the mixture was stirred for 10 min. A solution of 5-(5-bromopentyloxy)-2-hydroxymethyl-pyran-4-one 10 (1.90 g, 6.52 mmol) in DMF (7 mL) was added via syringe. This mixture was stirred at 50° C. for 2 h. Water (150 mL) was added and the mixture extracted with EtOAc (2×100 mL), washed with water (3×100 mL), brine (3×100 mL), dried over MgSO$_4$, filtered and evaporated. The crude product was purified by column chromatography on silica using as eluent CH$_2$Cl$_2$:MeOH=95:5. 5-(5-(Quinazolin-4-yloxy)pentyloxy)-2-(hydroxymethyl)-4H-pyran-4-one 15 was obtained (0.61 g, 26% yield) as a pale yellow solid.

The structure of compound 15 is presented below:

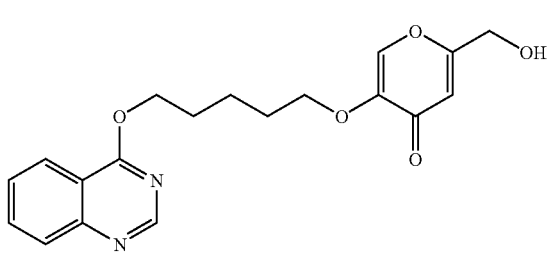

MW: 356.37; Yield: 26%; pale yellow solid; Mp: 117.7° C. Rf: 0.45 (CH$_2$Cl$_2$:MeOH=9:1). $^1$H-NMR (CDCl$_3$, d): 1.50-1.65 (m, 2H, CH$_2$), 1.80-1.95 (m, 4H, 2×CH$_2$), 3.78 (s, 1H, OH), 3.86 (t, 2H, J=6.2 Hz, —OCH$_2$), 4.03 (t, 2H, J=7.3 Hz, —OCH$_2$), 4.49 (d, J=6.2 Hz, 2H, CH$_2$—OH), 6.51 (s, 1H, —C=CH), 7.48-7.55 (m, 1H, ArH), 7.57 (s, 1H, —CH=C), 7.70-7.80 (m, 2H, ArH), 8.07 (s, 1H, N=CH=N), 8.30 (dd, 1H, J=8.0 Hz J=1.0 Hz, ArH).

Preparation of Intermediates Compounds 16-20

(5-(5-(6-(Trifluoromethyl)quinolin-4-yloxy)pentyloxy)-4-oxo-4H-pyran-2-yl)methyl methanesulfonate 16

To a solution of 5-(5-(6-(trifluoromethyl)quinolin-4-yloxy)pentyloxy)-2-(hydroxymethyl)-4H-pyran-4-one 11 (93 mg, 0.22 mmol) in CH$_2$Cl$_2$ (5 mL) was added at 0° C. triethylamine (37 μL, 0.26 mmol), methanesulfonyl chloride (20.5 μL, 0.26 mmol). The solution was stirred at RT for 1.5 h. Dichloromethane (50 mL) was added and the solution was washed with water (2×100 mL), dried over MgSO$_4$, filtered and evaporated. (5-(5-(6-(Trifluoromethyl)quinolin-4-yloxy)pentyloxy)-4-oxo-4H-pyran-2-yl)methyl methanesulfonate 16 was obtained (100 mg, 90.5% yield) as a pale yellow oil.

The structure of compound 16 is presented below:

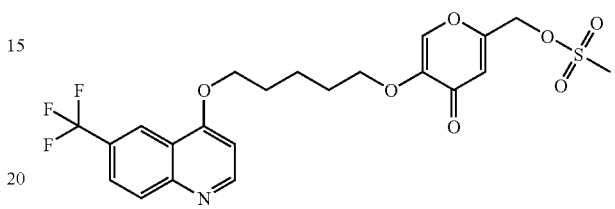

MW: 501.47; Yield: 90.5% (crude); Pale yellow oil. Rf: 0.6 (CH$_2$Cl$_2$:MeOH=90:10). $^1$H-NMR (CDCl$_3$, d): 1.70-1.81 (m, 2H, CH$_2$), 1.88-2.10 (m, 4H, 2×CH$_2$), 3.12 (s, 3H, CH$_3$), 3.95 (t, 2H, J=6.2 Hz, —CH$_2$—O), 4.25 (t, 2H, J=6.4 Hz, —O—CH$_2$), 4.99 (s, 2H, —CH$_2$—O), 6.52 (s, 1H, —CH=C), 6.84 (d, 1H, J=5.4 Hz, ArH), 7.62 (s, 1H, —CH=C), 7.87 (dd, 1H, J=8.8 Hz J=2.0 Hz, ArH), 8.14 (d, 1H, J=8.8 Hz, ArH), 8.51 (s, 1H, ArH), 8.85 (d, 1H, J=5.3 Hz, ArH). MS-ESI m/z (rel. Int.): 501.83 ([MH]$^+$, 80), 288.94 (100). HPLC: Method A, detection UV 254 nm, RT=4.65 min, peak area 81.2%.

(5-(5-(7-(Trifluoromethyl)quinolin-4-yloxy)pentyloxy)-4-oxo-4H-pyran-2-yl)methyl methanesulfonate 17

To a solution of 5-(5-(7-(trifluoromethyl)quinolin-4-yloxy)pentyloxy)-2-(hydroxymethyl)-4H-pyran-4-one 12 (240 mg, 0.57 mmol) in CH$_2$Cl$_2$ (15 mL) was added at 0° C. triethylamine (96 μL, 0.68 mmol), methanesulfonyl chloride (53 μL, 0.68 mmol). The solution was stirred at RT for 1.5 h. Dichloromethane (50 mL) was added and the solution was washed with water (3×100 mL), dried over MgSO$_4$, filtered and evaporated. (5-(5-(7-(trifluoromethyl)quinolin-4-yloxy)pentyloxy)-4-oxo-4H-pyran-2-yl)methyl methanesulfonate 17 was obtained (260 mg, 91% yield) as a crude yellow oil.

The structure of compound 17 is presented below:

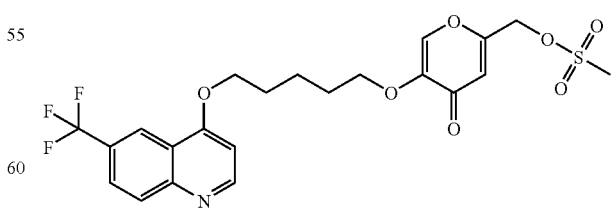

MW: 501.47; Yield: 91%; Yellow oil (crude product). Rf: 0.6 (CH$_2$Cl$_2$:MeOH=9:1). MS-ESI m/z (rel. Int.): 501.70 ([MH]$^+$, 100), 288.84 (80). HPLC: Method A, detection UV 254 nm, RT=4.57 min, peak area 94.0%.

4-[5-(6-Methanesulfonyloxymethyl-4-oxo-4H-pyran-3-yloxy)pentyloxy]-7-trifluoromethyl-quinoline-3-carboxylic acid ethyl ester 18

To a solution of 4-[5-(6-hydroxymethyl-4-oxo-4H-pyran-3-yloxy)-pentyloxy]-7-trifluoromethyl-quinoline-3-carboxylic acid ethyl ester 13 (330 mg, 0.67 mmol) in CH$_2$Cl$_2$ (15 mL) was added at 0° C. triethylamine (37 µL, 0.26 mmol), methanesulfonyl chloride (62 µL, 0.80 mmol). The solution was stirred at RT for 1 h. Dichloromethane (50 mL) was added and the solution was washed with water (2×100 mL), dried over MgSO$_4$, filtered and evaporated. The crude product was purified by column chromatography on silica using as eluent CH$_2$Cl$_2$:MeOH=95:15. (5-(5-(6-(Trifluoromethyl)quinolin-4-yloxy)pentyloxy)-4-oxo-4H-pyran-2-yl)methyl-methanesulfonate 18 was obtained (246 mg, 65% yield) as a pale yellow oil.

The structure of compound 18 is presented below:

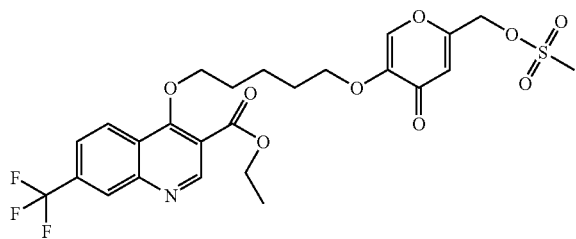

MW: 573.54; Yield: 65%; Pale yellow foam. Rf: 0.5 (CH$_2$Cl$_2$:MeOH=9:1). MS-ESI m/z (rel. Int.): 573.79 ([MH]$^+$, 100), 527.70 (30). HPLC: Method A, detection UV 254 nm, RT=5.38 min, peak area 60.1%.

(5-(5-(8-(Trifluoromethyl)quinolin-4-yloxy)pentyloxy)-4-oxo-4H-pyran-2-yl)methyl methanesulfonate 19

To a solution of 5-(5-(8-(trifluoromethyl)quinolin-4-yloxy)pentyloxy)-2-(hydroxymethyl)-4H-pyran-4-one 14 (430 mg, 1.02 mmol) in CH$_2$Cl$_2$ (15 mL) was added at 0° C. triethylamine (173 µL, 1.21 mmol), methanesulfonyl chloride (95 µL, 1.21 mmol). The solution was stirred at RT for 1 h. Dichloromethane (50 mL) was added and the solution was washed with water (2×100 mL), dried over MgSO$_4$, filtered and evaporated. The crude product was purified by column chromatography on silica using as eluent (CH$_2$Cl$_2$:MeOH)=95:05. (5-(5-(8-(Trifluoromethyl)quinolin-4-yloxy)pentyloxy-4-oxo-4H-pyran-2-yl)methyl methanesulfonate 19 was obtained (188 mg, 37% yield) as a pale yellow oil.

The structure of compound 19 is presented below:

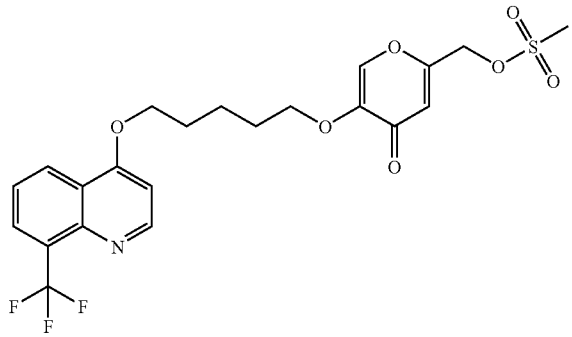

MW: 501.47; Yield: 37%; Pale yellow oil. Rf: 0.3 (CH$_2$Cl$_2$:MeOH=95:05). MS-ESI m/z (rel. Int.): 501.77 ([MH]$^+$, 95), 288.91 (100). HPLC: Method A, detection UV 254 nm, RT=5.06 min, peak area 63.1%.

(5-(5-(Quinazolin-4-yloxy)pentyloxy)-4-oxo-4H-pyran-2-yl)methyl methanesulfonate 20

To a solution of 5-(5-(quinazolin-4-yloxy)pentyloxy)-2-(hydroxymethyl)-4H-pyran-4-one 15 (0.53 g, 1.49 mmol) in CH$_2$Cl$_2$ (20 mL) was added at 0° C. triethylamine (252 µL, 1.78 mmol), methanesulfonyl chloride (138 µL, 1.78 mmol). The solution was stirred at RT for 1 h. Dichloromethane (50 mL) was added and the solution was washed with water (2×100 mL), dried over MgSO$_4$, filtered and evaporated. (5-(5-(Quinazolin-4-yloxy)pentyloxy)-4-oxo-4H-pyran-2-yl) methyl methanesulfonate 20 was obtained (0.64 g, 99% yield) as a pale yellow oil.

The structure of compound 20 is presented below:

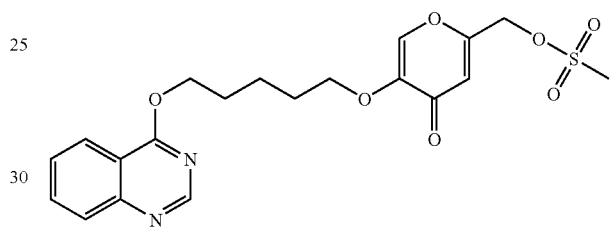

MW: 434.46; Yield: 99% (crude); Yellow oil. Rf: 0.3 (CH$_2$Cl$_2$:MeOH=95:05). $^1$H-NMR (CDCl$_3$, d): 1.55-1.70 (m, 2H, CH$_2$), 1.80-1.88 (m, 4H, 2×CH$_2$), 3.11 (s, 3H, CH$_3$), 3.88 (t, 2H, J=6.2 Hz, —CH$_2$—O), 4.04 (t, 2H, J=7.3 Hz, —O—CH$_2$), 4.99 (s, 2H, —CH$_2$—O), 6.52 (s, 1H, —CH═C), 7.51 (t, 1H, J=8.0 Hz, ArH), 7.61 (s, 1H, —CH═C), 7.70-7.83 (m, 2H, ArH), 8.09 (s, 1H, ArH), 8.31 (d, 1H, J=8.0 Hz, ArH).

Preparation of EHT 9317, EHT 5430 and EHT 7370

Example 17

5-(5-(7-(Trifluoromethyl)quinolin-4-ylthio)pentyloxy)-2-((piperidin-1-yl)methyl)-4H-pyran-4-one (EHT 9317)

Methanesulfonic acid 4-oxo-5-[5-(7-trifluoromethyl-quinolin-4-ylsulfanyl)-pentyloxy]-4H-pyran-2-ylmethyl ester 9 (100 mg, 0.193 mmol) was dissolved in dichloromethane (3 mL). Piperidine (48 µL, 0.483 mmol) was added via syringe. The mixture was stirred at 45° C. for 1.25 h. The solution was evaporated to dryness and CH$_2$Cl$_2$ added (50 ml). The solution was washed with aqueous NaHCO$_3$ 5% (3×50 mL) and brine (2×20 mL). The organic layer was dried over MgSO$_4$, filtered and evaporated. The crude product was purified by column chromatography oh silica using as eluent CH$_2$Cl$_2$:MeOH=98:02. 5-(5-(7-(Trifluoromethyl)quinolin-4-ylthio)pentyloxy)-2-((piperidin-1-yl)methyl)-4H-pyran-4-one EHT 9317 was obtained (86 mg, 88% yield) as a beige solid.

69

The structure of compound ex 17 is presented below:

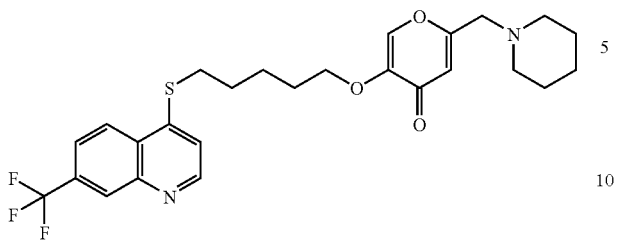

MW: 506.59; Yield: 88%; Beige solid; Mp: 108.9° C. $R_f$: 0.4 (CH$_2$Cl$_2$:MeOH=98:02). $^1$H-NMR (CDCl$_3$, δ): 1.21-1.46 (m, 2H, CH$_2$), 1.57-1.62 (m, 4H, 3×CH$_2$), 1.69-1.76 (m, 2H, CH$_2$), 1.86-1.92 (m, 4H, 2×CH$_2$ ), 2.43 (t, 4H, J=4.6 Hz, —CH$_2$N), 3.15 (t, 2H, J=7.2 Hz, —SCH$_2$), 3.32 (s, 2H, —CH$_2$N), 3.89 (t, 2H, J=6.2 Hz, O—CH$_2$), 6.44 (s, 1H, —C═CH), 7.58 (s, 1H, —CH═C), 7.71 (dd, 1H, J=1.6 Hz, J=8.8 Hz, ArH), 8.25 (d, 1H, J=8.8 Hz, ArH), 8.36 (s, 1H, ArH), 8.79 (d, 1H, J=4.8 Hz, ArH). MS-ESI m/z (rel. Int.): 507.0 ([MH]$^+$, 100). HPLC: Method A, detection UV 254 nm, EHT 9317 RT=4.36 min, peak area 93.7%.

Example 18

5-(5-(7-(Trifluoromethyl)quinolin-4-ylthio)pentyloxy)-2-(thiomorpholino-methyl)-4H-pyran-4-one (EHT 5430)

Methanesulfonic acid 4-oxo-5-[5-(7-trifluoromethyl-quinolin-4-ylsulfanyl)-pentyloxy]-4H-pyran-2-ylmethyl ester 9 (100.0 mg, 0.193 mmol) was dissolved in dichloromethane (3 mL). Thiomorpholine (46 µL, 0.483 mmol) was added via syringe. The mixture was stirred at 45° C. for 2.5 h. The solution was evaporated to dryness and CH$_2$Cl$_2$ added (50 ml). This solution was washed with aqueous NaHCO$_3$ 5% (3×50 mL) and brine (2×20 mL). The organic layer was dried over MgSO$_4$, filtered and evaporated. The crude product was purified by column chromatography on silica using as eluent CH$_2$Cl$_2$:MeOH=98:02. 5-(5-(7-(Trifluoromethyl)quinolin-4-ylthio)pentyloxy)-2-(thiomorpholinomethyl)-4H-pyran-4-one EHT 5430 was obtained (65 mg, 64% yield) as a beige solid.

The structure of compound ex 18 is presented below:

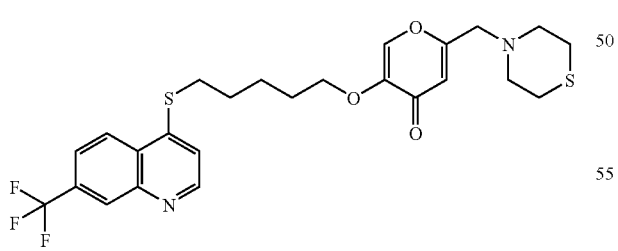

MW: 524.63; Yield: 64%; Beige solid; Mp: 105.7° C. Rf: 0.4 (CH$_2$Cl$_2$:MeOH=98:02). $^1$H-NMR (CDCl$_3$, δ): 1.63-1.74 (m, 2H, CH$_2$), 1.88-1.92 (m, 4H, CH$_2$), 2.69-2.78 (m, 8H, CH$_2$—N & CH$_2$—S), 3.15 (t, 2H, J=7.2 Hz, —SCH$_2$), 3.38 (s, 2H, —CH$_2$N), 3.89 (t, 2H, J=6.2 Hz, —CH$_2$O), 6.45 (s, 1H, —CH═C), 7.56 (s, 1H, —CH═C), 7.71 (dd, 1H, J=1.4 Hz, J=8.8 Hz, ArH), 8.25 (d, 1H, J=8.8 Hz, ArH), 8.36 (s, 1H, ArH), 8.79 (d, 1H, J=4.5 Hz, ArH). MS-ESI m/z (rel. Int.): 525 ([MH]$^+$, 100). HPLC: Method A, detection UV 254 nm, EHT 5430 RT=4.39 min, peak area 92.5%.

Example 19

2-((Diethylamino)methyl)-5-(5-(7-(trifluoromethyl) quinolin-4-ylthio)pentyloxy)-4H-pyran-4-one (EHT 7370)

Methanesulfonic acid 4-oxo-5-[5-(7-trifluoromethyl-quinolin-4-ylsulfanyl)-pentyloxy]-4H-pyran-2-ylmethyl ester 9 (100 mg, 0.193 mmol) was dissolved in dichloromethane (3 mL). Diethylamine (50 µL, 0.483 mmol) was added via syringe. The mixture was stirred at 45° C. for 3.5 h. The solution was evaporated to dryness and CH$_2$Cl$_2$ added (50 ml). This solution was washed with aqueous NaHCO$_3$ 5% (3×50 mL) and brine (2×20 mL). The organic layer was dried over MgSO$_4$, filtered and evaporated. The crude product was purified by column chromatography on silica using as eluent CH$_2$Cl$_2$:MeOH=98:02. 2-((Diethylamino)methyl)-5-(5-(7-(trifluoromethyl)quinolin-4-ylthio)pentyloxy)-4H-pyran-4-one EHT 7370 was obtained (46 mg, 48% yield) as a white solid.

The structure of compound ex 19 is presented below:

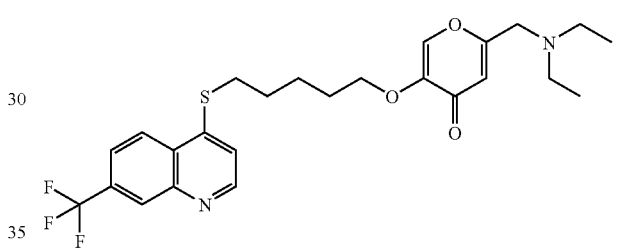

MW: 494.58; Yield: 48%; White solid; Mp: 71.2° C. Rf: 0.5 (CH$_2$Cl$_2$:MeOH=98:02). $^1$H-NMR (CDCl$_3$, δ): 1.05 (t, 6H, J=7.2 Hz, 2×CH$_3$), 1.65-1.75 (m, 2H, 2×CH$_2$), 1.88-1.93 (m, 4H, 2×CH$_2$), 2.58 (q, J=7.2 Hz, 2×CH$_2$), 3.16 (t, 2H, J=7.2 Hz, —SCH$_2$), 3.43 (s, 2H, —CH$_2$N), 3.89 (t, 2H, J=6.2 Hz, —CH$_2$O), 6.47 (s, 1H, —C═CH), 7.57 (s, 1H, —C═CH), 7.71 (d, 1H, J=8.8 Hz, ArH), 8.25 (d, 1H, J=8.8 Hz, ArH), 8.36 (s, 1H, ArH), 8.79 (d, 1H, J=4.5 Hz, ArH). MS-ESI m/z (rel. Int.): 495 ([MH]$^+$, 100). HPLC: Method A, detection UV 254 nm, EHT 7370 RT=4.29 min, peak area 89.0%.

Preparation of EHT 1426, EHT 0079, EHT 3411, EHT 8791, EHT 8935, EHT 5847, EHT 4867, EHT 5317, EHT 3726 and EHT 4063

Example 20

5-(5-(6-(Trifluoromethyl)quinolin-4-yloxy)pentyloxy)-2-(morpholinomethyl)-4H-pyran-4-one (EHT 1426)

Methanesulfonic acid 4-oxo-5-[5-(7-trifluoromethyl-quinolin-4-yloxy)-pentyloxy]-4H-pyran-2-ylmethyl ester 16 (100 mg, 0.20 mmol) was dissolved in dichloromethane (5 mL). Morpholine (44 µL, 0.50 mmol) was added via syringe. The mixture was stirred at 45° C. for 18 h. After cooling to room temperature CH$_2$Cl$_2$ (75 ml) was added and the mixture was washed with NaHCO$_3$ 10% (3×50 mL) and brine (3×50 mL). The organic layer was dried over MgSO$_4$, filtered and evaporated. The crude product was purified by column chromatography on silica using as eluent CH$_2$Cl$_2$:MeOH=9:1. 5-(5-(6-(Trifluoromethyl)quinolin-4-yloxy)pentyloxy)-2-(morpholinomethyl)-4H-pyran-4-one EHT 1426 was obtained (37 mg, 35% yield) as an orange oil.

The structure of compound ex 20 is presented below:

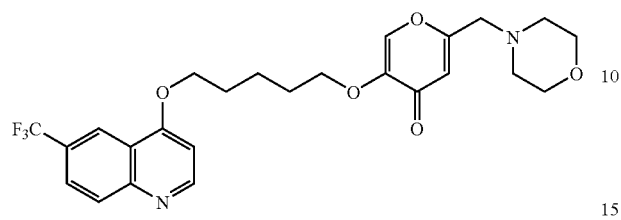

MW: 492.50; Yield: 35%; Orange oil. Rf: 0.8 (CH$_2$Cl$_2$:MeOH=90:10). $^1$H-NMR (CDCl$_3$, d): 1.65-1.83 (m, 2H, CH$_2$), 1.90-2.10 (m, 4H, 2×CH$_2$), 2.40-2.60 (m, 4H, 2×CH$_2$N—), 3.36 (s, 2H, —NCH$_2$), 3.55-3.80 (m, 4H, 2×CH$_2$O), 3.94 (t, 2H, J=6.3 Hz, —OCH$_2$), 4.25 (t, 2H, J=6.3 Hz, —CH$_2$O), 6.47 (s, 1H, —C=CH), 6.82 (d, 1H, J=5.2 Hz, ArH), 7.60 (s, 1H, —C=CH), 7.86 (dd, 1H, J=8.8 Hz J=2.0 Hz, ArH), 8.12 (d, J=8.8 Hz, 1H, ArH), 8.50 (s, 1H, ArH), 8.84 (d, 1H, J=5.2 Hz, ArH). MS-ESI m/z (rel. Int.): 492.83 ([MH]$^+$, 35), 279.97 (65), 213.88 (100). HPLC: Method A, detection UV 254 nm, EHT 1426 RT=3.94 min, peak area 86.0%.

Example 21

5-(5-(7-(Trifluoromethyl)quinolin-4-yloxy)pentyloxy)-2-((4-methylpiperazin-1-yl)methyl)-4H-pyran-4-one (EHT 0079)

Methanesulfonic acid 4-oxo-5-[5-(7-trifluoromethyl-quinolin-4-yloxy)-pentyloxy]-4H-pyran-2-ylmethyl ester 17 (130 mg, 0.26 mmol) was dissolved in dichloromethane (5 mL). 1-Methyl-piperazine (75 µL, 0.67 mmol) was added via syringe. The mixture was stirred at 45° C. for 3 h. After cooling to room temperature CH$_2$Cl$_2$ (75 ml) was added and the mixture was washed with NaHCO$_3$ 10% (3×50 mL) and brine (3×50 mL). The organic layer was dried over MgSO$_4$, filtered and evaporated. The crude product was purified by column chromatography on silica using as eluent CH$_2$Cl$_2$:MeOH=9:1. 5-(5-(7-(Trifluoromethyl)quinolin-4-yloxy)pentyloxy)-2-((4-methylpiperazin-1-yl)methyl)-4H-pyran-4-one EHT 0079 was obtained (30 mg, 23% yield) as a yellow oil.

The structure of compound ex 21 is presented below:

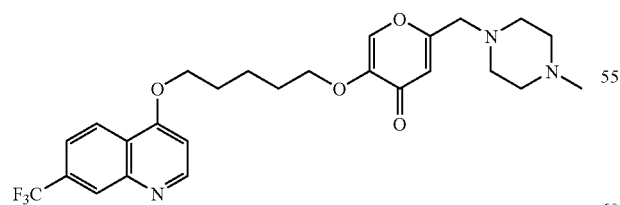

MW: 505.53; Yield: 23%; Yellow oil. Rf: 0.4 (CH$_2$Cl$_2$:MeOH=90:10). $^1$H-NMR (CDCl$_3$, d): 1.68-1.83 (m, 2H, CH$_2$), 1.90-2.10 (m, 4H, 2×CH$_2$), 2.31 (s, 3H, Me), 2.30-2.75 (m, 8H, 4×-NCH$_2$), 3.38 (s, 2H, —NCH$_2$), 3.93 (t, 2H, J=6.2 Hz, —OCH$_2$), 4.25 (t, 2H, J=6.3 Hz, —CH$_2$O), 6.46 (s, 1H, —C=CH), 6.82 (d, 1H, J=5.3 Hz, ArH), 7.59 (s, 1H, —C=CH), 7.67 (d, 1H, J=8.8 Hz, ArH), 8.32 (s, 1H, ArH), 8.33 (d, J=8.8 Hz, 1H, ArH), 8.82 (d, 1H, J=5.3 Hz, ArH). MS-ESI m/z (rel. Int.): 505.85 ([MH]$^+$, 55), 293 (25), 213.86 (100). HPLC: Method A, detection UV 254 nm, EHT 0079 RT=3.94 min, peak area 95.0%.

Example 22

5-(5-(7-(Trifluoromethyl)quinolin-4-yloxy)pentyloxy)-2-(morpholinomethyl)-4H-pyran-4-one (EHT 3411)

Methanesulfonic acid 4-oxo-5-[5-(7-trifluoromethyl-quinolin-4-yloxy)-pentyloxy]-4H-pyran-2-ylmethyl ester 17 (130 mg, 0.259 mmol) was dissolved in dichloromethane (5 mL). Morpholine (58 µL, 0.66 mmol) was added via syringe. The mixture was stirred at 45° C. for 5 h. After cooling to room temperature CH$_2$Cl$_2$ (75 ml) was added and the mixture was washed with NaHCO$_3$ 10% (3×50 mL) and brine (3×50 mL). The organic layer was dried over MgSO$_4$, filtered and evaporated. The crude product was purified by column chromatography on silica using as eluent CH$_2$Cl$_2$:MeOH=9:1. 5-(5-(7-(Trifluoromethyl)quinolin-4-yloxy)pentyloxy)-2-(morpholinomethyl)-4H-pyran-4-one_EHT 3411 was obtained (24 mg, 19% yield) as a colourless oil.

The structure of compound ex 22 is presented below:

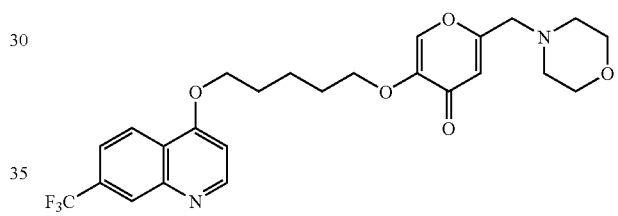

MW: 492.4; Yield: 19%; Colourless oil. Rf: 0.3 (CH$_2$Cl$_2$:MeOH=90:10). $^1$H-NMR (CDCl$_3$, d): 1.68-1.83 (m, 2H, CH$_2$), 1.90-2.10 (m, 4H, 2×CH$_2$), 2.52 (t, 4H, J=4.7 Hz, 2×-NCH$_2$), 3.37 (s, 2H, —NCH$_2$), 3.73 (t, 2H, J=4.7 Hz, 2×-NCH$_2$), 3.93 (t, 2H, J=6.3 Hz, —OCH$_2$), 4.25 (t, 2H, J=6.3 Hz, —CH$_2$O), 6.47 (s, 1H, —C=CH), 6.82 (d, 1H, J=5.2 Hz, ArH), 7.59 (s, 1H, —C=CH), 7.66 (dd, 1H, J=8.8 Hz J=1.5 Hz, ArH), 8.32 (s, 1H, ArH), 8.34 (d, J=8.8 Hz, 1H, ArH), 8.89 (d, 1H, J=5.2 Hz, ArH). MS-ESI m/z (rel. Int.): 492.83 ([MH]$^+$, 70), 280 (85), 213.87 (100). HPLC: Method A, detection UV 254 nm, EHT 3411 RT=3.93 min, peak area 99.9%.

Example 23

4-[5-(6-(4-Methyl-piperazin-1-ylmethyl)-4-oxo-4H-pyran-3-yloxy)-pentyloxy]-7-trifluoromethyl-quinoline-3-carboxylic acid ethyl ester (EHT 8791)

Methanesulfonic acid 4-oxo-5-[5-(7-trifluoromethyl-quinolin-4-yloxy)-pentyloxy]-4H-pyran-2-ylmethyl ester 18 (123 mg, 0.215 mmol) was dissolved in dichloromethane (5 mL). 1-Methyl-piperazine (60 µL, 0.54 mmol) was added via syringe. The mixture was stirred at 45° C. for 2 h. After cooling to room temperature CH$_2$Cl$_2$ (75 ml) was added and the mixture was washed with NaHCO$_3$ 10% (3×50 mL) and brine (3×50 mL). The organic layer was dried over MgSO$_4$, filtered and evaporated. The crude product was purified by column chromatography on silica using as eluent CH$_2$Cl$_2$:

MeOH=9:1. 4-[5-(6-(4-Methyl-piperazin-1-ylmethyl)-4-oxo-4H-pyran-3-yloxy)-pentyloxy]-7-trifluoromethyl-quinoline-3-carboxylic acid ethyl ester EHT 8791 was obtained (38 mg, 31% yield) as a yellow oil.

The structure of compound ex 23 is presented below:

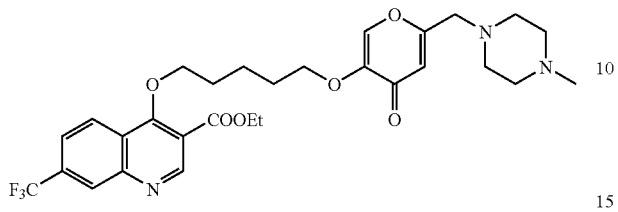

MW: 577.61; Yield: 31%; Yellow oil. Rf: 0.30 (CH$_2$Cl$_2$:MeOH=90:10). $^1$H-NMR (CDCl$_3$, d): 1.43 (t, 3H, J=7.1 Hz, CH$_3$), 1.57-1.71 (m, 2H, CH$_2$), 1.84-2.08 (m, 4H, 2×CH$_2$), 2.32 (s, 3H, —NCH$_3$), 2.40-2.68 (m, 8H, 4×CH$_2$N—), 3.39 (s, 2H, —NCH$_2$), 3.89 (t, 2H, J=5.9 Hz, —OCH$_2$), 4.27 (t, 2H, J=7.3 Hz, —CH$_2$O), 4.42 (q, 2H, J=7.1 Hz, —OCH$_2$), 6.46 (s, 1H, —C=CH), 7.58 (s, 1H, —C=CH), 7.66 (d, 1H, J=8.3 Hz, ArH), 7.70 (m, 1H, ArH), 8.55 (s, 1H, ArH), 8.67 (d, 1H, J=8.3 Hz, ArH). MS-ESI m/z (rel. Int.): 577.88 ([MH]$^+$, 100), 287.07 (25), 266.55 (35). HPLC: Method A, detection UV 254 nm, EHT 8791 RT=4.46 min, peak area 97.6%.

Example 24

4-[5-(6-Morpholin-4-ylmethyl-4-oxo-4H-pyran-3-yloxy)-pentyloxy]-7-trifluoromethyl-quinoline-3-carboxylic acid ethyl ester (EHT 8935)

4-[5-(6-Methanesulfonyloxymethyl-4-oxo-4H-pyran-3-yloxy)-pentyloxy]-7-trifluoromethyl-quinoline-3-carboxylic acid ethyl ester 18 (123 mg, 0.214 mmol) was dissolved in dichloromethane (3 mL). Morpholine (47.3 µL, 0.537 mmol) was added via syringe. The mixture was stirred at 45° C. for 3 h. CH$_2$Cl$_2$ (50 ml) was added and the solution was washed with NaHCO$_3$ 10% (3×50 mL) and brine (3×50 mL). The organic layer was dried over MgSO$_4$, filtered and evaporated. The crude product was purified by column chromatography on silica using as eluent CH$_2$Cl$_2$:MeOH=95:05. 4-[5-(6-Morpholin-4-ylmethyl-4-oxo-4H-pyran-3-yloxy)-pentyloxy]-7-trifluoromethyl-quinoline-3-carboxylic acid ethyl ester EHT 8935 was obtained (66 mg, 55%) as a colourless oil.

The structure of compound ex 24 is presented below:

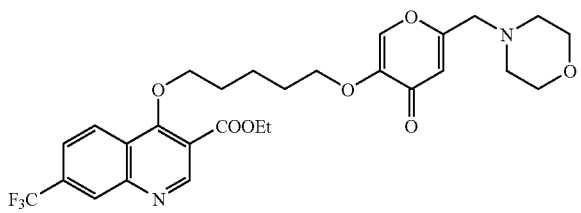

MW: 564.56; Yield: 55%; Colourless oil. Rf: 0.25 (CH$_2$Cl$_2$:MeOH=95:05). $^1$H-NMR (CDCl$_3$, d): 1.43 (t, 3H, J=7.1 Hz, CH$_3$), 1.57-1.71 (m, 2H, CH$_2$), 1.84-2.08 (m, 4H, 2×CH$_2$), 2.52 (t, 4H, J=4.5 Hz, CH$_2$—N—CH$_2$), 3.37 (s, 2H, —NCH$_2$), 3.73 (t, 4H, J=4.7 Hz, CH$_2$—O—CH$_2$), 3.89 (t, 2H, J=5.9 Hz, —OCH$_2$), 4.27 (t, 2H, J=7.6 Hz, —CH$_2$O), 4.42 (q, 2H, J=7.1 Hz, —OCH$_2$), 6.47 (s, 1H, —C=CH), 7.59 (s, 1H, —C=CH), 7.63-7.72 (m, 2H, ArH), 8.55 (s, 1H, ArH), 8.67 (d, 1H, J=8.3 Hz, ArH). MS-ESI m/z (rel. Int.): 565 ([MH]$^+$, 100), 260 (30). HPLC: Method A, detection UV 254 nm, EHT 8935 RT=4.46 min, peak area 98.0%.

Example 25

5-(5-(8-(Trifluoromethyl)quinolin-4-yloxy)penty-loxy)-2-((4-methylpiperazin-1-yl)methyl)-4H-pyran-4-one (EHT 5847)

Methanesulfonic acid 4-oxo-5-[5-(8-trifluoromethyl-quinolin-4-yloxy)-pentyloxy]-4H-pyran-2-ylmethyl ester 19 (94 mg, 0.187 mmol) was dissolved in dichloromethane (5 mL). 1-Methyl-piperazine (52 µL, 0.47 mmol) was added via syringe. The mixture was stirred at 45° C. for 1 h. CH$_2$Cl$_2$ (75 ml) was added and the solution washed with NaHCO$_3$ 10% (3×50 mL) and brine (3×50 mL). The organic layer was dried over MgSO$_4$, filtered and evaporated. The crude product was purified by column chromatography on silica using as eluent CH$_2$Cl$_2$:MeOH=9:1. 5-(5-(8-(Trifluoromethyl)quinolin-4-yloxy)pentyloxy)-2-((4-methylpiperazin-1-yl)methyl)-4H-pyran-4-one EHT 5847 was obtained (13.6 mg, 15% yield) as a white foam.

The structure of compound ex 25 is presented below:

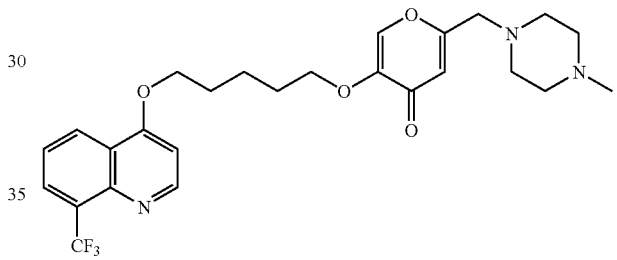

MW: 505.44; Yield: 15%; White foam. Rf: 0.4 (CH$_2$Cl$_2$:MeOH=90:10). $^1$H-NMR (CDCl$_3$, d): 1.58-1.81 (m, 2H, CH$_2$), 1.90-2.05 (m, 4H, 2×CH$_2$), 2.31 (s, 3H, —NCH$_3$), 2.30-2.75 (m, 8H, 4×CH$_2$N—), 3.37 (s, 2H, —NCH$_2$), 3.92 (t, 2H, J=6.2 Hz, —OCH$_2$), 4.24 (t, 2H, J=6.2 Hz, —CH$_2$O), 6.45 (s, 1H, —C=CH), 6.82 (d, 1H, J=5.2 Hz, ArH), 7.50-7.60 (m, 2H, ArH and —C=CH), 8.06 (d, 1H, J=7.3 Hz, ArH), 8.44 (d, 1H, J=8.6 Hz, ArH), 8.89 (d, 1H, J=5.2 Hz, ArH). MS-ESI m/z (rel. Int.): 505.86 ([MH]$^+$, 95), 293 (70), 213.86 (100), 193.85 (80). HPLC: Method A, detection UV 254 nm, EHT 5847 RT=4.05 min, peak area 94.7%.

Example 26

5-(5-(8-(Trifluoromethyl)quinolin-4-yloxy)penty-loxy)-2-(morpholinomethyl)-4H-pyran-4-one (EHT 4687)

Methanesulfonic acid 4-oxo-5-[5-(8-trifluoromethyl-quinolin-4-yloxy)-pentyloxy]-4H-pyran-2-ylmethyl ester 19 (94 mg, 0.187 mmol) was dissolved in dichloromethane (4 mL). Morpholine (41 µL, 0.47 mmol) was added via syringe. The mixture was stirred at 45° C. for 3 h. CH$_2$Cl$_2$ (75 ml) was added and the solution washed with NaHCO$_3$ 10% (3×50 mL) and brine (3×50 mL). The organic layer was dried over MgSO$_4$, filtered and evaporated. The crude product was purified by column chromatography on silica using as eluent CH$_2$Cl$_2$:MeOH=95:5. 5-(5-(8-(Trifluoromethyl)quinolin-4- yloxy)pentyloxy)-2-(morpholinomethyl)-4H-pyran-4-one EHT 4687 was obtained (46 mg, 50% yield) as a white foam.

The structure of compound ex 26 is presented below:

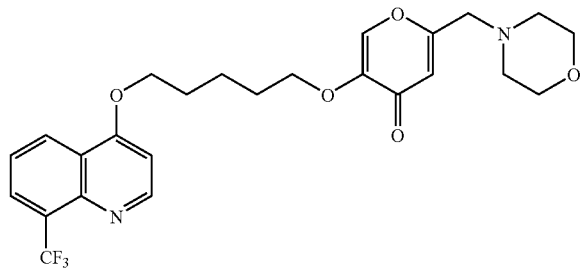

MW: 492.50; Yield: 50%; White foam. Rf: 0.3 (CH$_2$Cl$_2$:MeOH=95:5). $^1$H-NMR (CDCl$_3$, d): 1.68-1.82 (m, 2H, CH$_2$), 1.90-2.10 (m, 4H, 2×CH$_2$), 2.50 (m, 4H, 2×CH$_2$N—), 3.36 (s, 2H, —NCH$_2$), 3.73 (m, 4H, —CH$_2$O), 3.93 (t, 2H, J=6.2 Hz, —OCH$_2$), 4.25 (t, 2H, J=6.2 Hz, —CH$_2$O), 6.47 (s, 1H, —C=CH), 6.82 (d, 1H, J=5.2 Hz, ArH), 7.50-7.60 (m, 2H, ArH and —C=CH), 8.06 (d, 1H, J=7.3 Hz, ArH), 8.44 (d, 1H, J=8.6 Hz, ArH), 8.89 (d, 1H, J=5.2 Hz, ArH). MS-ESI m/z (rel. Int.): 492.83 ([MH]$^+$, 50), 279.97 (100), 213.86 (35), 193.88 (50). HPLC: Method A, detection UV 254 nm, EHT 4687 RT=4.13 min, peak area 94.4%.

Example 27

5-(5-(Quinazolin-4-yloxy)pentyloxy)-2-((pyrrolidin-1-yl)methyl)-4H-pyran-4-one (EHT 5317)

Methanesulfonic acid 4-oxo-5-[5-(quinazolin-4-yloxy)pentyloxy]-4H-pyran-2-ylmethyl ester 20 (100 mg, 0.23 mmol) was dissolved in dichloromethane (3 mL). Pyrrolidine (48 µL, 0.575 mmol) was added via syringe. The mixture was stirred at 45° C. for 1.5 h. .CH$_2$Cl$_2$ (75 ml) was added and the solution was washed with NaHCO$_3$ 10% (3×50 mL), brine (3×50 mL). The organic layer was dried over MgSO$_4$, filtered and evaporated. The crude product was purified by column chromatography on silica using as eluent CH$_2$Cl$_2$:MeOH=90:10. 5-(5-(Quinazolin-4-yloxy)pentyloxy)-2-((pyrrolidin-1-yl)methyl)-4H-pyran-4-one EHT 5317 was obtained (30 mg, 35% yield) as a colourless oil.

The structure of compound ex 27 is presented below:

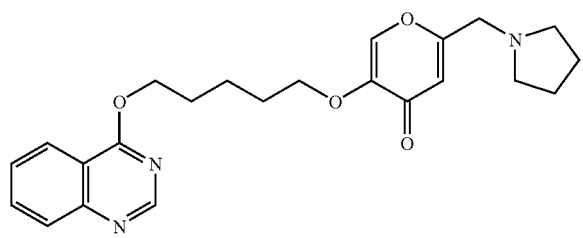

MW: 409.44; Yield: 32%; Colourless oil. Rf: 0.4 (CH$_2$Cl$_2$:MeOH=90:10). $^1$H-NMR (CDCl$_3$, d): 1.55-1.63 (m, 2H, CH$_2$), 1.82-1.93 (m, 4H, 2×CH$_2$), 2.54 (t, 4H, J=4.6 Hz, 2×CH$_2$), 3.38 (s, 2H, —NCH$_2$), 3.74 (t, 4H, J=4.6 Hz, 2×CH$_2$N—), 3.87 (t, 2H, J=6.3 Hz, —OCH$_2$), 4.03 (t, 2H, J=7.3 Hz, —CH$_2$O), 6.47 (s, 1H, —C=CH), 7.48-7.55 (m, 1H, ArH), 7.57 (s, 1H, —C=CH), 7.69-7.80 (m, 2H, ArH), 8.07 (s, 1H, —N=CH=N—), 8.31 (d, 1H, J=8.0 Hz, ArH).

MS-ESI m/z (rel. Int.): 409.97 ([MH]$^+$, 100), 147 (55). HPLC: Method A, detection UV 254 nm, EHT 5317 RT=3.86 min, peak area 90.0%.

Example 28

5-(5-(Quinazolin-4-yloxy)pentyloxy)-2-(morpholinomethyl)-4H-pyran-4-one (EHT 3726)

Methanesulfonic acid 4-oxo-5-[5-(quinazolin-4-yloxy)pentyloxy]-4H-pyran-2-ylmethyl ester 20 (100 mg, 0.23 mmol) was dissolved in dichloromethane (3 mL). Morpholine (51 µL, 0.575 mmol) was added via syringe. The mixture was stirred at 45° C. for 1 h. CH$_2$Cl$_2$ (50 ml) was added and the solution washed with NaHCO$_3$ 10% (3×50 mL) and brine (3×50 mL). The product was extracted with CH$_2$Cl$_2$ (5×50 mL). The organic layer was dried over MgSO$_4$, filtered and evaporated. The crude product was purified by column chromatography on silica using as eluent CH$_2$Cl$_2$:MeOH=99:01. 5-(5-(Quinazolin-4-yloxy)pentyloxy)-2-(morpholinomethyl)-4H-pyran-4-one EHT 3726 was obtained (8.2 mg, 8.5%) as a white solid.

The structure of compound ex 28 is presented below:

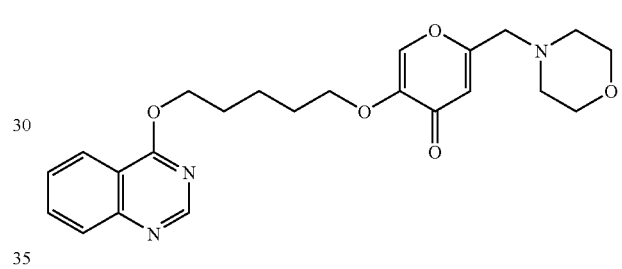

MW: 425.48; Yield: 8.5%; White solid. Rf: 0.4 (CH$_2$Cl$_2$:MeOH=99:01). $^1$H-NMR (CDCl$_3$, d): 1.55-1.63 (m, 2H, CH$_2$), 1.82-1.93 (m, 4H, 2×CH$_2$), 2.52 (t, 4H, J=4.6 Hz, 2×CH$_2$N—), 3.38 (s, 2H, —NCH$_2$), 3.73 (t, 4H, J=4.6 Hz, 2×CH$_2$O—), 3.87 (t, 2H, J=6.3 Hz, —OCH$_2$), 4.04 (t, 2H, J=7.3 Hz, —CH$_2$O), 6.46 (s, 1H, —C=CH), 7.48-7.55 (m, 1H, ArH), 7.57 (s, 1H, —C=CH), 7.69-7.80 (m, 2H, ArH), 8.06 (s, 1H, —N=CH=N—), 8.31 (dd, 1H, J=7.8 Hz J=0.8 Hz, ArH). MS-ESI m/z (rel. Int.): 425.9 ([MH]$^+$, 100). HPLC: Method A, detection UV 254 nm, EHT 3726 RT=3.86 min, peak area 97.6%.

Example 29

5-(5-(Quinazolin-4-yloxy)pentyloxy)-2-((4-methylpiperazin-1-yl)methyl)-4H-pyran-4-one (EHT 4063)

Methanesulfonic acid 4-oxo-5-[5-(quinazolin-4-yloxy)pentyloxy]-4H-pyran-2-ylmethyl ester 20 (100 mg, 0.23 mmol) was dissolved in dichloromethane (3 mL). 1-Methylpiperazine (64 µL, 0.575 mmol) was added via syringe. The mixture was stirred at 45° C. for 1 h. CH$_2$Cl$_2$ (50 ml) was added and the solution was washed with NaHCO$_3$ 10% (3×50 mL) and brine (3×50 mL). The product was extracted with CH$_2$Cl$_2$ (5×50 mL). The organic layer was dried over MgSO$_4$, filtered and evaporated. The crude product was purified by column chromatography on silica using as eluent CH$_2$Cl$_2$:MeOH=99:01. 5-(5-(Quinazolin-4-yloxy)pentyloxy)-2-((4-methylpiperazin-1-yl)methyl)-4H-pyran-4-one EHT 4063 was obtained (35 mg, 35%) as a white solid.

The structure of compound ex 29 is presented below:

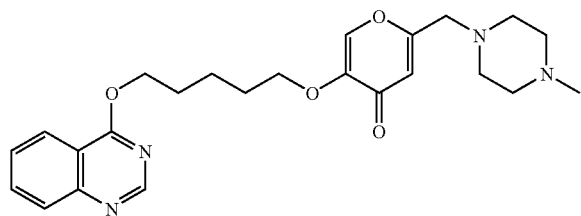

MW: 438.53; Yield: 35%; White solid; Mp: 78.2° C. Rf: 0.4 (CH$_2$Cl$_2$:MeOH=99:01). $^1$H-NMR (CDCl$_3$, d): 1.55-1.62 (m, 2H, CH$_2$), 1.82-1.91 (m, 4H, 2×CH$_2$), 2.32 (s, 3H, —CH$_3$), 2.30-2.80 (m, 8H, 4×CH$_2$N—), 3.38 (s, 2H, —NCH$_2$), 3.87 (t, 2H, J=6.3 Hz, —OCH$_2$), 4.03 (t, 2H, J=7.3 Hz, —CH$_2$O), 6.45 (s, 1H, —C=CH), 7.48-7.55 (m, 1H, ArH), 7.56 (s, 1H, —C=CH), 7.69-7.80 (m, 2H, ArH), 8.06 (s, 1H, —N=CH—N—), 8.31 (dd, 1H, J=7.8 Hz J=0.8 Hz, ArH). MS-ESI m/z (rel. Int.): 439 ([MH]$^+$, 100), 147 (45). HPLC: Method A, detection UV 254 nm, EHT 4063 RT=3.86 min, peak area 93.1%.

Preparation of EHT 8817

Example 30

5-(5-(7-(Trifluoromethyl)quinolin-4-ylthio)pentyloxy)-2-(fluoromethyl)-4H-pyran-4-one (EHT 8817)

2-Hydroxymethyl-5-[5-(7-trifluoromethyl-quinolin-4-yl-sulfanyl)-pentyloxy]-pyran-4-one EHT 5909 (100 mg, 0.23 mmol) was dissolved in dichloromethane (5 mL). The mixture was stirred at 0° C. for 15 min. Diethylaminosulfur trifluoride (DAST, 33 µL, 0.25 mmol) was added via syringe. The mixture was stirred at room temperature for 10 min. The solution was evaporated. The crude product was purified by flash chromatography on silica using as eluent CH$_2$Cl$_2$:MeOH=99:01. 5-(5-(7-(Trifluoromethyl)quinolin-4-ylthio)pentyloxy)-2-(fluoromethyl)-4H-pyran-4-one EHT 8817 was obtained (48 mg, 35% yield) as a white solid.

The structure of compound ex 30 is presented below:

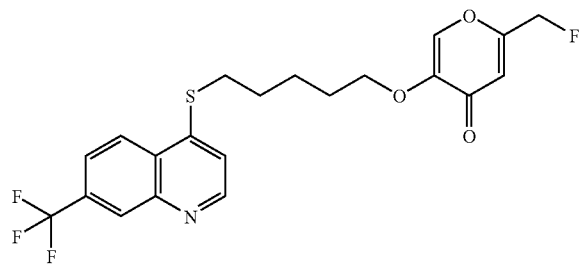

MW: 441.45; Yield: 35%; White solid; Mp: 107.0° C. R$_f$: 0.35 (CH$_2$Cl$_2$:MeOH=97:03). $^1$H-NMR (CDCl$_3$, d): 1.65-1.80 (m, 2H, CH$_2$), 1.70-1.95 (m, 4H, 2×CH$_2$), 3.16 (t, 2H, J=7.2 Hz, —SCH$_2$), 3.91 (t, 2H, J=6.2 Hz, —CH$_2$O), 5.12 (d, 2H, J=46.5 Hz, —CH$_2$F), 6.51 (s, 1H, —C=CH), 7.59 (s, 1H, —C=CH), 7.72 (dd, 1H, J=8.8 Hz J=1.7 Hz, ArH), 8.24 (d, 1H, J=8.8 Hz, ArH), 8.36 (s, 1H, ArH), 8.80 (d, 1H, J=4.8 Hz, ArH). MS-ESI m/z (rel. Int.): 442 ([MH]$^+$, 100). HPLC: Method A, detection UV 254 nm, EHT 8817 RT=5.08 min, peak area 99.9%.

Preparation of Intermediates 21-24

2-(Bromomethyl)-5-hydroxy-4H-pyran-4-one 21

In a 250 mL round-bottomed flask 5-hydroxy-2-(hydroxymethyl)-4H-pyran-4-one (10.0 g, 70.36 mmol) was added to concentrated H$_2$SO$_4$ (30 mL). The solution was cooled to 4° C. and bromohydric acid (40 mL) was added dropwise for 1.5 h. HBr vapors were trapped using a NaOH 0.5 N solution. The reaction was stirred at 70° C. for 18.5 h. After cooling ice (220 g) was added with continuous stirring for for 1.5 h to obtain a white precipitate. The solid was filtered off and dissolved in ethyl acetate and the solution was dried with MgSO$_4$, filtered and evaporated. 2-(Bromomethyl)-5-hydroxy-4H-pyran-4-one 21 was obtained as a pale yellow solid (9.1 g, 63% yield).

The structure of compound 21 is presented below:

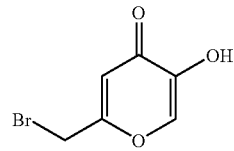

MW: 205.00; Yield: 63%; Pale yellow solid; Mp: 182.5° C. R$_f$: 0.70 (CH$_2$Cl$_2$:MeOH=9:1). $^1$H-NMR (CDCl$_3$, δ): 4.51 (s, 2H, S—CH$_2$), 4.-8 (s, 2H, Br—CH$_2$), 7.32-7.45 (m, 5H, Ar—H 7.72 (dd, 1H, J=8.8 Hz, J=1.7 Hz, ArH), 8.22 (d, J=8.8 Hz, 1H, ArH), 8.39 (s, 1H, ArH), 8.82 (d, J=4.8 Hz, 1H, ArH).

5-Hydroxy-2-(morpholinomethyl)-4H-pyran-4-one 22

2-(Bromomethyl)-5-hydroxy-4H-pyran-4-one 21 (5.0 g, 24.4 mmol), morpholine (4.3 mL, 48.8 mmol) and acetonitrile (120 mL) were charged in a 250 ml round-bottomed flask equipped with a magnetic stirrer. The reaction mixture was stirred for 3 h at 80° C. Acetonitrile was evaporated and the residu was extracted with EtOAc (400 mL). The organic layer was washed with water (20 mL), brine (2×20 mL), dried over MgSO$_4$, filtered and evaporated to dryness. Diethyl ether (25 mL) was added and the product was precipitated and filtered to give after drying 5-hydroxy-2-(morpholinomethyl)-4H-pyran-4-one 22 (4.8 g, 72% yield) as a white solid.

The structure of compound ex 22 is presented below:

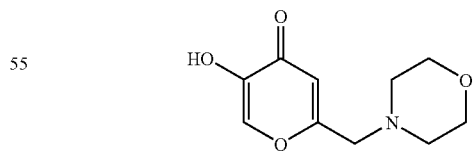

MW: 211.21; Yield: 72%; White solid; Mp: 144.2° C. R$_f$: 0.37 (CH$_2$Cl$_2$:MeOH=95:5). $^1$H-NMR (CDCl$_3$, δ): 2.53 (t, J=4.5 Hz, 4H, N—CH$_2$), 3.41 (s, 2H, N—CH$_2$), 3.74 (t, 4H, J=4.5 Hz, O—CH$_2$), 6.54 (s, 1H, —C=CH), 6.65 (s, 1H, OH), 7.86 (s, 1H, —C=CH). $^{13}$C-NMR (CDCl$_3$, δ): 53.4, 59.7, 66.6, 112.2, 138.6, 145.8, 165.2, 174.3. HPLC: Method A, detection UV 254 nm, 22 RT=1.0 min, peak area 99.5%.

5-Hydroxy-2-((4-methylpiperazin-1-yl)methyl)-4H-pyran-4-one hydrobromide 23

2-(Bromomethyl)-5-hydroxy-4H-pyran-4-one 21 (0.5 g, 2.4 mmol), 1-methylpiperazine (0.3 mL, 2.4 mmol) and tetrahydrofurane (12 mL) were charged in a 250 ml round-bottomed flask equipped with a magnetic stirrer. The reaction mixture was stirred for 2 h at 75° C. The reaction mixture was cooled and the precipitate was filtered to give after drying 5-hydroxy-2-((4-methylpiperazin-1-yl)methyl)-4H-pyran-4-one hydrobromide 23 (0.6 g, 83% yield) as a beige solid. A cesium salt was prepared by adding to $Cs_2CO_3$ (7.3 g, 22.4 mmol) in water (20 mL). The aqueous phase was washed with $CH_2Cl_2$ (200 mL), then water was evaporated at 40° C. and the cesium salt was drying under vacuum to give a white powder.

The structure of compound 23 is presented below:

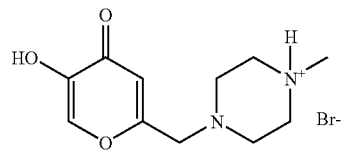

MW: 305.17; Yield: 83%; Beige solid; Mp: 208-210° C. $R_f$: 0.15 ($CH_2Cl_2$:MeOH 95:5). $^1$H-NMR of Cesium salt ($D_2O$, δ): 2.21 (s, 3H, N—$CH_3$), 2.50 (large signal, 8H, N—$CH_2$), 3.44 (s, 2H, N—$CH_2$), 6.39 (s, 1H, —C=CH), 7.72 (s, 1H, —C=CH). $^{13}$C-NMR of HCl salt ($D_2O$, δ): 42.7, 49.2, 53.0, 57.5, 114.2, 142.4, 144.9, 164.2, 176.4. MS-ESI m/z (rel. Int.): 225.0 ([MH]$^+$). HPLC: Method A, detection UV 254 nm, 23 RT 0.7 min, peak area 98%.

tert-Butyl 4-((5-hydroxy-4-oxo-4H-pyran-2-yl)methyl)piperazine-1-carboxylate 24

2-(Bromomethyl)-5-hydroxy-4H-pyran-4-one (8.9 g, 43.4 mmol), tert-butyloxycarbonylpiperazine (8.5 g, 45.6 mmol), triethylamine (7 mL, 49.9 mmol) and acetonitrile (200 mL) were charged in a 500 ml round-bottomed flask equipped with a magnetic stirrer. The reaction mixture was stirred for 2 h at 90° C. Acetonitrile was evaporated and EtOAc (50 mL) was added. The precipitate of $(C_2H_5)_3N$, HCl was filtered off and ethyl acetate was evaporated at 40° C. to dryness. The crude compound was purified by column chromatography (deactivated $SiO_2$:$CH_2Cl_2$:triethylamine 98:2 to $CH_2Cl_2$:MeOH 95:5, purification: $CH_2Cl_2$:MeOH 99.5:0:5 to 96:4) to give after evaporation tert-butyl 4-((5-hydroxy-4-oxo-4H-pyran-2-yl)methyl)piperazine-1-carboxylate 24 (10.5 g, 78% yield) as a white powder.

The structure of compound 24 is presented below:

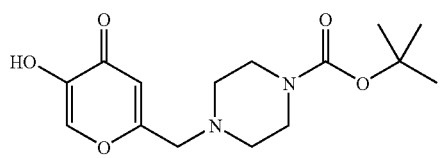

MW: 310.35; Yield: 78%; White solid; Mp: 146.7° C. $R_f$: 0.55 ($CH_2Cl_2$:MeOH=95:5). $^1$H-NMR (CDCl$_3$, δ): 1.46 (s, 9H, $CH_3$), 2.48 (t, J=4.9 Hz, 4H, N—$CH_2$), 3.43 (s, 2H, N—$CH_2$), 3.46 (t, 4H, J=5.1 Hz, N—$CH_2$), 6.53 (s, 1H, —C=CH), 7.85 (s, 1H, —C=CH). $^{13}$C-NMR (CDCl$_3$, δ): 28.4, 43.6, 52.9, 59.5, 79.9, 112.0, 138.2, 145.8, 154.6, 165.5, 174.2. HPLC: Method A, detection UV 254 nm, 24 RT=3.8 min, peak area 97.0%.

Preparation of Intermediates 25-33

4-(5-Bromopentylthio)-7-(trifluoromethyl)quinoline 25

7-Trifluoromethyl-4-quinoline-thiol (5 g, 21.8 mmol), 1,5-dibromopentane (23.7 g, 98.1 mmol) and CHCl$_3$ (60 mL) were charged in a 250 ml round-bottomed flask equipped with a magnetic stirrer. TBABr (0.7 g, 2.2 mmol) and water (40 mL) were added and the reaction mixture was stirred for 48 h at 20° C. The reaction mixture was poured in 100 mL of $H_2O$ with $K_2CO_3$ (3.0 g, 21.8 mmol) and extracted with $CH_2Cl_2$ (400 mL). The organic layer was washed with water (30 mL), brine (2×30 mL), dried over $MgSO_4$, filtered and evaporated at 30° C. to dryness. The crude compound was purified by column chromatography ($SiO_2$:$CH_2Cl_2$:MeOH=99.5:0.5 to 98:2) to give after evaporation 4-(5-bromopentylthio)-7-(trifluoromethyl)quinoline 25 (5.9 g, 72% yield) as a white solid.

The structure of compound 25 is presented below:

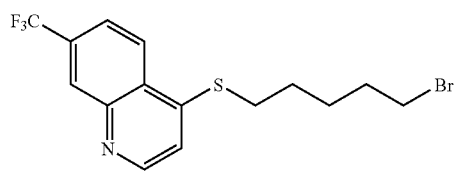

MW: 378.25; Yield: 72%; White solid; Mp: 60.3° C. $R_f$: 0.75 ($CH_2Cl_2$:EtOAc=9:1). $^1$H-NMR (CDCl$_3$, δ): 1.67-1.75 (m, 2H, $CH_2$), 1.81-1.99 (m, 4H, $CH_2$), 3.14 (t, J=7.2 Hz, 2H, S—$CH_2$), 3.44 (t, J=6.6 Hz, N—$CH_2$), 7.25 (d, J=4.8 Hz, 1H, Ar—H), 7.71 (dd, J=8.8 Hz, J=1.8 Hz, 1H, Ar—H), 8.23 (d, J=8.8 Hz, 1H, Ar—H), 8.36 (s, 1H, Ar—H), 8.79 (d, J=4.8 Hz, 1H, Ar—H). MS-ESI m/z (rel. Int.): 378.0/379.8 ([MH]$^+$). HPLC: Method A, detection UV 254 nm, 25, RT=6.0 min, peak area 99.5%.

4-[2-(2-Chloro-ethoxy)-ethylsulfanyl]-7-trifluoromethyl-quinoline 26

7-Trifluoromethyl-4-quinoline-thiol (2 g, 8.7 mmol) and 2-chloroethyl ether (6.2 g, 43.7 mmol) were charged in a 50 ml round-bottomed flask equipped with a magnetic stirrer. Then $Cs_2CO_3$ (2.8 g, 8.7 mmol), NaI (1.3 g, 8.7 mmol), TBABr (1.1 g, 3.5 mmol) and water (15 mL) were added and the reaction mixture was stirred for 1 h at 90° C. The reaction mixture was poured in 100 mL of $H_2O$, extracted with $CH_2Cl_2$ (2×100 mL). The organic layer was washed with brine (2×20 mL), dried over $MgSO_4$, filtered and evaporated to dryness. The crude compound was purified by column chromatography ($SiO_2$; $CH_2Cl_2$:MeOH=99:1 to 98:2) to give after evaporation 4-[2-(2chloro-ethoxy)-ethylsulfanyl]-7-trifluoromethyl-quinoline 26 (1.9 g, 65% yield) as a colourless oil.

The structure of compound 26 is presented below:

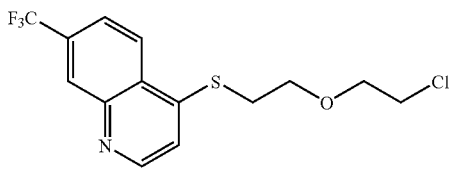

MW: 335.04; Yield: 65%; Colourless oil. $R_f$: 0.85 ($CH_2Cl_2$:MeOH=95:5). $^1$H-NMR ($CDCl_3$, δ): 3.37 (t, J=6.4 Hz, 2H, S—$CH_2$), 3.64 (t, J=5.7 Hz, 2H, Cl—$CH_2$), 3.79 (t, J=5.9 Hz, 2H, O—$CH_2$), 3.88 (t, J=6.4 Hz, 2H, O—$CH_2$), 7.36 (d, J=4.8 Hz, 1H, ArH), 7.72 (dd, J=8.8 Hz, J=1.6 Hz, 1H, ArH), 8.26 (d, J=8.8 Hz, 1H, ArH), 8.37 (s, 1H, ArH), 8.80 (d, J=4.8 Hz, 1H, ArH). MS-ESI m/z (rel. Int.): 335.9/338.0 ([MH]$^+$). HPLC: Method A, detection UV 254 nm, 26, RT=5.3 min, peak area 98.5%.

4-(2-(Bromomethyl)benzylthio)-7-(trifluoromethyl)quinoline 27

In a 25 mL round-bottomed flask 7-trifluoromethyl-quinoline-4-thiol (1.0 g, 4.37 mmol) was dissolved in 10 mL DMF anhydrous and NaH (60% dispersion in oil, 184 mg) was added slowly. The reaction was stirred at RT for 10 min. In a 50 mL round-bottomed flask 1,4-bis-bromomethyl-benzene (1.27 g, 4.80 mmol) was dissolved in DMF anhydrous (10 mL) and the solution was stirred at 0° C. for 10 min. The first solution was added via syringe to this solution and the reaction was stirred at 0° C. for 15 min. The solution orange became pale yellow and the mixture stirred 1.25 h at RT. Water (50 mL) was added and the product extracted with diethyl ether (5×100 mL). The organic layer was washed with water (3×50 mL), brine (3×50 mL), dried with $MgSO_4$, filtered and evaporated. The crude product was purified by column chromatography on silica using as eluent cyclohexane:diethyl ether=7:3. 4-(2-(Bromomethyl)benzylthio)-7-(trifluoromethyl)quinoline 27 was obtained (205 mg, 12% yield) as white solid.

The structure of compound 27 is presented below:

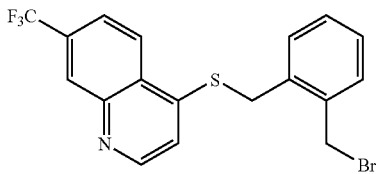

MW: 412.26; Yield: 12%; White solid; Mp: 177.4° C. $R_f$: 0.40 (cyclohexane:diethyl ether=70:30). $^1$H-NMR ($CDCl_3$, δ): 4.51 (s, 2H, S—$CH_2$), 4.68 (s, 2H, Br—$CH_2$), 7.32-7.45 (m, 5H, ArH), 7.72 (dd, 1H, J=8.8 Hz, J=1.7 Hz, ArH), 8.22 (d, J=8.8 Hz, 1H, ArH), 8.39 (s, 1H, ArH), 8.82 (d, J=4.8 Hz, 1H, ArH). MS-ESI m/z (rel. Int.): 411.8/413.8 ([MH]$^+$). HPLC: Method A, detection UV 254 nm, 27, RT=6.32 min, peak area 96.8%.

4-(3-(Bromomethyl)benzylthio)-7-(trifluoromethyl)quinoline 28

7-Trifluoromethyl-4-quinoline-thiol (3.0 g, 13.1 mmol), 1,3-bis-bromomethyl-benzene (10.4 g, 39.3 mmol) and $CHCl_3$ (150 mL) were charged in a 250 ml round-bottomed flask equipped with a magnetic stirrer. TBABr (0.5 g, 1.5 mmol) and water (12 mL) were added and the reaction mixture was stirred for 15 h at 20° C. The reaction mixture was poured in 10 mL of $H_2O$ with $K_2CO_3$ (1.8 g, 13.1 mmol), extracted with $CH_2Cl_2$ (400 mL). The organic layer was washed with water (30 mL), brine (2×30 mL), dried over $MgSO_4$, filtered and evaporated at 30° C. to dryness. Diethyl ether (150 mL) was added and the bis-alkylated product was precipitated and filtered off. The filtrate was evaporated and the crude compound was purified by column chromatography ($SiO_2$; $CH_2Cl_2$:MeOH=99.5:0.5 to 96:4) to give after evaporation 4-(3-(bromomethyl)benzylthio)-7-(trifluoromethyl)quinoline 28 (3.3 g, 61% yield) as a white solid.

The structure of compound 28 is presented below:

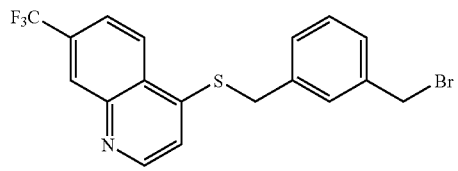

MW: 412.27; Yield: 61%; White solid; Mp: 211.1° C. $R_f$: 0.45 ($CH_2Cl_2$:MeOH=99.5:0.5). $^1$H-NMR ($CDCl_3$, δ): 4.32 (s, 2H, S—$CH_2$), 4.47 (s, 2H, Br—$CH_2$), 7.27 (d, J=4.8 Hz, 1H, Ar—H), 7.32-7.39 (m, 1H, Ar—H), 7.47 (s, 1H, Ar—H), 7.70 (dd, J=8.8 Hz, J=1.7 Hz, 1H, Ar—H), 8.22 (d, J=8.8 Hz, 1H, Ar—H), 8.36 (s, 1H, Ar—H), 8.75 (d, J=4.8 Hz, 1H, Ar—H). MS-ESI m/z (rel. Int.): 411.8/412.9 ([MH]$^+$). HPLC: Method A, detection UV 254 nm, 28, RT=6.2 min, peak area 99.7%.

4-(4-(Bromomethyl)benzylthio)-7-(trifluoromethyl)quinoline 29

In 25 mL round-bottomed flask 25 mL 7-trifluoromethyl-quinoline-4-thiol (1.0 g, 4.37 mmol) was dissolved in 8 mL DMF anhydrous and NaH (60% dispersion in oil, 184 mg) was added slowly. The reaction was stirred at RT for 10 min. In a 50 mL round-bottomed flask 1,4-bis-bromomethyl-benzene (1.27 g, 4.80 mmol) was dissolved in DMF anhydrous (10 mL) and the solution was stirred at 0° C. for 10 min. The first solution was added via syringe to this solution and the reaction was stirred at 0° C. for 15 min. The solution orange became pale yellow and the mixture stirred 2 h at RT. Water (50 mL) was added and the product extracted with diethyl ether (5×100 mL). The organic layer was washed with water (3×50 mL), brine (3×50 mL), dried with $MgSO_4$, filtered and evaporated. The crude product was purified by column chromatography on silica using as eluent cyclohexane:diethyl ether=7:3. 4-(4-(Bromomethyl)benzylthio)-7-(trifluoromethyl)quinoline 29 was obtained (265 mg, 15% yield) as white solid.

The structure of compound 29 is presented below:

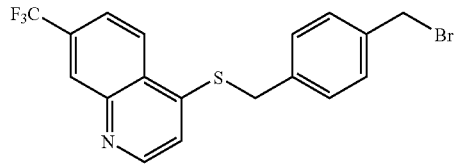

MW: 412.26; Yield: 15%; White solid; Mp: 196.7° C. $R_f$: 0.40 (cyclohexane:diethyl ether=70:30). $^1$H-NMR (CDCl$_3$, δ): 4.34 (s, 2H, S—CH$_2$), 4.48 (s, 2H, Br—CH$_2$), 7.28 (d, J=4.8 Hz, 1H, ArH), 7.32-7.45 (m, 4H, ArH), 7.71 (dd, 1H, J=8.8 Hz, J=1.7 Hz, ArH), 8.23 (d, J=8.8 Hz, 1H, ArH), 8.37 (s, 1H, ArH), 8.76 (d, J=4.8 Hz, 1H, ArH). MS-ESI m/z (rel. Int.): 411.8/413.8 ([MH]$^+$). HPLC: Method A, detection UV 254 nm, 29, RT=6.22 min, peak area 95.0%.

4-(2-Chloroethylthio)-7-(trifluoromethyl) quinoline 30

7-Trifluoromethyl-4-quinoline-thiol (800 mg, 3.5 mmol) and 1,2-dichloroethane (10.4 g, 10.5 mmol) were charged in a 50 ml round-bottomed flask equipped with a magnetic stirrer. Then TBABr (600 mg, 1.7 mmol), K$_2$CO$_3$ (500 mg, 3.5 mmol), KOH (500 mg, 0.7 mmol) and water (2 mL) were added and the reaction mixture was stirred for 5 h at 20° C. The reaction mixture was poured in 100 mL of H$_2$O and extracted with CH$_2$Cl$_2$ (150 mL). The organic layer was washed with water (30 mL), brine (2×10 mL), dried over MgSO$_4$, filtered and evaporated at 30° C. to dryness. The crude compound was purified by column chromatography (SiO$_2$; CH$_2$Cl$_2$:EtOAc=8:2 to 5:5) to give after evaporation 4-(2-chloroethylthio)-7-(trifluoromethyl)quinoline 30 (680 mg, 67% yield) as a beige solid.

The structure of compound 30 is presented below:

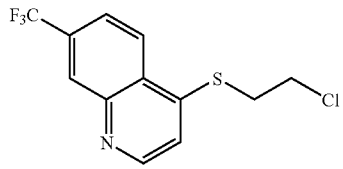

MW: 291.72; Yield: 67%; Beige solid; Mp: 96.2° C. $R_f$: 0.60 (CH$_2$Cl$_2$:EtOAc=8:2). $^1$H-NMR (CDCl$_3$, δ): 3.49-3.54 (m, 2H, S—CH$_2$), 3.76-3.91 (m, 2H, Cl—CH$_2$), 7.33 (d, J=4.8 Hz, 1H, Ar—H), 7.75 (dd, J=8.8 Hz, J=1.8 Hz, 1H, Ar—H), 8.25 (d, J=8.8 Hz, 1H, Ar—H), 8.39 (s, 1H, Ar—H), 8.85 (d, J=4.8 Hz, 1H, Ar—H). MS-ESI m/z (rel. Int.): 291.9/293.9 ([MH]$^+$). HPLC: Method A, detection UV 254 nm, 30, RT=5.6 min, peak area 99.5%.

4-(2-Chloroethoxy)-7-(trifluoromethyl)quinoline 31

7-Trifluoromethyl-4-quinolinol (500 mg, 2.3 mmol) and 1,2-dichloroethane (11.6 g, 11.7 mmol) were charged in a 50 ml round-bottomed flask equipped with a magnetic stirrer. TBABr (370 mg, 1.2 mmol), K$_2$CO$_3$ (950 mg, 6.9 mmol), KOH (760 mg, 11.5 mmol) and water (6 mL) were added and the reaction mixture was stirred for 5 h at 70-80° C. The reaction mixture was poured in 50 mL of H$_2$O and extracted with CH$_2$Cl$_2$ (150 mL). The organic layer was washed with water (30 mL), brine (2×10 mL), dried over MgSO$_4$, filtered and evaporated at 30° C. to dryness. The crude compound was purified by column chromatography (SiO$_2$; CH$_2$Cl$_2$:EtOAc=5:5) to give after evaporation 4-(2-chloroethoxy)-7-(trifluoromethyl)quinoline 31 (150 mg, 25% yield) as a beige solid.

The structure of compound 31 is presented below:

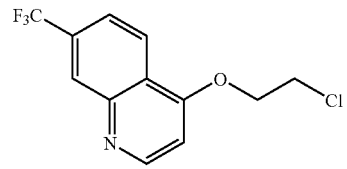

MW: 275.65; Yield: 25%; Beige solid; Mp: 56.2° C. $R_f$: 0.25 (CH$_2$Cl$_2$:EtOAc=5:5). $^1$H-NMR (CDCl$_3$, δ): 4.00 (t, J=5.6 Hz, 2H, Cl—CH$_2$), 4.49 (t, J=5.6 Hz, 2H, O—CH$_2$), 6.82 (d, J=5.2 Hz, 1H, Ar—H), 7.71 (d, J=8.7 Hz, 1H, Ar—H), 8.35-8.39 (m, 2H, Ar—H), 8.85 (d, J=5.2 Hz, 1H, Ar—H). MS-ESI m/z (rel. Int.): 275.9/277.8 ([MH]$^+$). HPLC: Method A, detection UV 254 nm, 31, RT=4.5 min, peak area 99.0%.

5-Bromo-N-(7-(trifluoromethyl)quinolin-4-yl)pentanamide 32

4-Amino-7-trifluoromethylquinoline (120 mg, 0.56 mmol), triethylamine (170 mg, 1.7 mmol) and CHCl$_3$ (4 mL) were charged in a 10 ml round-bottomed flask equipped with a magnetic stirrer. 5-Bromovaleryl chloride (140 mg, 0.7 mmol in CHCl$_3$ (2 mL) were added and the reaction mixture was stirred for 15 h at 20° C. The reaction mixture was poured in 10 mL of H$_2$O and extracted with CH$_2$Cl$_2$ (100 mL). The organic layer was washed with brine (2×10 mL), dried over MgSO$_4$, filtered and evaporated at 30° C. to dryness. The crude compound was purified by column chromatography (SiO$_2$; CH$_2$Cl$_2$:MeOH=99.5:0.5 to 98:2) to give after evaporation 5-bromo-N-(7-(trifluoromethyl)quinolin-4-yl)pentanamide 32 (190 mg, 90% yield) as a beige solid.

The structure of compound 32 is presented below:

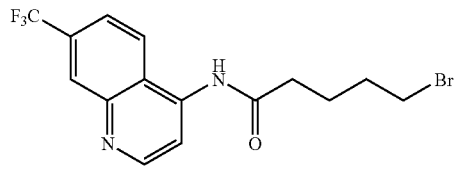

MW: 375.18; Yield: 90%; Beige solid; Mp: 135.3° C. $R_f$: 0.65 (CH$_2$Cl$_2$:MeOH=95:5). $^1$H-NMR (CDCl$_3$, δ): 1.83-1.99 (m, 4H, CH$_2$), 2.48-2.64 (m, 2H, COCH$_2$), 3.40-3.58 (m, 2H, Br—CH$_2$), 7.53 (dd, J=8.8 Hz, J=1.6 Hz, 1H, Ar—H), 7.98 (d, J=8.8 Hz, 1H, Ar—H), 8.13 (d, J=5.1 Hz, 1H, Ar—H), 8.22 (s, 1H, Ar—H), 8.76 (d, J=5.0 Hz, 1H, Ar—H), 8.93 (d, J=4.8 Hz, 1H, Ar—H). $^{13}$C-NMR (CDCl$_3$, δ): 23.8, 31.8, 33.0, 36.4, 113.7, 121.7, 121.8, 122.2, 125.3, 127.4, 131.2, 140.9, 147.5, 152.0, 172.1. HPLC: Method A, detection UV 254 nm, 32, RT=5.1 min, peak area 95%.

4-(5-Bromopentyloxy)-7-chloroquinoline 33

7-Chloro4-quinolinol (2 g, 11.1 mmol), Li$_2$CO$_3$ (1.7 g, 22.3 mmol) and NMP (16 mL) were charged in a 100 ml round-bottomed flask equipped with a magnetic stirrer. 1,5-Dibromopentane (13.5 g, 55.7 mmol) was added and the reaction mixture was stirred for 1 h at 90° C. The reaction mixture was poured in 100 mL of H$_2$O, extracted with EtOAc (300 mL). The organic layer was washed with water (30 mL), brine (2×30 mL), dried over MgSO$_4$, filtered and evaporated at 30° C. to dryness. HCl 1M in diethyl ether (15 mL, 15 mmol) was added and the bis-alkylated product was precipitated and filtered. The precipitate was dissolved in water with K₂CO₃ (1.5 g, 11.1 mmol), extracted with EtOAc (300 mL). The organic layer was washed with brine (2×20 mL), dried over MgSO₄, filtered and evaporated at 30° C. to dryness. The crude compound was purified by column chromatography (SiO₂; CH₂Cl₂:MeOH=99.5:0.5 to 95:5) to give after evaporation 4-(5-bromopentyloxy)-7-chloroquinoline 33 (0.45 g, 12% yield) as a white solid.

The structure of compound 33 is presented below:

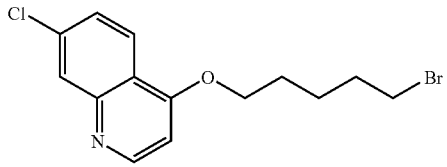

MW: 328.63; Yield: 12%; White solid; Mp: 63.3° C. R_f: 0.80 (CH₂Cl₂:MeOH=95:5). ¹H-NMR (CDCl₃, δ): 1.63-1.71 (m, 2H, CH₂), 1.85-1.99 (m, 4H, CH₂), 3.44 (t, J=6.7 Hz, 2H, Br—CH₂), 4.08 (t, J=6.3 Hz, 2H, O—CH₂), 6.59 (d, J=5.3 Hz, 1H, Ar—H), 7.37 (dd, J=8.9 Hz, J=2.0 Hz, 1H, Ar—H), 7.97 (d, J=2.0 Hz, 1H, Ar—H), 8.04 (d, J=8.9 Hz, 1H, Ar—H), 8.65 (d, J=5.2 Hz, 1H, Ar—H). ¹³C-NMR (CDCl₃, δ): 24.7, 27.9, 32.3, 33.5, 68.2, 100.8, 119.7, 123.4, 126.2, 127.7, 135.4, 149.5, 152.4, 161.3. MS-ESI m/z (rel. Int.): 328.0/329.9 ([MH]⁺). HPLC: Method A, detection UV 254 nm, 33, RT=5.0 min, peak area 99.5%.

Preparation of EHT 5575, EHT 6892, EHT 1864, EHT 0371, EHT 6037, EHT 9069, EHT 2725, EHT 0434, EHT 2218, EHT 9358, EHT 2580 and EHT 9241

Example 31

5-(2-(7-(Trifluoromethyl)quinolin-4-ylthio)ethoxy)-2-((tetrahydro-2H-pyran-2-yloxy)methyl)-4H-pyran-4-one (EHT 5575)

5-Hydroxy-2-(tetrahydro-pyran-2-yloxymethyl)-pyran-4-one (360 mg, 1.6 mmol), Cs₂CO₃ (520 mg, 1.6 mmol), TBABr (90 mg, 0.3 mmol), water (2 mL) and CHCl₃ (5 mL) were charged in a 50 ml round-bottomed flask equipped with a magnetic stirrer. 4-(2-Chloroethylthio)-7-(trifluoromethyl)quinoline 30 (230 mg, 0.8 mmol) was added and the reaction mixture was stirred for 15 h at 20° C. The reaction mixture was poured in 20 mL of H₂O and extracted with CH₂Cl₂ (2×25 mL). The organic layer was washed with brine (10 mL), dried over MgSO₄, filtered and evaporated to dryness. The crude compound was purified by column chromatography (SiO₂; EtOAc) to give after evaporation EHT 5575 (20 mg, 5% yield) as a pasty product.

The structure of ex 31 is presented below:

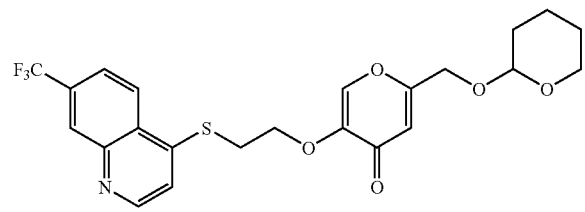

MW: 481.48; Yield: 5%; Pasty product. R_f: 0.25 (EtOAc). ¹H-NMR (CDCl₃, δ): 1.74-1-83 (m, 6H, CH₂), 3.52-3.60 (m, 2H, S—CH₂ and 1H, O—CH₂) 3.78-3.86 (m, 1H, O—CH₂), 4.28-4.35 (m, 2H, O—CH₂ and 1H, O—CH₂), 4.52 (d, J_AB=14.5 Hz, 1H, O—CH₂), 4.72 (t, J=3.0 Hz, 1H, CH), 6.54 (s, 1H, C=CH), 7.44 (d, J=4.8 Hz, ArH), 7.68 (s, 1H, C=CH), 7.73 (dd, 1H J=8.8 Hz, J=1.8 Hz, ArH), 7.25 (d, 1H, J=8.8 Hz, ArH), 8.38 (d, 1H, ArH), 8.83 (d, 1H, J=4.8 Hz, ArH). MS-ESI m/z (rel. Int.): 481.9 ([MH]⁺). HPLC: Method A, detection UV 254 nm, EHT 5575 RT=5.20 min, peak area 98.5%.

Example 32

5-(2-(7-(trifluoromethyl)quinolin-4-yloxy)ethoxy)-2-(morpholinomethyl)-4H-pyran-4-one (EHT 6892)

5-Hydroxy-2-(morpholinomethyl)-4H-pyran-4-one 22 (130 mg, 0.6 mmol), Cs₂CO₃ (200 mg, 0.6 mmol) and anhydrous DMF (5 mL) were stirred at 40° C. in a 50 ml round-bottomed flask equipped with a magnetic stirrer. After 30 min, 4-(2-chloroethoxy)-7-(trifluoromethyl)quinoline 31 (140 mg, 0.5 mmol) and NaI (80 mg, 0.5 mmol) were added and the reaction mixture was stirred for 3 h at 90° C. DMF was evaporated and the reaction mixture was poured in 20 mL of H₂O, extracted with EtOAc (3×40 mL). The organic layer was washed with brine (10 mL), dried over MgSO₄, filtered and evaporated to dryness. The crude compound was purified by column chromatography (SiO₂; CH₂Cl₂:MeOH=99:1 to 95:5) to give after evaporation EHT 6892 (100 mg, 35% yield) as a white solid.

The structure of compound ex 32 is presented below:

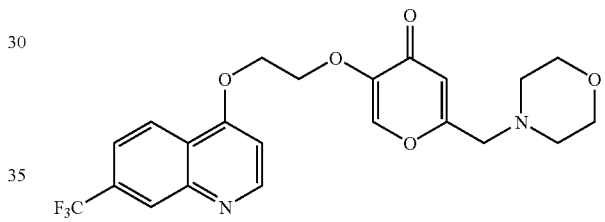

MW: 450.41; Yield: 35%; White solid; Mp: 125.6° C. R_f: 0.27 (CH₂Cl₂:MeOH=95:5). ¹H-NMR (CDCl₃, δ): 2.52 (t, J=4.6 Hz, 2H, N—CH₂), 3.38 (s, 2H, N—CH₂), 3.73 (t, J=4.5 Hz, 2H, O—CH₂), 4.53-4.58 (m, 4H, S—CH₂, O—CH₂), 6.51 (s, 1H, C=CH), 6.87 (d, J=5.2 Hz, ArH), 7.65 (dd, J=8.8 Hz, J=1.5 Hz, ArH), 7.79 (s, 1H, C=CH), 8.29-8.32 (m, 2H, ArH), 8.83 (d, 1H, J=5.2 Hz, ArH). MS-ESI m/z (rel. Int.): 451.0 ([MH]⁺) HPLC: Method A, detection UV 254 nm, EHT 6892 RT=3.70 min, peak area 98.5%.

Example 33

5-(5-(7-(Trifluoromethyl)quinolin-4-ylthio)pentyloxy)-2-(morpholinomethyl)-4H-pyran-4-one dihydrochloride (EHT 1864)

5-Hydroxy-2-(morpholinomethyl)-4H-pyran-one 22 (2.5 g, 12.0 mmol), Cs₂CO₃ (3.9 g, 12.0 mmol) and anhydrous DMF (40 mL) were charged in a 250 ml round-bottomed flask equipped with a magnetic stirrer under inert atmosphere. 4-(5-Bromopentylthio)-7-(trifluoromethyl)quinoline 25 (3.8 g, 10.0 mmol) and NaI (0.2 g, 1.3 mmol) were added and the reaction mixture was stirred for 2 h at 90° C. After evaporation of DMF, the reaction mixture was poured in 50 mL of H₂O, extracted with CH₂CO₂ (2×200 mL). The organic layer was washed with brine (2×20 mL), dried over MgSO₄, filtered and evaporated to dryness. The crude compound was purified by column chromatography (SiO₂; CH₂Cl₂: MeOH=99:1 to 94:6) to give after evaporation a pure solid (4.4 g, 88% yield). The compound was dissolved in EtOH (150 mL), then HCl 1M in EtOH (22 mL, 21.6 mmol) was added and the reaction mixture was stirred for 2 h at 20° C. After evaporation of EtOH, the hydrochloride compound was dried under vacuum and crystallized in ethanol (50 mL) to yield to EHT 1864 (3.35 g, 58% yield) as a white powder.

The structure of compound ex 33 is presented below:

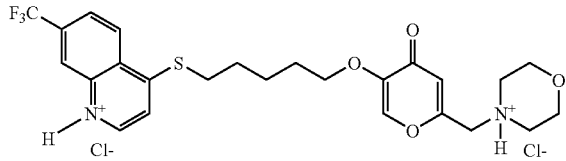

MW: 581.47; Yield: 58%; White powder, Mp: 217.7° C. $R_f$: 0.40 (CH$_2$Cl$_2$:MeOH=95:5). $^1$H-NMR (CDCl$_3$, δ): 1.62-1.64 (m, 2H, CH$_2$), 1.76-1.87 (m, 4H, CH$_2$), 3.10-3.38 (m, 4H, N—CH$_2$), 3.42 (t, J=6.6 Hz, 2H, S—CH$_2$), 3.85-3.91 (m, 6H, O—CH$_2$), 4.34 (s, 2H, N—CH$_2$), 6.77 (s, 1H, C=CH), 7.88 (d, J=5.0 Hz, 1H, Ar—H), 8.08 (d, J=8.9 Hz, 1H, Ar—H), 8.21 (s, 1H, C=CH), 8.45 (d, J=8.8 Hz, 1H, Ar—H), 8.67 (s, 1H, Ar—H), 9.06 (d, J=5.5 Hz, 1H, Ar—H), 11.15 (s, 1H, NH$^+$), 12.25 (s, 1H, NH$^+$). MS-ESI m/z (rel. Int.): 509.0 ([MH]$^+$, 100). HPLC: Method A, Detection UV 254 nm, EHT 1864 RT=4.40 min, peak area 99.9%. Anal. (C$_{25}$H$_{27}$F$_3$N$_2$O$_4$S.2HCl); C, H, N, S: calcd, 51.64; 5.03, 4.82, 5.51, found, 51.18, 5.06, 4.83, 5.31.

Example 34

5-(2-(2-(7-(Trifluoromethyl)quinolin-4-ylthio) ethoxy)ethoxy)-2-(morpholinomethyl)-4H-pyran-4one (EHT 0371)

5-Hydroxy-2-(morpholinomethyl)-4H-pyran-4one 22 (350 mg, 1.7 mmol), Cs$_2$CO$_3$ (550 mg, 1.7 mmol) and anhydrous DMF (5 mL) were charged in a 30 ml sealed tube equipped with a magnetic stirrer and under inert atmosphere. 4-[2-(2-Chloro-ethoxy)-ethylsulfanyl]-7-trifluoromethyl-quinoline 26 (480 mg, 1.4 mmol) and NaI (210 mg, 1.4 mmol) were added and the reaction mixture was stirred for 2 h at 90° C. After evaporation of DMF, the reaction mixture was poured in 50 mL of H$_2$O and extracted with CH$_2$Cl$_2$ (3×50 mL). The organic layer was washed with brine (2×10 mL), dried over MgSO$_4$, filtered and evaporated to dryness. The crude compound was purified by column chromatography (SiO$_2$; CH$_2$Cl$_2$:MeOH=99.4:0.6 to 97:3) to give after evaporation EHT 0371 (400 mg, 56% yield) as a pale yellow oil.

The structure of compound ex 34 is presented below:

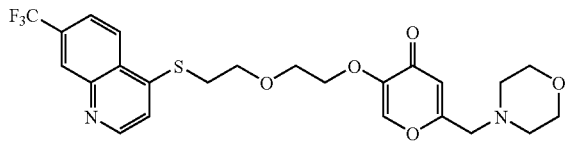

MW: 510.53; Yield: 60%; Pale Yellow Oil. $R_f$: 0.4 (CH$_2$Cl$_2$:MeOH: 95:5). $^1$H-NMR (DMSO d$_6$, δ): 2.51 (t, J=4.6 Hz, 2H, N—CH$_2$), 3.33 (s, 2H, N—CH$_2$), 3.38 (t, J=6.3 Hz, 2H, S—CH$_2$), 3.72 (t, J=4.6 Hz, 2H, O—CH$_2$), 3.86-3.94 (m, 4H, O—CH$_2$), 4.11 (m, 2H, O—CH$_2$), 6.46 (s, 1H, C=CH), 7;37 (d, J=4.8 Hz, 1H, ArH), 7.69 (s, 1H, C=CH), 7.71 (dd, J=8.8 Hz, J=1.7 Hz, 1H, ArH), 8.25 (d, J=8.8 Hz, 1H, ArH), 8.36 (s, 1H, ArH), 8.79 (d, J=4.8 Hz, 1H, ArH). $^{13}$CNMR (DMSO d$_6$, δ): 31.1, 53.5, 59.6, 66.7, 69.0, 69.6, 69.7, 114.9, 117.7, 121.9, 125.0, 125.6, 127.7, 128.1, 131.6, 141.3, 146.6, 147.6, 147.7, 150.6, 164.2, 174.4.MS-ESI m/z (rel. Int.): 511 ([MH]$^+$, 100). HPLC: Method A, detection UV 254 nm, EHT 0371 RT=5.0 min, peak area 100.0%.

Example 35

5-(6-(Morpholinomethyl)-4-oxo-4H-pyran-3-yloxy)-N-(7-(trifluoromethyl)quinolin-4-yl)pentanamide (EHT 6037)

5-Hydroxy-2-(morpholinomethyl)-4H-pyran-4-one 22 (85 mg, 0.4 mmol), Cs$_2$CO$_3$ (130 mg, 0.4 mmol) and anhydrous DMF (5 mL) were charged in a 30 ml sealed tube equipped with a magnetic stirrer and under inert atmosphere. Then 5-Bromo-N-(7-(trifluoromethyl)quinolnyl)pentanamide 32 (100 mg, 0.3 mmol) was added and the reaction mixture was stirred for 3 h at 90° C. After evaporation of DMF, the reaction mixture was poured in 50 mL of H$_2$O, extracted with EtOAc (3×30 mL). The organic layer was washed with brine (2×10 mL), dried over MgSO$_4$, filtered and evaporated to dryness. The crude compound was purified by column chromatography (SiO$_2$; CH$_2$Cl$_2$:MeOH=99.9:0.1 to 95:5) to give after evaporation EHT 6037 (45 mg, 55% yield) as a white powder.

The structure of compound ex 35 is presented below:

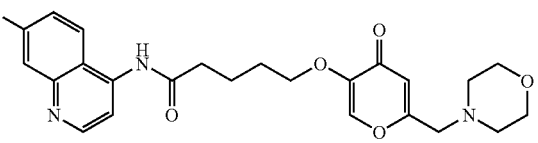

MW: 505.49; Yield: 55%; White solid, Mp: 126.8° C. $R_f$: 0.45 (CH$_2$Cl$_2$:MeOH=95:5). $^1$H-NMR (CDCl$_3$, δ): 1.90-1.96 (m, 2H, CH$_2$), 2.03-2.11 (m, 2H, CH$_2$), 2.54 (t, J=4.6 Hz, 4H, N—CH$_2$), 2.83 (t, J=6.4 Hz, 2H, CO—CH$_2$), 3.41 (s, 2H, N—CH$_2$), 3.74 (t, J=4.6 Hz, 4H, O—CH$_2$), 4.02 (t, J=5.0 Hz, 2H, O—CH$_2$), 6.51 (s, 1H, C=CH), 7.62 (dd, J=8.9 Hz, J=1.8 Hz, 1H, Ar—H), 7.66 (s, 1H, C=CH), 8.27 (d, J=5.1 Hz, 1H, Ar—H), 8.36 (s, 1H, Ar—H), 8.41 (d, J=8.8 Hz, 1H, Ar—H), 8.92 (d, J=5.0 Hz, 1H, Ar—H), 10.19 (s, 1H, Ar—H). MS-ESI m/z (rel. Int.): 506.1 ([MH]$^+$, 100). HPLC: Method A, Detecton UV 254 nm, EHT 6037 RT=3.80 min, peak area 95.8%.

Example 36

5-((2-((7-(Trifluoromethyl)quinolin-4-ylthio)methyl) phenyl)methoxy)-2-(morpholinomethyl)-4H-pyran-4-one (EHT 9069)

In a 50 mL round-bottomed flask 5-hydroxy-2-(morpholinomethyl)-4H-pyran-4-one 22 (95 mg, 0.45 mmol) was dissolved in DMF anhydrous (5 mL) and Cs$_2$CO$_3$ (161 mg, 0.50 mmol) was added at RT. The pale yellow reaction mixture was stirred for 10 min and cooled to 0° C. for. 15 min. In a 25 mL round-bottomed flask 4-(2-bromomethyl-benzylsulfanyl)-7-trifluoromethyl-quinoline 27 (185 mg, 0.45 mmol) was dissolved in DMF anhydrous (10 mL) and the solution cooled to 0° C. for 10 min. This solution was added via syringe to the first reaction mixture at 0° C. for 15 min. The reaction mixture was stirred 1.75 h at room temperature (orange). Water (100 mL) was added and the solution was extracted with EtOAc (3×100 mL). The organic layer was washed with water (5×75 mL), brine (3×100 mL), dried over MgSO$_4$, filtered and evaporated to dryness. The crude product was purified by column chromatography on silica using as eluent CH$_2$Cl$_2$: MeOH=98:2. 5-((2-((7-Trifluoromethyl)quinolin-4-ylthio) methyl)phenyl)methoxy)-2-morpholinomethyl)-4H-pyran-4-one EHT 9069 was obtained (155 mg, 64% yield) as a white solid.

The structure of compound ex 36 is presented below:

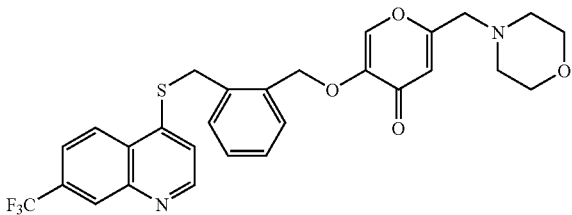

MW: 542.58; Yield: 64%; White solid; Mp: 71.6° C. ¹H-NMR (CDCl₃, δ): 2.50(t, J=4.6 Hz, 4H, 2×CH₂—N), 3.31 (s, 2H, CH₂—N), 3.71 (t, J=4.6 Hz, 4H, 2×CH₂—O), 4.59 (s, 2H, —SCH₂), 5.21 (s, 2H, O—CH₂), 6.45 (s, 1H, —C═CH), 7.30-7.50 (m, 4H, ArH), 7.67 (s, 1H, —C═CH), 7.70 (dd, J=8.8 Hz J=1.7 Hz, 2H, ArH), 8.20 (d, J=8.8 Hz, 1H, ArH), 8.37 (s, 1H, ArH), 8.80 (d, J=4.8 Hz, 1H, ArH). MS-ESI m/z(rel. Int.): 543.0 (100%, [MH]⁺), 314.1 (80), 230 (40). HPLC: Method A, detection UV 254 nm, EHT 9069 RT=4.65 min, peak area 98.6%.

Example 37

5-((3-((7-(Trifluoromethyl)quinolin-4-ylthio)methyl) phenyl)methoxy)-2-(morpholinomethyl)-4H-pyran-4-one dihydrochloride (EHT 0434) and its free base (EHT 2725)

5-Hydroxy-2-(morpholinomethyl)-4H-pyran-4-one 22 (3.1 g, 14.7 mmol), Cs₂CO₃ (4.8 g, 14.7 mmol) and anhydrous DMF (40 mL) were charged in a 250 ml round-bottomed flask equipped with a magnetic stirrer under inert atmosphere. 4-(3-(Bromomethyl)benzylthio)-7-trifluoromethyl)quinoline 28 (5.8 g, 14.1 mmol) in DMF (60 mL) was added at 4° C. and the reaction mixture was stirred for 4 h at 20° C. The reaction mixture was poured in 300 mL of ice-water, extracted with EtOAc (2×500 mL). The organic layer was washed with brine (2×50 mL), dried over MgSO₄ (50 g) with charcoal (2 g) and poured on covered SiO₂ (300 mL) of celite 545 (200 mL) and was evaporated to dryness. The crude compound was purified by column chromatography (SiO₂; CH₂Cl₂:MeOH=99.8:0.2 to 96:4) to give after evaporation the free base EHT 2725 (5.8 g, 76% yield). EHT 2725 was dissolved in EtOH (150 mL), HCl 1M in EtOH (26 mL, 26.3 mmol) was added and the reaction mixture was stirred for 0.5 h at 20° C. After evaporation of EtOH, the dihydrochloride salt was dried under vacuum and crystallized in isopropanol (500 mL) to yield to EHT 0434 (4.4 g, 48% yield) as a beige powder.

The structure of compound ex 37 is presented below:

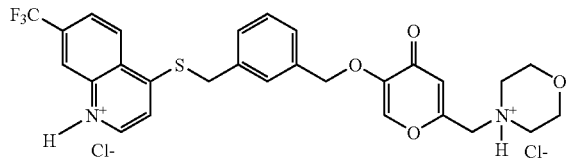

MW: 615,49; Yield: 48%; beige powder, Mp: 120.3° C. R_f: 0.40 (CH₂Cl₂:MeOH=95:5). ¹H-NMR (DMSO d₆, δ): 3.28 (m, 4H, N—CH₂), 3.91 (m, 4H, O—CH₂), 4.36 (s, 2H, N—CH₂), 4.74 (s, 2H, S—CH₂), 4.95 (s, 2H, O—CH₂), 7.40-7.62 (m, 4H, Ar—H), 7.93 (d, J=5.6 Hz, 1H, Ar—H), 8.03 (d, J=8.8 Hz, 1H, Ar—H), 8.30 (s, 1H, C═CH), 8.43 (d, J=8.8 Hz, 1H, Ar—H), 8.55 (s, 1H, Ar—H), 9.04 (d, J=5.5 Hz, 1H, Ar—H), 10.00 (s, 1H, NH+), 12.20 (s, 1H, NH+). MS-ESI m/z (rel. int.): 543.0 ([MH]+, 100). HPLC: Method A, Detection UV 254 nm, EHT 0434 RT=4.60 min, peak area 99.4%.

Example 38

5-((4-((7-(Trifluoromethyl)quinolin-4-ylthio)methyl) phenyl)methoxy)-2-(morpholinomethyl)-4H-pyran-4-one (EHT 2218)

In a 50 mL round-bottomed flask 5-hydroxy-2-(morpholinomethyl)-4H-pyran-4-one 22 (128 mg, 0.61 mmol) was dissolved in DMF anhydrous (10 mL) and Cs₂CO₃ (217 mg, 0.67 mmol) was added at RT. The reaction mixture was stirred for 10 min and cooled to 0° C. for 15 min. In a 25 mL round-bottomed flask, 4-(4-bromomethyl-benzylsulfanyl)-7-trifluoromethyl-quinoline 29 (250 mg, 0.61 mmol) was dissolved in DMF anhydrous (10 mL) and the solution cooled to 0° C. for 10 min. This solution was added via syringe to the first reaction mixture at 0° C. for 15 min. The reaction mixture was stirred 1.75 h at room temperature (orange). Water (50 mL) was added and the solution was extracted with EtOAc (3×100 mL). The organic layer was washed with water (3×100 mL), brine (3×100 mL), dried over MgSO₄, filtered and evaporated to dryness. The crude product was purified by column chromatography on silica using as eluent CH₂Cl₂:MeOH=98:2. 5-((4-(7-(Trifluoromethyl)quinolin-4-ylthio) methyl)phenyl)methoxy)-2-morpholinomethyl)-4H-pyran-4-one EHT 2218 was obtained (150 mg, 46% yield) as a white solid.

The structure of compound ex 38 is presented below:

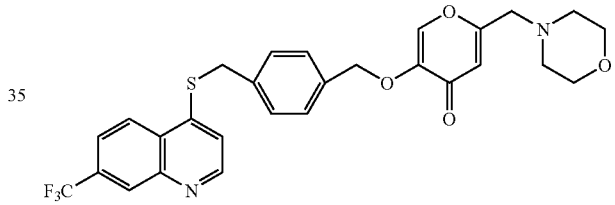

MW: 542.58; Yield: 46%; White solid; Mp: 52.1° C. R_f: 0.25 (CH₂Cl₂:MeOH=98:2). ¹H-NMR (CDCl₃, δ): 2.55 (m, 4H, 2×CH₂—N), 3.38 (s, 2H, —CH₂N), 3.74 (t, J=4.6 Hz, 4H, 2×CH₂—O), 4.37 (s, 2H, —SCH₂), 5.05 (s, 2H, —OCH₂), 6.49 (s, 2H, C═CH), 7.30 (d, J=4.8 Hz, 2H, ArH), 7.44 (q, 4H, J=8.2 Hz, ArH), 7.58 (s, 1H, ArH), 7.73 (dd, 1H, J=8.8 Hz, J=1.8 Hz, ArH), 8.25 (d, 1H, J=8.8 Hz, ArH), 8.38 (s, 1H, ArH), 8.78 (d, 1H, J=4.8 Hz, ArH). MS-ESI m/z (rel. Int.): 542.9 ([MH]⁺, 90), 332.0 (30), 228.9 (100). HPLC: Method A, detection UV 254 nm, EHT 2218 RT=4.60 min, peak area 95.4%.

Example 39 tert-Butyl 4-((5-(5-(7-(trifluoromethyl)quinolin-4-ylthio)pentyloxy)-4-oxo-4H-pyran-2-yl)methyl)piperazine-1-carboxylate (EHT 9358)

tert-Butyl 4-((5-hydroxy-4-oxo-4H-pyran-2-yl)methyl) piperazine-1-carboxylate 23 (5.0 g, 16.1 mmol), Cs₂CO₃ (5.3 g, 16.1 mmol) and anhydrous DMF (20 mL) were charged in a 250 ml round-bottomed flask equipped with a magnetic stirrer under inert atmosphere. 4-(5-Bromopentylthio)-7-(trifluoromethyl)quinoline 25 (5.8 g, 15.3 mmol) and DMF (10 mL) was added and the reaction mixture was stirred for 3 h at 90° C. After evaporation of DMF, the compound was dried under vacuum and precipitated in EtOAc (70 mL). The precipitate was washed with water (3×20 mL) and was filtered to give after drying tert-Butyl 4-((5-(5-(7-(trifluoromethyl)quinolin-4-ylthio)pentyloxy)-4-oxo-4H-pyran-2-yl)methyl)piperazine-1-carboxylate EHT 9358 (7.0 g, 75% yield) as a white powder.

The structure of compound ex 39 is presented below:

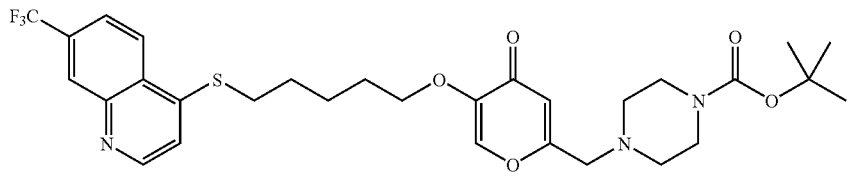

MW: 607.68; Yield: 77%; White solid; Mp: 182.5° C. $^1$H-NMR (CDCl$_3$, δ): 1.46 (s, 9H, tBu), 1.67-1-95 (m, 6H, CH$_2$—CH$_2$—CH$_2$), 2.46 (t, J=4.8 Hz, 4H, N—CH$_2$), 3.15 (t, J=7.2 Hz, 4H, S—CH$_2$), 3.38 (s, 2H, O—CH$_2$), 3.46 (t, J=4.8 Hz, 4H, N—CH$_2$), 3.90 (t, J=6.2 Hz, 2H, O—CH$_2$), 6.46 (s, 1H, C=CH), 7.27 (s, 1H, ArH), 7.57 (s, 1H, ArH), 7.71 (dd, J=8.8 Hz, J=1.8 Hz, 1H, ArH), 8.24 (d, J=8.8 Hz, 1H, ArH), 8.36 (s, 1H, C=CH), 8.79 (d, J=4.8 Hz, 1H, ArH). MS-ESI m/z (rel.Int.): 508 (100%, [MH—COOtBu]$^+$). HPLC: Method A, detection UV 254 nm, RT=4.80 min, peak area 99.5%.

Example 40 tert-Butyl 4((5-(5-(7-chloroquinolin-4-yloxy)pentyloxy)-4-oxo-4H-pyran-2-yl)methyl)piperazine-1-carboxylate (EHT 2580)

tert-Butyl 4-(5-hydroxy-4-oxo-4H-pyran-2-yl)methyl)piperazine-1-carboxylate 23 (0.95 g, 3.0 mmol), Cs$_2$CO$_3$ (1.1 g, 3.2 mmol) and anhydrous DMF (7 mL) were charged in a 50 ml round-bottomed flask equipped with a magnetic stirrer under inert atmosphere. 4-(5-Bromopentyloxy)-7-chloroquinoline 33 (1.00 g, 3.0 mmol) was added and the reaction mixture was stirred for 3 h at 90° C. After evaporation of DMF, the reaction mixture was poured in 50 mL of H$_2$O, extracted with EtOAc (2×100 mL). The organic layer was washed with brine (2×20 mL), dried over MgSO$_4$, filtered and evaporated to dryness. The crude compound was purified by column chromatography (deactivated SiO$_2$:CH$_2$Cl$_2$:triethylamine=98:2 to CH$_2$Cl$_2$:MeOH=95:5; purification: CH$_2$Cl$_2$:MeOH=99:1 to 97.5:2.5) to give after evaporation tert-butyl. 4-((5-(5-(7-chloroquinolin-4-yloxy)pentyloxy)-4-oxo-4H-pyran-2-yl)methyl)piperazine-1-carboxylate EHT 2580 (1.2 g, 72% yield) as a white powder.

The structure of compound ex 40 is presented below:

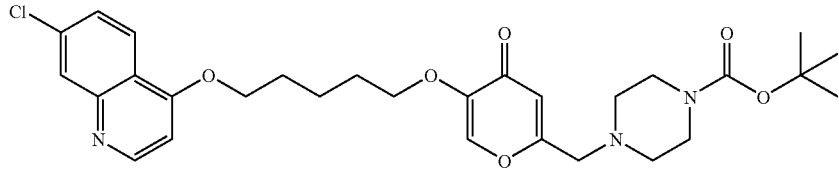

MW: 558.07; Yield: 72%; Beige Solid; Mp=130.2° C. R$_f$: 0.4 (CH$_2$Cl$_2$:MeOH=95:5). $^1$H-NMR (CDCl$_3$, δ): 1.46 (s, 9H, CCH$_3$), 1.72-1.80 (m, 2H, C—CH$_2$), 1.91-2.04 (m, 4H, C—CH$_2$), 2.47 (t, J=4.2 Hz, 4H, N—CH$_2$), 3.38 (s, 2H, N—CH$_2$), 3.46 (t, J=4.2 Hz, 4H, N—CH$_2$), 3.93 (t, J=5.9 Hz, 4H, O—CH$_2$), 4.21 (t, J=5.9 Hz, 4H, O—CH$_2$), 6.45 (s, 1H, C=CH), 6.71 (dd, J=5.2 Hz, J=1.3 Hz, 1H, ArH), 7.29 (d, J=1.9 Hz, 1H, ArH), 7.44 (ddd, J=8.9 Hz, J=1.9 Hz, J=1.9Hz, 1H, ArH), 7.58 (d, J=1.7 Hz, 1H, ArH), 8.01 (s, 1H, C=CH), 8.14 (dd, J=8.9 Hz, J=1.3 Hz, 1H, ArH), 8.72 (dd, J=1.6 Hz, J=5.2 Hz, 1H, ArH). $^{13}$C-NMR (CDCl$_3$, δ): 22.6, 28.4, 28.5, 28.8, 43.4, 52.9, 59.3, 68.3, 69.4, 79.9, 100.9, 114.6, 119.9, 123.5, 126.4, 127.8, 135.6, 139.5, 147.9, 149.7, 152.5, 154.6, 161.6, 164.1, 174.3.MS-ESI m/z (rel. Int.): 558/560 ([MH]$^+$, 100). HPLC: Method A, detection UV 254 nm, EHT 2580 RT=4.4 min, peak area 95.7%

Example 41

5-(5-(7-(Trifluoromethyl)quinolin-4-ylthio)pentyloxy)-2-((4-methylpiperazin-1-yl)methyl)-4H-pyran-4-one trihydrochloride (EHT 9241)

5-Hydroxy-2-((4-methylpiperazin-1-yl)methyl)-4H-pyran-4-one hydrobromide 24 (5.2 g, 17.0 mmol) was dissolved in water (40 mL) and Cs$_2$CO$_3$ (7.3 g, 22.4 mmol) in water (20 mL) was added. Aqueous phase was washed with CH$_2$Cl$_2$ (200 mL), then water was evaporated at 40° C. and the cesium salt was drying under vacuum to give a white powder. This derivate, Cs$_2$CO$_3$ (2.5 g, 7.6 mmol) and anhydrous DMF (100 mL) were charged in a 250 ml round-bottomed flask equipped with a magnetic stirrer under inert atmosphere. 4(5-bromopentylthio)-7-(trifluoromethyl)quinoline 25 (5.8 g, 15.3 mmol) was added and the reaction mixture was stirred for 2 h at 90° C. After evaporation of DMF, the reaction mixture was poured in 200 mL of H$_2$O and extracted with CH$_2$Cl$_2$ (2×300 mL). The organic layer was washed with brine (2×30 mL), dried over MgSO$_4$, filtered and evaporated to dryness. The crude compound was purified by column chromatography (SiO$_2$; CH$_2$Cl$_2$:MeOH=99.5:0.5 to 95:5) to give after evaporation a pure solid (4.3 g, 55% yield). The compound was dissolved in EtOH (150 mL), HCl 1M in EtOH (33 mL, 33.0 mmol) was added and the reaction mixture stirred for 0.5 h at 20° C. After evaporation of EtOH the trihydrochloride salt was dried under vacuum and precipitated in ethanol (50 mL) to give after filtration 5-(5-(7-(trifluoromethyl)quinolin-4- ylthio)pentyloxy)-2-((4-methylpiperazin-1-yl)methyl)-4H-pyran-4-one trihydrochloride EHT 9241 (3.6 g, 38% yield) as a white powder.

The structure of compound ex 41 is presented below:

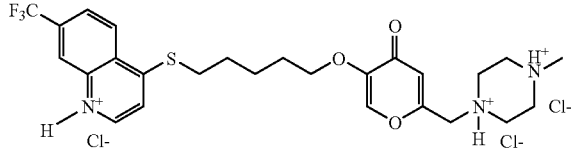

MW: 630.98; Yield: 38%; White powder, Mp: 206.4° C. $R_f$: 0.30 (CH$_2$Cl$_2$:MeOH=8:2). $^1$H-NMR (DMSO d$_6$, δ): 1.59-1.66 (m, 2H, CH$_2$), 1.73-1.90 (m, 4H, CH$_2$), 2.77 (s, 3H, N—CH$_3$), 3.17-3.20 (m, 2H, S—CH$_2$), 3.37-3.54 (m, 8H, N—CH$_2$), 3.85 (t, J=6.0 Hz, 2H, O—CH$_2$), 4.06 (s, 2H, N—CH$_2$), 6.62 (s, 1H, C=CH), 7.91 (d, J=5.8 Hz, 1H, Ar—H), 8.09 (d, J=8.9 Hz, 1H, Ar—H), 8.18 (s, 1H, C=CH), 8.47 (d, J=8.8 Hz, 1H, Ar—H), 8.71 (s, 1H, Ar—H), 9.07 (d, J=5.7 Hz, 1H, Ar—H), 11.83 (s, 3H, NH$^+$). MS-ESI m/z (rel. Int.): 522.2 ([MH]$^+$, 100). HPLC: Method A, Detection UV 254 nm, EHT 9241_RT=4.30 min, peak area 99.6%.

Preparation of EHT 0872 and EHT 8560.

Example 42

5-(5-(7-Chloroquinolin-4-yloxy)pentyloxy)-2-((piperazin-1-yl)methyl)-4H-pyran-4-one trihydrochloride (EHT 0872)

tert-Butyl 4-((5-(5-(7-chloroquinolinyloxy)pentyloxy)-4-oxo-4H-pyran-2-yl)methyl)piperazine-1-carboxylate EHT 2580 (0.8 g, 1.4 mmol) and EtOH (10 ml) was charged in a 100 mL round-bottomed flask equipped with a magnetic stirrer. Anhydrous HCl 2 M in EtOH (7.2 ml, 14 mmol) was added dropwise at 50° C. The reaction mixture was stirred for 2 h at room temperature. The reaction mixture was evaporated in vacuo. EtOH (10 mL) was added then evaporated. This operation was done tree time. After evaporation of EtOH the trihydrochloride salt was dried under vacuum and crystallised in EtOH (20 mL) to give after 5 days and filtration 5-(5-7-chloroquinolin-4-yloxy)pentyloxy)-2-((piperazin-1-yl)methyl)-4H-pyran-4-one trihydrochloride EHT 0872 (400 mg, 50% yield) as a white powder.

The structure of compound ex 42 is presented below:

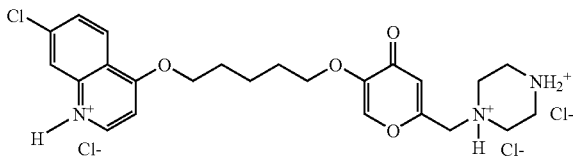

MW: 567.33; Yield: 50%; white solid; Mp: 164.7° C. $R_f$: 0.15 (CH$_2$Cl$_2$:MeOH=9:1). $^1$H-NMR (DMSO d$_6$, δ): 1.64-1-66 (m, 2H, CH$_2$), 1.79-1-81 (m, 2H, CH$_2$), 1.96-1-98 (m, 2H, CH$_2$), 3.20-3.40 (m, 8H, N—CH$_2$), 3.87 (t, J=5.6 Hz, 2H, O—CH$_2$), 4.17 (s, 2H, N—CH$_2$), 4.58 (t, J=5.6 Hz, 2H, O—CH$_2$), 6.67 (s, 1H, C=CH), 7.59 (d, J=6.6 Hz, 1H, ArH), 7.91 (d, J=9.0 Hz, 1H, ArH), 8.21 (s, 1H, ArH), 8.36 (d, J=9.0 Hz, 1H, ArH), 8.45 (s, 1H, C=CH), 9.22 (d, J=6.5 Hz, 1H, ArH), 9.91 (s, 2H, NH$_2^+$). MS-ESI m/z (rel. int.): 458.1 ([MH]$^+$, 100). HPLC: Method A, detection UV 254 nm, EHT 0872 RT=3.80 min, peak area 99.6%.

Example 43

5-(5-(7-(Trifluoromethyl)quinolin-4-ylthio)pentyloxy)-2-((piperazin-1-yl)methyl)-4H-pyran-4-one trihydrochloride (EHT 8560)

tert-Butyl 4-((5-(5-(7-(trifluoromethyl)quinolin-4-ylthio)pentyloxy)-4-oxo-4H-pyran-2-yl)methyl)piperazine-1-carboxylate EHT 9358 (7.0 g, 11.5 mmol) and EtOH (60 ml) were charged in a 250 mL round-bottomed flask equipped with a magnetic stirrer. Anhydrous HCl 1 M in EtOH (60 ml, 60 mmol) was added dropwise at 50° C. The reaction mixture was stirred for 3 h at room temperature. The reaction mixture was evaporated in vacuo. EtOH (30 mL) was added then evaporated.

This operation was done thrre time. After evaporation of EtOH the trihydrochloride salt was dried under vacuum and crystallised in EtOH (200 mL) to give after filtration 5-(5-(74trifluoromethyl)quinolin-4-ylthio)pentyloxy)-2-((piperazin-1-yl)methyl)-4H-pyran-4-one trihydrochloride EHT 8560 (4.5 g, 63% yield) as a white powder.

The structure of compound ex 43 is presented below:

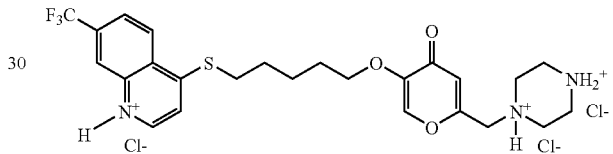

MW: 616.95; Yield: 63%; White solid; Mp: 204° C. $R_f$: 0.15 (CH$_2$Cl$_2$:MeOH=9:1). $^1$H-NMR (DMSO d$_6$, δ): 1.61-1-66 (m, 2H, CH$_2$), 1.75-1-87 (m, 4H, CH$_2$), 3.35-3.45 (m, 10H, N—CH$_2$, S—CH$_2$), 3.86 (t, J=6.2 Hz, 2H, O—CH$_2$), 4.19 (s, 2H, N—CH$_2$), 6.68 (s, 1H, C=CH), 7.88 (d, J=5.6 Hz, 1H, ArH), 8.07 (dd, J=8.9 Hz, J=1.7 Hz, 1H, ArH), 8.19 (s, 1H, C=CH), 8.46 (d, J=8.8 Hz, 1H, ArH), 8.65 (s, 1H, ArH), 9.06 (d, J=5.5 Hz, 1H, ArH), 9.87 (s, 2H, NH$_2^+$), 11.52 (s, 2H, NH$^+$). MS-ESI m/z (rel. Int.): 508 ([MH]$^+$, 100). HPLC: Method A, detection UV 254 nm, EHT 8560 RT=4.20 min, peak area 99.6%.

Preparation of EHT 3980, EHT 5743, EHT 0785, EHT 0566, EHT 8366, EHT 3664 and EHT 4495.

General Procedures:

Method C (in CHCl$_3$):

5-5-(7-(Trifluoromethyl)quinolin-4-ylthio)pentyloxy)-2-((piperazin-1-yl)methyl)-4H-pyran-4-one (free base of EHT 8560) (0.15 g, 0.3 mmol) was charged in a 10 ml round-bottomed flask equipped with a magnetic stirrer. Anhydrous CHCl$_3$ (3 mL) and triethylamine (125 μL, 0.9 mmol) were successively added. After 30 min at 0° C., reagent (0.35 mmol) in CHCl$_3$ (200 μL) was added slowly dropwise. The reaction mixture was stirred for 15 h at room temperature. The reaction mixture was poured in 10 mL of brine and was extracted with CH$_2$Cl$_2$ (50 mL). The organic layer was dried over MgSO$_4$, filtered and evaporated to dryness. The crude compound was purified by column chromatography (SiO$_2$; CH$_2$Cl$_2$:MeOH=99:1 to 95:5) to give after evaporation of solvents the desired compound.

Example 44

5-(5-(7-(Trifluoromethyl)quinolin-4-ylthio)pentyloxy)-2-((4-acetylpiperazin-1-ylmethyl)-4H-pyran-4-one (EHT 3980)

The compound was prepared according to method C using acetyl chloride (28 mg, 0.35 mmol). After purification the title compound was dried under vacuum to give EHT 3980 (150 mg, 90% yield) as a wihite solid.

The structure of compound ex 44 is presented below:

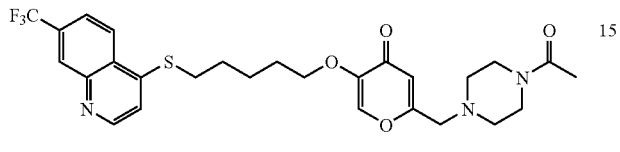

MW: 549.61; Yield: 90%; White solid, Mp: 99.5° C. $R_f$: 0.35 (CH$_2$Cl$_2$:MeOH=95:5). $^1$H-NMR (CDCl$_3$, δ): 1.69-1.77 (m, 2H, CH$_2$), 1.85-1.95 (m, 4H, CH$_2$), 2.09 (s, 3H, CH$_3$), 2.48-2.54 (m, 4H, N—CH$_2$), 3.15 (t, J=7.2 Hz, 2H, S—CH$_2$), 3.40 (s, 2H, N—CH$_2$), 3.50 (t, J=4.9 Hz, 2H, N—CH$_2$), 3.65 (t, J=4.9 Hz, 2H, N—CH$_2$), 3.90 (t, J=6.2 Hz, 2H, O—CH$_2$), 6.47 (s, 1H, C=CH); 7.27 (d, J=4.9 Hz, 1H, Ar—H), 7.59 (s, 1H, C=CH), 7.71 (dd, J=8.8 Hz, J=1.7 Hz, 1H, Ar—H), 8.24 (d, J=8.8 Hz, 1H, Ar—H), 8.36 (s, 1H, Ar—H), 8.78 (d, J=4.8 Hz, 1H, Ar—H). MS-ESI m/z (rel. int.): 550.1 ([MH]$^+$, 100). HPLC: Method A, Detection UV 254 nm, EHT 3980_RT=4.30 min, peak area 96.1%.

Example 45

4-((5-(5-(7-(Trifluoromethyl)quinolin-4-ylthio)pentyloxy)-4-oxo-4H-pyran-2-yl)methyl)-N,N-diethylpiperazine-1-carboxamide (EHT 5743)

The compound was prepared according to method C using diethylcarbamyl chloride (48 mg, 0.35 mmol). After purification the title compound was dried under vacuum to give EHT 5743 (180 mg, 98% yield) as a white solid.

The structure of compound ex 45 is presented below:

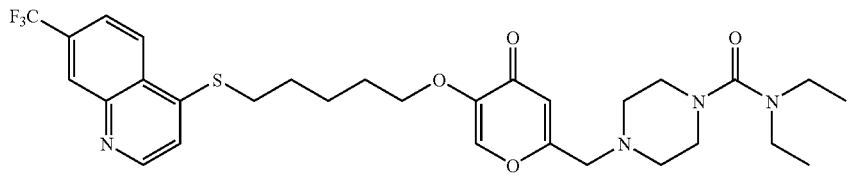

MW: 606.70; Yield: 98%; White solid, Mp: 393.1° C. $R_f$: 0.35 (CH$_2$Cl$_2$:MeOH=95:5). $^1$H-NMR (CDCl$_3$, δ): 1.12 (t, J=7.1 Hz, 6H, CH$_3$), 1.69-1.77 (m, 2H, CH$_2$), 1.84-1.93 (m, 4H, CH$_2$), 2.53 (t, J=4.7 Hz, 4H, N—CH$_2$), 3.12-3.24 (m, 6H, S—CH$_2$, C—CH$_2$), 3.27 (t, J=4.7 Hz, 4H, N—CH$_2$), 3.40 (s, 2H, N—CH$_2$), 3.90 (t, J=6.2 Hz, 2H, O—CH$_2$), 6.46 (s, 1H, C=CH), 7.27 (d, J=4.9 Hz, 1H, Ar—H), 7.61 (s, 1H, C=CH), 7.70 (dd, J=8.8 Hz, J=1.8 Hz, 1H, Ar—H), 8.23 (d, J=8.7 Hz, 1H, Ar—H), 8.35 (s, 1H, Ar—H), 8.78 (d, J=4.8 Hz, 1H, Ar—H). MS-ESI m/z (rel. Int.): 607.2 ([MH]$^+$, 100). HPLC: Method A, Detection UV 254 nm, RT=4.55 min, EHT 5743_peak area 98.7%.

Example 46

5-(5-(7-(Trifluoromethyl)quinolin-4-ylthio)pentyloxy)-2-((4-(pivaloyl)piperazin-1-yl)methyl)-4H-pyran-4-one (EHT 0785)

The compound was prepared according to method C using trimethylacetyl chloride (42 mg, 0.35 mmol). After purification the title compound was dried under vacuum to give EHT 0785 (100 mg, 56% yield) as a white solid.

The structure of compound ex 46 is presented below:

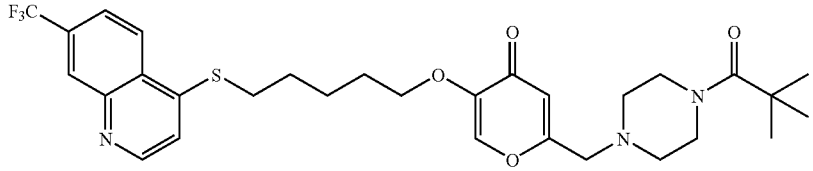

MW: 591.68; Yield: 56%; White solid, Mp: 116.6° C. $R_f$: 0.40 (CH$_2$Cl$_2$:MeOH=95:5). $^1$H-NMR (CDCl$_3$, δ): 1.27 (s, 9H, CH$_3$), 1.69-1.76 (m, 2H, CH$_2$), 1.84-1.93 (m, 4H, CH$_2$), 2.52 (t, J=4.9 Hz, 2H, N—CH$_2$), 3.15 (t, J=7.2 Hz, 2H, S—CH$_2$), 3.39 (s, 2H, N—CH$_2$), 3.69 (t, J=4.7 Hz, 4H, N—CH$_2$), 3.90 (t, J=6.2 Hz, 2H, O—OH$_2$), 6.47 (s, 1H, C=CH), 7.27 (d, J=4.9 Hz, 1H, Ar—H), 7.60 (s, 1H, C=CH), 7.70 (dd, J=8.8 Hz, J=1.8 Hz, 1H, Ar—H), 8.22 (d, J=8.8 Hz, 1H, Ar—H), 8.36 (s, 1H, Ar—H), 8.78 (d, J=4.8 Hz, 1H, Ar—H). MS-ESI m/z (rel. Int.): 592.1 ([MH]$^+$, 100). HPLC: Method A, Detection UV 254 nm, RT=4.61 min, EHT 0785 peak area 98.3%.

Example 47

4-((5-(5-(7-(Trifluoromethyl)quinolin-4-ylthio)pentyloxy)-4-oxo-4H-pyran-2-yl)methyl)-N,N-di-isopropylpirerazine-1-carboxamide (EHT 0566)

The compound was prepared according to method C using diisopropylcarbamoyl chloride (58 mg, 0.35 mmol). After purification the title compound was dried under vacuum to give EHT 0566 (120 mg, 63% yield) as a pale oil.

The structure of compound ex 47 is presented below:

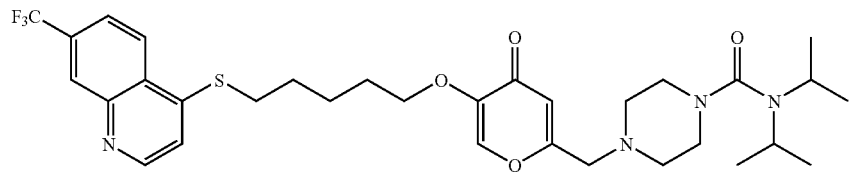

MW: 634.75; Yield: 63%; Pale oil. $R_f$: 0.35 ($CH_2Cl_2$:MeOH=95:5). $^1$H-NMR ($CDCl_3$, δ): 1.27 (d, J=6.7 Hz, 12H, $CH_3$), 1.69-1.77 (m, 2H, $CH_2$), 1.84-1.89 (m, 4H, $CH_2$), 2.54 (t, J=4.6 Hz, 4H, N—$CH_2$), 3.12-3.18 (m, 6H, N—$CH_2$, S—$CH_2$), 3.40 (s, 2H, N—$CH_2$), 3.61 (h, J=6.7 Hz, 2H, CH), 3.90 (t, J=6.2 Hz, 2H, O—$OH_2$), 6.46 (s, 1H, C=CH), 7.27 (d, J=4.9 Hz, 1H, Ar—H), 7.61 (s, 1H, C=CH), 7.70 (dd, J=8.8 Hz, J=1.7 Hz, 1H, Ar—H), 8.23 (d, J=8.8 Hz, 1H, Ar—H), 8.35 (s, 1H, Ar—H), 8.78 (d, J=4.8 Hz, 1H, Ar—H). MS-ESI m/z (rel. Int.): 635.2 ([MH]$^+$, 100). HPLC: Method A, Detection UV 254 nm, EHT 0566_RT=4.78 min, peak area 98.1%.

Example 48

5-(5-(7-(Trifluoromethyl)quinolin-4-ylthio)pentyloxy)-2-((4-Methylsulfonylpiperazin-1-yl)methyl)-4H-pyran-4-one (EHT 8366)

The compound was prepared according to method C using mesyl chloride (42 mg, 0.35 mmol). After purification the compound was dried under vacuum to give EHT 8366 (80 mg, 45% yield) as a white solid.

The structure of compound ex 48 is presented below:

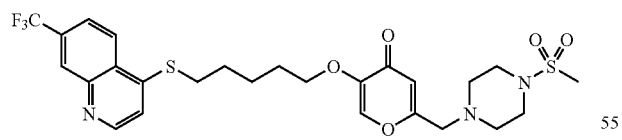

MW: 585.66; Yield: 45%; white solid, Mp: 66.3° C. $R_f$: 0.35 ($CH_2Cl_2$:MeOH=95:5). $^1$H-NMR ($CDCl_3$, δ): 1.69-1.77 (m, 2H, $CH_2$), 1.84-1.94 (m, 4H, $CH_2$), 2.65 (t, J=4.9 Hz, 4H, N—$CH_2$), 2.80 (s, 3H, $CH_3$), 3.15 (t, J=7.2 Hz, 2H, S—$CH_2$), 3.27 (t, J=4.7 Hz, 2H, N—$CH_2$), 3.43 (s, 2H, N—$CH_2$), 3.89 (t, J=6.2 Hz, 2H, O—$CH_2$), 6.46 (s, 1H, C=CH), 7.27 (d, J=4.8 Hz, 1H, Ar—H), 7.58 (s, 1H, C=CH), 7.71 (dd, J=8.8 Hz, J=1.7 Hz, 1H, Ar—H), 8.24 (d, J=8.8 Hz, 1H, Ar—H), 8.35 (s, 1H, Ar—H), 8.78 (d, J=4.8 Hz, 1H, Ar—H). MS-ESI m/z (rel. Int.): 586.0 ([MH]$^+$, 100). HPLC: Method A, Detection UV 254 nm, EHT 8366 RT=4.60 min, peak area 98.5%.

Example 49

4-((5-(5-(7-trifluoromethyl)quinolin-4-ylthio)pentyloxy)oxo-4H-pyran-2-yl)methyl-N-tert-butylpiperazine-1-carboxamide (EHT 3664)

The compound was prepared according to method C using tert-butyl isocyanate (36 mg, 0.35 mmol). After purification the title compound was dried under vacuum to give EHT 3664 (130 mg, 71% yield) as a white solid.

The structure of compound ex 49 is presented below:

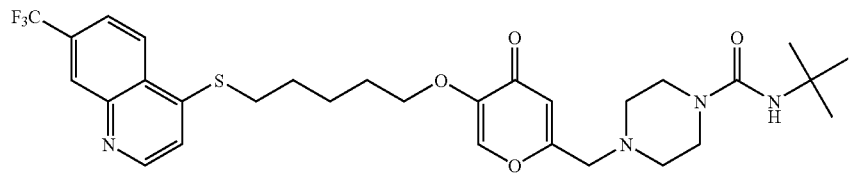

MW: 606.70; Yield: 71%; White solid, Mp: 154.4° C. $R_f$: 0.35 ($CH_2Cl_2$:MeOH=95:5). $^1$H-NMR ($CDCl_3$, δ): 1.35 (s, 9H, $CH_3$), 1.69-1.77 (m, 2H, $CH_2$), 1.85-1.95 (m, 4H, $CH_2$), 2.50 (t, J=4.9 Hz, 4H, N—$CH_2$), 3.14 (t, J=7.2 Hz, 2H, S—$CH_2$), 3.35-3.38 (m, 6H, N—$CH_2$), 3.89 (t, J=6.2 Hz, 2H, O—$CH_2$), 4.45 (s, 1H, NH), 6.45 (s, 1H, C=CH), 7.26 (d, J=4.9 Hz, 1H, Ar—H), 7.59 (s, 1H, C=CH), 7.70 (dd, J=8.8 Hz, J=1.6 Hz, 1H, Ar—H), 8.23 (d, J=8.8 Hz, 1H, Ar—H), 8.36 (s, 1H, Ar—H), 8.78 (d, J=4.8 Hz, 1H, Ar—H). MS-ESI m/z (rel. Int.): 508.1 ([MH]$^+$, 100). HPLC: Method A, Detection UV 254 nm, EHT 3664 RT=4.60 min, peak area 99.6%.

Example 50

4-((5-(5-(7-(Trifluoromethyl)quinolin-4-ylthio)pentyloxy4-oxo-4H-pyran-2-yl)methyl)-N-methylpiperazine-1-carboxamide (EHT 4495)

The compound was prepared according to method C using methylcarbamyl chloride (35 mg, 0.35 mmol). After purification the title compound was dried under vacuum to give EHT 4495 (100 mg, 59% yield) as a pale oil.

The structure of compound ex 50 is presented below:

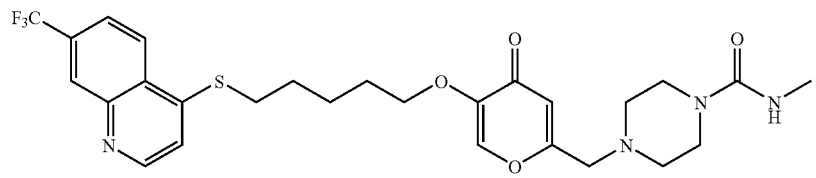

MW: 564.62; Yield: 59%; Pale oil. $R_f$: 0.35 ($CH_2Cl_2$:MeOH=95:5). $^1$H-NMR ($CDCl_3$, δ): 1.69-1.77 (m, 2H, $CH_2$), 1.84-1.94 (m, 4H, $CH_2$), 2.48 (t, J=4.9 Hz, 4H, N—$CH_2$), 3.15 (t, J=7.2 Hz, 2H, S—$CH_2$), 3.38 (s, 2H, N—$CH_2$), 3.51 (t, J=4.4 Hz, 4H, N—$CH_2$), 3.70 (s, 3H, $CH_3$), 3.90 (t, J=6.2 Hz, 2H, O—$CH_2$), 6.46 (s, 1H, C=CH), 7.27 (d, J=4.9 Hz, 1H, Ar—H), 7.58 (s, 1H, C=CH), 7.71 (dd, J=8.8 Hz, J=1.8 Hz, 1H, Ar—H), 8.24 (d, J=8.8 Hz, 1H, Ar—H), 8.35 (s, 1H, Ar—H), 8.78 (d, J=4.8 Hz, 1H, Ar—H). MS-ESI m/z(rel. Int.): 566.1 ([MH]$^+$, 100). HPLC: Method A, Detection UV 254 nm, EHT 4495 RT=4.40 min, peak area 99.1%.

Example 51

Pharmacology

This example discloses the various assay conditions used to illustrate the biological activity of the compounds.

Material and Methods

1. Reference Compounds

A series of in vitro tests was designed to screen the various compounds and evaluate their anti-proliferative, anti-tumoral and anti-angiogenic potential. CAI (carboxyamidotriazole; L651582, Merck Institute for Therapeutic Research), Paclitaxel (taxol; Bristol Myers Squibb), 2-Methoxyestradiol (2Me, Panzem™; EntreMed) and SU-6668 (Sugen) were included as positive controls.

Reference CAI is a compound originally developed as a coccidiostat (U.S. Pat. No. 4,590,201). CAI has been shown later by the NCI to be a synthetic inhibitor of both nonvoltage- and voltage-gated calcium pathways. It demonstrated inhibition of tumor cell motility, adhesion, metastatic potential, and growth in vitro in a number of human tumor cell lines at concentrations from 1 to 10 μM. CAI was also demonstrated to inhibit proliferation, migration and adhesion of several human endothelial cells. Moreover, inhibition of both HUVEC vascular tube formation on matrigel and retardation of microvessel outgrowth in the rat aorta ring were shown. Finally, in vivo inhibition of angiogenesis in the chicken chorioallantoic membrane assay at concentrations from 10 to 20 μM was also demonstrated.

Reference 2ME is an endogenous metabolite of estradiol that has been demonstrated to inhibit both tumor growth and angiogenesis in vivo. However, in addition to its antiangiogenic activity, 2-ME induces apoptosis in actively proliferating cells and exhibits general non-specific antiproliferative effects against a wide range of human cancer cell cultures. It also has a limited oral bioavailability in mice and is rapidly cleared following administration. In Phase I and Phase II oncology trials, orally administered 2ME has demonstrated anticancer activity in patients with breast cancer, prostate cancer and multiple myeloma, and was well tolerated. Currently, 2ME is in Phase I clinical trials for breast cancer and in Phase II trials for the blood cancer multiple myeloma. Results in preclinical models with ocular implants of 2ME have demonstrated that it may inhibit neovascularization of age-related macular degeneration (ARMD).

Reference SU6668 is a selective inhibitor of receptor tyrosine kinases (RTKS) developed for the treatment of various cancers (ovarian, prostate and brain cancers. SU6668 inhibits angiogenesis required for tumor growth and metastasis via binding to receptors of vascular endothelial (VEGF), platelet-derived (PDGF) and fibroblast growth factor (FGF), which are involved in the formation of new blood vessels. In preclinical tumor models, SU6668 completely inhibits target receptor phosphorylation and induces tumor regression through angiogenesis inhibition. An oral formulation was in Phase II/III clinical trials in 2000. No development was reported since then.

2. In Vitro Assays a. Study of the Compounds Influence on the Actin Cytoskeleton Quiescence of Swiss 3T3 cells: Cells are seeded at high density on coverslips in 5% FCS medium (special weak FCS). When cells become quiescent (after 6-10 days of culture), the medium is removed (a few microliters remaining in the well) and replaced with serum free medium. Cells are placed in the incubator overnight. Ideally, cells will have few, if any, actin stress fibers and a thin band of cortical actin around the periphery.

Treatment of the cells with test compounds: Quiescent cells are treated for 30 min. with various concentrations of the compounds. Cells can subsequently be treated with a cocktail of test compound+inducer (see below paragraph). After treatment, Immunofluorescence can be performed.

Treatment of the cells with various inducers of small G proteins: Small G proteins pathways can be specifically activated, impacting on the cell cytoskeleton (Takai et al, *Physiol. Rev.*, 2001). The Rac pathway controlling the formation of membrane ruffles can be activated by PDGF, insulin, Bombesin (Ridley et al, *Cell,* 1992, Nobes et al, *J. Cell Sci,* 1995) and osmotic stress (Di Ciano et al, *Am J Physiol Cell Physiol,* 2002). The Rho signaling pathway can be notably activated by LPA (Ridley and Hall, Cell, 1992).

| Inducer | Final concentration | Ruffles (incubation time) |
|---|---|---|
| Bombesin (Sigma) | 10 nM | 10 min. |
| PDGF (Preprotech) | 3 ng/ml | 10 min. |
| Insulin (Sigma) | 1 μg/ml | 10 min. |
| Osmotic shock ($H_2O$) | 50% | 10 min. |

Immunofluorescence

Fixation and permeabilization: Medium is aspirated from the culture wells and replaced with fixation buffer (BRB80: 80 mM KPipes pH 6.8, 2 mM $MgCl_2$, 5 mM EGTA, 0.3% paraformaldehyde). Cells are incubated for 2×10 min. at room temperature. The fixation buffer is removed and replaced with permeabilization buffer (PBS, 2% BSA, 0.1× saponin). Plates are incubated for 1 h at room temperature or 16 h at 4° C.

Labeling: Fixed and permeabilized cells are incubated with anti-tubulin primary antibody (Yol 1/34; Abcys) diluted in permeabilization buffer for 1 h. This is followed by 5 washes with permeabilization buffer. The coverslips are incubated for 30 min to 1 h with goat anti-rat FITC secondary (Jackson Immunoresearch) antibody and phalloidin-TRITC (Sigma) which binds filamentous actin. This is followed by 5 washes in permeabilization solution. Coverslips are then fixed on microscope slides with Immuno-Fluore (ICN) mounting solution. Mounting is allowed to dry at 37° C. for 1 h.

Quantification of the effect of the compounds: The total number of cells is counted under the microscope (at least three different fields, e.g. between 100 and 200 cells). The number of cells bearing the morphological features of interest is evaluated. The percentage of cells bearing the morphological features of interest is then calculated.

b. Cell Culture and Cell Viability Assay

In order to determine a compound's effect on cell viability, microculture tetrazolium assays (MTT) were performed as described by Carmichael et al. (1996) with modifications. Four human tumoral cell lines, namely HCT116 colon adenocarcinoma, H460 lung carcinoma, MCF-7 and MDA-MB-231 breast carcinoma cell lines, DLD1 colorectal adenocarcinoma, HeLa adenocarcinoma, HepG2 hepatocellular carcinoma. 3 immortalized but non tumorigenic cell lines, namely NIH3T3 mouse fibroblasts (American Type Culture Collection) and primary hepatocytes (Biopredic international), cultured according to their recommendations together with Human Microvasculature Endothelial Cell line HMEC1 (National Center for Infectious Diseases). Briefly, cells were seeded in 48-well plates 24 hours before drug addition. Cells were treated with 0 to 200 µM (11 concentrations) of compound solubilized in DMSO, adjusting the final concentration of DMSO to 1% in the well. 16 hours, and three or six days after treatment, 0.5 mg/ml MTT (Sigma) was added to the medium and cells were incubated for 1-5 hours at 37° C. before solubilization of formazan crystals in 100% DMSO. Absorbance was measured using a spectrophotometer at a wavelength of 550 nm. Data was analyzed using the GraphPad Prism software (GraphPad Software, Inc.), and $IC_{50}$ (dose leading to 50% cell death) was calculated from the dose-response curves.

c. Anchorage-independent Cell Growth Assay in Soft Agar

In order to evaluate the effect of one compound on the capacity of tumour cells to grow without anchorage, HCT116 cells were seeded in soft agar. In contrast to microplate assays which average the drug's effects over an entire cell population, clonogenic assays offer the possibility of distinguishing cytotoxic agents (i.e., decreased colony number) from cytostatic agents (i.e., decreased colony size without decreased colony number; Murphy M. J. et al., 1996). Briefly, 5 $10^3$ HCT116 cells were resuspended in 300 µl of complete medium containing 0.3% soft-agar (Difco) and different concentrations of compound (8 concentrations ranging from 0 to 30 µM). Cells were then poured on a solidified layer of medium containing 0.5% of soft agar plus the compound at the same concentration as in the upper layer. Cells were incubated for 7 days at 37° C. before pictures of each well were taken using a phase contrast microscope (Nikon) and a digital camera (Nikon Coolpix 990). Pictures were subsequently analyzed using free image analysis software from the NIH (ImageJ) allowing determination of clone size and number.

Data were analyzed using the GraphPad Prism software, and $IC_{50}$ (dose leading to a 50% decrease of clone size or number) was calculated from dose-response curves.

d. Migration Assays

Wound Healing Assay

This assay has been described by Nobes & Hall (*J. Cell Biol.*, 1999).

Preparation of REF cells: REF cells are prepared from 15-18 E14 embryos. Briefly, the head, tail and viscerae are removed from the embryo. Only the torso is kept, sliced into small squares, washed, treated with trypsin-EDTA for 20 min. at 37° C., resuspended in medium, counted and plated. After 24 h, the cells are trypsinized and frozen in cryovials. 48 h before the wound healing assay, the cells are plated on coverslips. The day of the experiment, the cells are treated with the test compounds or DMSO alone. After 30 min., a scrape is done in the center of the coverslip using a small pipette tip. The cells are washed and fresh medium containing the compound or the DMSO is added.

Time-Lapse microscopy: The dishes containing the scraped coverslips and the treatment medium, sealed with parafilm is put under a thermostated microscope (37° C.) coupled to a video camera and a computer. Microscope images were collected every 5 minutes and recorded using the OpenLab software. When the assay is terminated (after 4 to 24 hours), pictures and movies are analyzed using the Metamorphe software. The pictures were calibrated (pixel converted to µm), and the velocity and total distance covered were calculated after tracking 7 to 10 single cells on the movies. For that, one point was chosen on one cell and this point is followed on each movie picture. The position of each point was recorded. Data were transferred to Excel, and the average distance and the average velocity were calculated.

Immunofluorescence: Alternatively, after the 30 min. treatment, and scratching, a further incubation of 4 hours can be performed in the incubator and cell morphology can be studied by immunofluorescence.

Fixation and permeabilisation: Medium is aspirated from the culture wells, washed and fixed. Cells are incubated for 2×10 min. at room temperature. The fixation buffer is removed and replaced with permeabilisation buffer. Plates are incubated for 1 h at room temperature or 16 h at 4° C.

Labeling: Fixed and permeabilized cells are incubated with anti-tubulin primary antibody diluted in permeabilization buffer for 1 h. This is followed by 5 washes with permeabilization buffer. The coverslips are incubated for 30 min to 1 h with goat anti-rat. FITC secondary antibody and phalloidin-TRITC which binds filamentous actin. This is followed by 5 washes in permeabilization solution. Coverslips are then fixed on microscope slides with Immuno-Fluore mounting solution. Mounting is allowed to dry at 37° C. for 1 h.

Migration in Boyden Chambers

An essential characteristic of malignant cells is their ability to migrate, invade host tissues and to produce metastases. In order to evaluate the capacity of one compound to affect the ability of tumoral cells to migrate, migration assays were performed using highly invasive tumoral cells MDA-MB-231, endothelial cells HMEC1 or fibroblastic cells NIH3T3. This assay was performed using Falcon HTS Fluoroblock inserts. Culture medium containing Fetal Bovine Serum (FBS; which is used as a chemoattractant) was added to the plate wells and 2 $10^4$ to 7.5 $10^4$ cells resuspended in medium without FBS and with 0.1% BSA were added to each insert well. The compound of interest was added to the medium in both the upper and the lower chambers. Plates were incubated for 16 hours at 37° C. Following incubation, the medium was removed from the upper chamber and the entire insert plate was transferred to a second 24-well plate containing 4 µg/ml Calcein-AM™ in medium containing 0.1% BSA. The plates were incubated for one hour at 37° C., rinsed with Hanks Buffered Saline (HBSS). Fluorescence data were collected using Fluoroskan Ascent FL fluorescence plate reader at an excitation wavelength (Ex) of 485 nm and emission wavelength (Em) of 517 nm. Only those labelled cells that passed through the Matrigel layer and the membrane were detected. Data were analyzed using the GraphPad Prism software and IM50s (dose at which 50% inhibition of cell migration is observed) were calculated.

e. Tubule Formation Assay

The endothelial cell tube formation assay, or tubulogenesis assay, is an in vitro assay that is widely accepted to accurately reflect number of terminal stages of the angiogenic process such as attachment, migration and differentiation into tubular structures. In this model, endothelial cells are cultured on a monolayer of reconstituted basement membrane components (Matrigel) and form, in a few hours, capillary-lilke structure. Therefore, this system is a useful and powerful tool for rapidly screening anti-angiogenic agents by monitoring inhibition of endothelial cells morphogenesis on extracellular matrix.

HMEC-1 cell line is cultured in MCDB-131 medium (Sigma) supplemented with 15% FBS, 10 ng/ml recombinant human epidermal growth factor (Invitrogen) and 1 µg/ml hydrocortisone. Cells are cultured to 70-80% confluence. A 96-well plate was coated with Matrigel® Basement Membrane Matrix (Becton Dickinson). 2 $10^4$ HMEC-1 cells were seeded into each well. The test or control compounds were diluted in DMSO and added to the coated plate. The plate was subsequently incubated for 6 to 8 hours at 37° C., 5% $CO_2$ atmosphere to allow tubule formation. The cells were then incubated with 1.25 µg/ml Calcein AM for 15 minutes at 37° C., 5% $CO_2$. Pictures of each well were taken using a fluorescent microscope and a digital camera (Nikon Coolpix 990). Images were analysed using AngioSys software (TCS Cellworks) that allows quantification of the total tubule length and of the number of junctions, two parameters representative of tubule formation/disruption. Data was analyzed using the GraphPad Prism software, and $IT_{50s}$ (dose leading to 50% inhibition of tubulogenesis) was calculated.

3. In Vivo Assays

In vivo zebrafish angiogenesis model: This assay is a viable and validated whole animal model for screening small molecules that affect blood vessel formation (Serbedzija et al, *Angiogenesis*, 1999). The study was subcontracted to Phylonix Pharmaceutical, Cambridge, Mass., USA.

Drug treatment: Intersegmental vessels (ISVs) in zebrafish are well accepted as angiogenic vessels, and they are easily observed using microscopy. By 20 hpf stage, the major vasculogenic vessels (dorsal aorta and caudal vein) have developed. By 48 hours post fertilization (hpf), ISVs have formed by sprouting from the dorsal aorta and caudal vein. Therefore, 20 hpf was used as the starting point and 48 hpf as the end point for drug treatment. Zebrafish embryos staged at 20 hpf were incubated with compound solution at 28° C. for 28 hours in 6-well plates, 20 embryos per well. Embryos treated with 1% DMSO and 5 µM Flavopiridol were used as negative and positive controls, respectively.

Microscopy: All light microscopy studies were performed using a ZEISS Stemi 2000-C stereomicroscope (Zeiss), equipped with a digital spot camera (Diagnostic Instruments Inc.). Images were further processed and analyzed using Adobe Photoshop 7.0 (Adobe).

Whole mount EAP staining: Embryos were fixed in 4% PFA for 2 hours at room temperature, and dehydrated in 100% ethanol following standard procedures. Embryos were then rehydrated, blocked, and stained with NBT/BCIP. After washing, embryos were examined by microscopy.

Quantitation of anti-angiogenic effects: To quantitate anti-angiogenic effects, 5 well developed trunk ISVs located around the anal pore were selected and morphometric analysis [area (pixel)× signal intensity] was performed using Adobe Photoshop. For each condition, 10 embryos were assessed and the mean value of 10 images was calculated using EXCEL software program (Microsoft Corporation). To calculate the inhibitory effect, the mean value of signal (S) in 5 ISVs in drug treated embryos was divided by mean value of S in DMSO control embryos, and calculated as % inhibition using the following formula:

$$\% \text{ Inhibition} = \left\{ 1 - \left( \frac{S(\text{drug treated})}{S(\text{control})} \right) \right\} \times 100$$

4. Toxicity Assays

Screening Ames Test

The objective of this study was to evaluate the potential of the test items to induce reverse mutation in *Salmonella Typhimurium* (TA 98 and TA 100 strains). The bacterial reverse mutation test is able to identify substances that cause point mutations, by substitution, addition or deletion of one or a few DNA base-pairs. Mutagenic substances can induce reversion in histidine deficient strains which are then able to grow and form colonies in a histidine-limited medium, while non-reverted cannot. This test is performed in the absence and presence of a rat liver metabolising system (S9 mix). Three known mutagens are used to check sensitivity of test system: sodium azide, 2-nitrofluorene and 2-anthramine.

The dose levels per plate were of 10 to 5000 µg. A preliminary toxicity test was performed followed by the mutagenecity test per se.

Screening in vivo rising and repeated-dose toxicity study in rats was performed on 3 rats per compound with the following schedule:

a. day 1 to day 3: 10 mg/kg p.o. per day,
b. day 4 to day 6: 50 mg/kg p.o. per day,
c. day 7 to day 9: 300 mg/kg p.o. per day.

Clinical signs, bodyweight, food consumption, and blood parameters were followed.

Results

1. In Vitro Assays a. Study of the Compounds Influence on the Actin Cytoskeleton In two sets of experiments using quiescent Swiss 3T3 cells, Rac was induced with insulin, bombesin or by osmotic shock, after pretreatment with compounds EHT 1864 and EHT 9241. The results obtained after osmotic shock are presented in FIG. 1. Pre-treatment of quiescent Swiss 3T3 cells with subtoxic doses of EHT 1864 and EHT 9241 dose-dependently prevents formation of ruffles induced by Rac after osmotic shock. First, we could observe that each cell displayed less ruffles, and these ruffles were less rich in actin (decrease of fluorescence labeling). Second, the total number of cells displaying ruffles was decreased upon treatment (see bottom left graph). These results were confirmed by similar experiments where ruffles formation was induced by insulin and bombesin (data not shown). In another system (REF cells) dose-dependent inhibition of lamellipodia/ruffles formation after wounding was observed upon treatment with both compounds.

In conclusion, EHT 1864 and EHT 9241 affect the formation of cytoskeletal structures controlled by Rac.

b. Cell Viability Assay (MTT)

In order to study their effect on cell viability, over 47 test compounds and 5 reference compounds were tested through MTT, in numerous cell lines. Cell viability was assessed after various treatment durations and in different conditions: 16 hours (Table 15), 3 days (Table 14) and 6 days (Table 12), in 10% (Tables 12, 14 and 15) or 0.5% (Table 13, 6 days treatment) Fetal Bovine Serum (FBS). Compounds display activities very comparable to those of reference compounds CAI and 2ME. Best compounds display an activity around 100 times lower to that of Taxol. SU-6668 was shown to be weakly toxic in all cells.

MTT 6 Days in 10% FBS (Table 12; FIG. 2-A)

The compounds have been tested in 3 tumoral cell lines (HCT16, MDA-MB-231 and MCF7) and 2 non tumoral cell lines (endothelial HMEC1 and fibroblasts NIH3T3).

In HCT 116 cells (doubling time approximatively of 24 hours; $0.3<IC_{50}<200$ µM), 24 compounds had $IC_{50s}$ below 4 µM (in each category, all compounds are sorted according to their activity, from the highest to the lowest):

9 compounds display OTHP protections: EHT 8883, EHT 5881, EHT 9376, EHT 1006, EHT 6271, EHT 9140, EHT 6060, EHT 3788 and EHT 1593, 9 compounds display piperazino group at position $R_1$ of the Kojic Acid moiety: EHT 5743, EHT 9358, EHT 0566, EHT 0785, EHT 3980, EHT 4495, EHT 8560 and EHT 9241.

5 compounds display morpholino group at position $R_1$ of the Kojic acid moiety: EHT 5430, EHT 2725, EHT 1864, EHT2272 and EHT 2218, 1 compound displays a piperidino group at position $R_1$ of the kojic acid moiety: EHT 9317, 1 compound displays a chlorine atom at position $R_1$ of the Kojic acid moiety EHT 1494.

In MDA-MB-231 cells (doubling time of 36-48 hours; $IC_{50s}$ from 2.3 µM), 9 compounds have $IC_{50s}$ below 9 µM:
piperazino derivatives: EHT 9358, EHT 8560, EHT 7365, EHT 9241, EHT 3664, EHT 0785 and EHT 5743,
morpholino derivatives: EHT 2218 and EHT 1864.

In HMEC1 cells (doubling time of 48-72 hours; $1.8<IC_{50}<200$ µM), 14 compounds have $IC_{50s}$ below 10 µM:
6 compounds display a OTHP protection at position $R_1$ of the Kojic acid moiety: EHT 3788, EHT 8883, EHT 9376, EHT 6271, EHT 1006 and EHT 4745, 7 compounds display a piperazino group at position $R_1$ of the Kojic Acid moiety: EHT 0566, EHT 8560, EHT 5743, EHT 9241, EHT 7365, EHT 0785 and EHT 3664. Only the activity of compounds EHT 5743 and EHT 0785 is significantly different in HMEC1 and HCT116 cells (20- and 5-fold difference respectively).

1 Compound displays a chlorine atom at position $R_1$ of the Kojic acid moiety: EHT 1494.

Morpholino compounds EHT 1864, EHT 2218, EHT 2272, EHT 2725 and EHT 5430 show an activity significantly different in HMEC1 cells as compared to HCT116 cells (5- to 13-fold). The compounds are most active in HCT116 cells. Inversely, the piperazino derivatives EHT 8560 and EHT 9241 show a more heterogenous activity on the various cell lines tested.

This MTT screening also allowed the definition of the other optimal moieties:
the 5-carbon unconstrained linear linker
the 7-trifluoromethyl-quinoline-4-thiol ring Two classes of compounds were retained for further analysis: "non-selective" piperazino derivatives EHT 8560 & EHT 9241 and "selective" morpholino derivatives EHT 1864 & EHT 2725.

MTT 6 Days in 0.5% FBS (Table 13)

These experiments were performed in order to get rid of the proliferation component of the assay and check the effect of the compounds on cell viability only. Only 7 compounds were tested through MTT in these conditions. No major difference in $IC_{50s}$ was observed between 10% and 0.5% FBS culture conditions. Only a 1- to 2-fold difference was observed, indicating that compounds probably act on cell survival rather than on cell proliferation.

MTT 3 Days in 10% FBS (Table 14; FIG. 2-B)

4 compounds were tested through MTT at 3 days In tumoral colon cell lines (DLD1 & HCT116), in breast tumoral cell lines (MDA-MB-231 & MCF7). They were shown to have activities very close to that of reference compound 5-FluoroUracile. As observed for MTT at 6 days, piperazine derivatives display a more homogenous activity on the various cell lines tested than the morpholino derivatives.

MTT 16 Hours in 10% FBS (Table 15)

4 compounds were tested through MTT at 16 hours in colon tumoral (HCT116), breast tumoral (MDA-MB-231), fibroblasts (NIH3T3) and in hepatocytes (tumoral HepG2 and primary hepatocytes). Interestingly, no major difference was observed between the responses obtained from tumoral and primary hepatocytes.

c. Anchorage-independent Growth Assay

In order to study the compounds' effects on the ability of HCT116 cells to grow independently from anchorage, cells were grown in soft agar in the presence of various concentrations of the compounds. These experiments allowed 1) to rank the compounds according to their potential in affecting the clone size and 2) to evaluate their mode of action (cytotoxic vs cytostatic).

EHT 9376, EHT 9014, EHT 3788 and EHT 1593 all affect the ability of HCT116 to grow independently from anchorage in the micromolar range. The compound showing the highest effect was EHT 9376. The compound showing the lowest effect was EHT 1593. $IC_{50}$ for EHT 9376 is very similar to $IC_{50}$ calculated for reference compound CAI (5.4±1.2 µM against 5.8±1.0 µM respectively) (FIG. 3-B).

In our experiments, CAI was shown to preferentially affect clone size as compared to clone number (FIG. 3-A). This is in accordance with the literature where CAI is described as a cytostatic compound (Wasilenko et al, 1996). Similarly, the best compounds of the invention that were tested preferentially affect clone size.

In conclusion, the compounds described in this invention have a cytostatic mode of action.

d. Migration Assays

In order to directly assess the capacity of the compounds to affect cell migration, two techniques were used: the wound healing and the Boyden chamber migration assays. Compounds were tested through Boyden migration assay, in parallel with reference compound CAI, which is described in the literature as an anti-migratory compound (Kohn E C et al, 1990; Rust W L et al, 2000) and other reference compounds 2ME and SU-6668. The results are presented in FIG. 5.

Wound healing assay: All the experiments have been tested at subtoxic doses. Time lapse microscopy was done for 8 hours (1 picture every 5 minutes). The movies that were generated were analyzed and cells were tracked picture after picture in order to evaluate their velocity and the total distance they covered. The quantifications appear in the graphs on FIG. 4A. From this experiment it is shown that 10 µM EHT 9241 decreases migration of REF cells by 36% and 30 µM EHT 1864 decreases migration of about 48% (velocity and total distance covered).

Migration assay in Boyden chamber: Various cell lines were used for this assay: tumoral (MDA-MB-231), endothelial (HMEC1) and fibroblast (NIH3T3) cell lines. The results obtained for experiments performed on 11 test compounds and 2 reference compounds and using FBS as a chemoattractant are summarized in FIG. 4-B. These experiments show that most of the compounds tested affect various cell lines migration in the low micromolar range.

In HMEC1 cells, compounds showing the highest activity are OTHP compounds EHT 3788 and EHT 9376. They are followed by the morpholino derivative EHT 1864 ($IC_{50}$=7.8±1.7 µM), and the piperazino derivatives EHT 9241 ($IC_{50}$=9.1±1.4 µM), and EHT 8560 ($IC_{50}$=9.5±0.3 µM).

In NIH3T3 cells, best compounds are piperazino derivatives EHT 9241 ($IC_{50}$=4.7±0.6 µM), EHT 7365 ($IC_{50}$=6.1±1.1 µM) and EHT 8560 ($IC_{50}$=10±0.6 µM) followed by morpholino derivatives EHT 7168 ($IC_{50}$=16.4±3.4 µM) and EHT 1864 ($IC_{50}$=20.4±3.5 µM).

In MDA-MB-231 cells, best compounds are EHT 9241 ($IC_{50}$=2.7±1.0 µM), EHT 7365 ($IC_{50}$=3.9±0.8 µM) and EHT 8560 ($IC_{50}$=4.5±2.4 µM) followed by the morpholine derivative EHT 1864 ($IC_{50}$=5.1±1.9 µM).

The effects observed cannot be solely attributed to the toxicity of the compounds, since MTT data at 16 hours (Table 15) indicate $IC_{50s}$ 3- to 25-fold higher depending on the cell line tested.

In conclusion, piperazino derivatives seem to be more potent than morpholino derivatives at inhibiting the cell migration. In addition, best compounds affect migration at concentrations lower than CAI, which is described in the literature as a potent anti-metastatic compound (Wu et al, *Clin. Cancer Res.*, 1997; Wasilenko et al, *Int. J. Cancer*, 1996; Kohn & Liotta, *J. Natl. Cancer Instit.*, 1990; Rust et al, *Anal. Biochem.*, 2000).

Compounds according to the invention are thus potent anti-migratory compounds, and this can be explained by their ability to inhibit the Rac-controlled formation of lamellipodia and ruffles.

e. Tubule Formation Assay

As seen above, the compounds of the present invention and CAI have very close anticancer characteristics (cell proliferation, migration, anchorage independent cell growth). Interestingly, CAI is described in the literature as being both an anticancer and an anti-angiogenic compound (Bauer K S et al, 2000; Krüger E A & Figg W D, 2001). In order to see if our compounds also share anti-angiogenic characteristics-with CAI, a tubulogenesis assay on HMEC1 cells was performed using 33 test compounds.

When plated on Matrigel, HMEC1 cells form vessel-like structures in the presence of medium plus solvent DMSO alone. In contrast, the addition of compounds in culture medium caused a dose-dependent inhibition of Matrigel-induced network formation. $IT_{50}$ for both total tubule length and number of junctions (two parameters which are representative of the tubulogenesis process) were calculated for all the tested compounds using GraphPad Prism. A graph presenting the $IT_{50s}$ obtained for the number of junctions is shown on FIG. 5. $IT_{50s}$ obtained for total tubule length were very similar (data not shown).

The 5 most active compounds were shown to be the following (from most active to least active):

EHT 8560 ($IC_{50}$=17.0±3.6 µM), EHT 9140, EHT 6060, EHT 3788, EHT 5881, EHT 9241 ($IC_{50}$=26.0±8.7 µM). These compounds are 5- to 8-fold more active than reference compound CAI. The highest activity compound is the piperazino derivative EHT 8560. The most active morpholino derivative is EHT 2218 ($IC_{50}$=30.8 µM), followed by EHT 1864 ($IC_{50}$=34.9±3.5 µM), which are 4-fold more active than CAI.

Best compounds are active in the same range as 2ME, although they seem to affect the tubulogenesis process differently. 2ME seems to affect the cells integrity during the treatment when the test compounds only affect the formation of tubules. In our assay, SU-6668 is shown to be weakly potent, which can be explained by the fact that the assay is performed in VEGF and FGF free conditions.

The inhibition of the tubule formation cannot be attributed to compound toxicity since the endothelial cells are treated for only a few hours and the compounds were shown to have only a moderate effect on HMEC1 cells viability through MTU (see Tables 12-15).

f. Conclusion In Vitro Pharmacology

THP compounds were not retained for complete characterization, as these compounds are thought to be poorly bioavailable and highly unstable in vivo. The compounds showing the most interesting pharmacological and bioavailability profiles were piperazine derivatives (EHT 8560 & EHT 9241; "non-selective" compounds), piperazine derivative EHT 5743 (highly "selective", highest activity compound in HCT116 cells) and morpholine compound EHT 1864.

These results thus illustrate the ability of the compounds of this invention, especially of piperazine derivatives EHT 5743, EHT 8560 & EHT 9241 and morpholine derivative EHT 1864 to affect tumor cell viability, migration and, to inhibit the formation of tubule (vessel-like structures).

2. In Vivo Zebrafish Assay

Compounds that were tested are: EHT 1864, EHT 9241, 2ME and CAI. 5 µM Flavopiridol was used as an internal positive control. Morphometric analysis of treated and non-treated zebrafish embryos using image analysis software allowed to quantify the inhibition of intersegmental vessels formation by the various compounds (see FIG. 6). EHT 1864 has a dose-dependent anti-angiogenic activity in the zebrafish embryo, and this activity is comparable to the activity of known anti-angiogenic compound 2ME and Flavopiridol. Interestingly, EHT 1864 seems to be much less toxic than reference compounds Flavopiridol and SU-5416 (not shown). Although EHT 9241 do display an anti-angiogenic activity (40% max inhibition), it is much less potent than EHT 1864 (77% max inhibition). Data obtained with CAI are not conclusive because of precipitation of the compound in the nutritive medium.

3. Toxicity Assays a. Screening Ames Test

Four compounds were tested through screening Ames test, namely EHT 1864, EHT 2725, EHT 8560 and EHT 9241. Under these experimental conditions, the test items did not show any mutagenic activity, with and without S9 mix, In Salmonella typhimurium TA 98 and TA 100 strains.

b. Screening Toxicity Test

Three compounds were tested, namely EHT 1864, EHT 8560 and EHT 9241. Overall, the three compounds were quite well tolerated up to 300 mg/kg/day. No death occurred during the study. Minimal clinical signs were observed with the three compounds. A mean body weight loss was noted in all groups at 300 mg/kg/day. Some limited biological changes (hematology and blood biochemistry) were noted.

TABLE 12

Cell viability assay (MTT; 10% FBS) after 6-day treatment

| Compound | HMEC1 IC50 μM | SEM | HCT116 IC50 μM | SEM | MDA-MB-231 IC50 μM | SEM | MCF7 IC50 μM | SEM | NIH 3T3 IC50 μM | SEM |
|---|---|---|---|---|---|---|---|---|---|---|
| EHT 0079 | 28.6 | | 12.5 | 3.2 | | | | | | |
| EHT 0371 | 88.7 | 9.0 | | | | | | | | |
| EHT 0566 | 3.0 | 0.2 | 1.5 | 0.3 | | | | | | |
| EHT 0785 | 9.6 | 0.8 | 1.9 | 0.9 | 8.2 | 0.5 | | | 11.6 | 1.9 |
| EHT 0872 | 28.4 | 4.7 | 9.3 | 0.9 | | | | | | |
| EHT 1006 | 9.5 | 0.1 | 0.9 | 0.0 | | | | | | |
| EHT 1426 | | | 18.0 | 0.2 | | | | | | |
| EHT 1494 | 1.8 | 0.3 | 1.6 | 0.1 | | | | | | |
| EHT 1593 | 13.2 | | 2.4 | 0.1 | | | | | 21.5 | |
| EHT 1864 | 27.4 | 1.1 | 2.7 | 0.6 | 9.3 | 1.4 | 5.6 | | 19.8 | 1.1 |
| EHT 2168 | 19.3 | | 6.0 | 1.6 | | | | | | |
| EHT 2218 | 19.3 | 3.8 | 3.7 | 0.6 | 5.0 | 0.5 | | | 26.0 | 0.7 |
| EHT 2272 | 38.2 | 5.9 | 3.0 | 0.4 | 12.5 | 0.1 | | | 38.8 | 14.6 |
| EHT 2725 | 28.1 | 1.9 | 2.7 | 0.2 | 9.3 | 2.1 | | | 24.8 | 0.2 |
| EHT 3411 | 62.4 | 11.8 | 14.1 | 6.3 | | | | | | |
| EHT 3664 | 10.0 | 1.0 | | | 6.3 | 1.2 | | | 9.8 | 2.0 |
| EHT 3726 | | | ~200.0 | | | | | | | |
| EHT 3788 | 7.1 | 0.4 | 2.1 | 0.2 | | | | | 8.8 | |
| EHT 3980 | 38.5 | 2.4 | 2.3 | 0.3 | | | | | | |
| EHT 4063 | ~200.0 | | ~200.0 | | | | | | | |
| EHT 4495 | | | 2.3 | | | | | | | |
| EHT 4687 | 39.1 | 2.6 | 5.5 | 1.6 | | | | | | |
| EHT 4745 | 9.8 | 0.9 | 4.1 | 0.3 | | | | | | |
| EHT 5430 | 20.1 | 4.2 | 2.1 | 0.1 | | | | | | |
| EHT 5743 | 8.0 | 2.0 | 0.4 | 0.2 | 8.8 | 0.6 | 1.2 | | 2.4 | 0.4 |
| EHT 5810 | 15.1 | | 8.4 | 0.7 | | | | | | |
| EHT 5847 | 31.6 | 3.4 | 6.1 | 0.6 | | | | | | |
| EHT 5881 | 17.5 | 4.5 | 0.6 | 0.1 | | | | | | |
| EHT 6060 | 19.1 | | 2.0 | 0.1 | | | | | | |
| EHT 6271 | 9.0 | 0.1 | 1.0 | 0.2 | | | | | | |
| EHT 6362 | | | 13.8 | 1.4 | | | | | | |
| EHT 6892 | | | 100.8 | 13.4 | | | | | | |
| EHT 7168 | 25.2 | 1.9 | 4.9 | 1.5 | 9.8 | 2.1 | | | 12.7 | 2.0 |
| EHT 7269 | 13.2 | | 4.6 | 1.3 | | | | | | |
| EHT 7365 | 8.3 | 0.6 | 5.4 | 0.8 | 3.7 | 0.1 | | | 6.5 | 0.5 |
| EHT 7370 | 12.1 | | 4.4 | | | | | | | |
| EHT 8560 | 6.1 | 0.4 | 3.8 | 0.3 | 3.1 | 0.5 | | | 5.1 | 0.1 |
| EHT 8791 | ~200.0 | | ~200.0 | | | | | | | |
| EHT 8817 | 41.0 | | 12.1 | 2.1 | | | | | | |
| EHT 8883 | 8.0 | | 0.3 | 0.0 | | | | | | |
| EHT 9014 | 20.1 | | 8.2 | 2.3 | | | | | | |
| EHT 9069 | 34.8 | 2.3 | 15.5 | 2.7 | 13.5 | | | | 41.3 | |
| EHT 9140 | 16.5 | 1.2 | 1.3 | 0.3 | 9.5 | 1.9 | | | 4.3 | 0.2 |
| EHT 9241 | 8.2 | 0.4 | 4.0 | 0.9 | 5.3 | 1.2 | 1.2 | | 8.7 | 0.3 |
| EHT 9317 | 11.7 | 1.5 | 2.3 | 0.5 | | | | | | |
| EHT 9358 | 18.4 | 6.2 | 0.55 | 0.02 | 2.3 | 0.3 | | | 7.7 | 0.5 |
| EHT 9376 | 8.2 | 1.1 | 0.9 | 0.1 | 11.5 | 3.5 | | | 8.1 | 2.7 |
| Taxol | 2.9E−3 | | 5.5E−3 | 1.0E−3 | 3.6E−3 | 0.6E−3 | | | ~50E−3 | |
| CAI | 28.4 | 2.1 | 1.0 | 0.2 | 1.3 | 0.4 | | | 5.8 | 3.1 |
| SU-6668 | 36.0 | 1.5 | 18.9 | 1.0 | 22.5 | 2.0 | | | 35.7 | 3.4 |
| 2ME | 2.1 | 0.1 | 0.8 | 0.0 | 0.3 | 0.0 | | | 2.4 | 0.7 |

TABLE 13

Cell viability assay (MTT; 0.5% FBS) after 6-day treatment

| Compound | HCT116 IC50 (μM) | SEM | MDA-MB-231 IC50 (μM) | SEM |
|---|---|---|---|---|
| EHT 1864 | 6.6 | 0.4 | 6.3 | 0.5 |
| EHT 2218 | 3.3 | 0.9 | | |
| EHT 2272 | 5.7 | 0.7 | | |
| EHT 2725 | 5.4 | 0.9 | 6.4 | 1.6 |
| EHT 8560 | 4.6 | 0.2 | 4.0 | 0.5 |
| EHT 9241 | 6.2 | 0.4 | 3.8 | 1.2 |
| EHT 9358 | 1.0 | 0.4 | | |
| 2ME | 3.1 | 0.8 | 15.4 | 10.8 |
| CAI | 0.6 | 0.0 | 0.4 | 0.2 |

TABLE 14

Cell viability assay (MTT; 10% FBS) after 3-day treatment

| Compound | DLD1 IC50 µM | SEM | HCT116 IC50 µM | SEM | MDA-MB-231 IC50 µM | SEM | MCF7 IC50 µM | SEM | HeLa IC50 µM | SEM |
|---|---|---|---|---|---|---|---|---|---|---|
| EHT 1864 | 21.9 | 3.5 | 6.1 | 1.3 | 9.9 | 2.2 | 15.2 |  | 23.3 | 6.4 |
| EHT 2725 | 12.2 |  | 9.9 | 4.3 | 19.5 | 2.9 | 7.3 |  | 20.9 | 5.3 |
| EHT 8560 | 5.6 |  | 4.0 | 0.8 | 9.0 | 3.6 | 9.2 | 0.3 | 4.4 | 1.3 |
| EHT 9241 | 8.1 | 1.4 | 5.7 | 0.6 | 11.1 | 1.3 | 7.5 |  | 5.7 | 1.8 |
| 5FU | 5.44 | 1.14 | 7.83 | 0.69 |  |  |  |  |  |  |
| Taxol (nM) |  |  |  |  | 4.25E−03 | 2.00E−03 |  |  |  |  |

TABLE 15

Cell viability assay (MTT; 10% FBS) after 16-hours treatment

| Compound | HCT116 IC50 µM | SEM | MDA-MB-231 IC50 µM | SEM | NIH 3T3 IC50 µM | SEM | HepG2 IC50 µM | SEM | Primary Hepatocytes IC50 µM | SEM |
|---|---|---|---|---|---|---|---|---|---|---|
| EHT 1864 | 37.0 | 16.4 | 126.5 |  | 69.3 | 7.1 | 59.98 |  | >50 |  |
| EHT 2725 |  |  |  |  |  |  | 45.2 |  | >50 |  |
| EHT 8560 |  |  |  |  |  |  | 9.754 |  | 17.26 |  |
| EHT 9241 | 31.3 |  | 48.4 |  | 25.6 |  | 11.3 |  | 29.64 |  |
| 2ME | 127.5 |  | >100 |  | >150 |  |  |  |  |  |
| CAI | 44.1 |  | >50 |  | 95.9 |  |  |  |  |  |

BIBLIOGRAPHY

Bauer K S, Cude K J, Dixon S C, Kruger E A, Figg W D. Carboxyamido-triazole inhibits angiogenesis by blocking the calcium-mediated nitric-oxide synthase-vascular endothelial growth factor pathway. *J Pharmacol Exp Ther.* 2000 January; 292(1):31-7.

Carmichael J, DeGraff W G, Gazdar A F, Minna J D, Mitchell J B. Evaluation of a tetrazolium-based semiautomated colorimetric assay: assessment of radiosensitivity. *Cancer Res.* 1987 Feb. 15; 47(4):943-6.

Di Ciano C, Nie Z, Szaszi K, Lewis A, Uruno T, Zhan X, Rotstein O D, Mak A, Kapus A. Osmotic stress-induced remodelling of the cortical cytoskeleton. *Am J Physiol Cell Physiol.* 2002 September; 283(3):C850-65.

Kohn E C, Liotta L A. L651582: a novel antiproliferative and antimetastasis agent. *J Natl Cancer Inst.* 1990 Jan. 3; 82(1):54-60.

Kruger E A, Figg W D. Protein binding alters the activity of suramin, carboxyamidotriazole, and UCN-01 in an ex vivo rat aortic ring angiogenesis assay. *Clin Cancer Res.* 2001 Jul.; 7(7):1867-72.

Murphy M J Jr, Fushimi F, Parchment R E, Barbera-Guillem E. Automated imaging and quantitation of tumor cells and CFU-GM colonies in microcapillary cultures: toward therapeutic index-based drug screening. *Invest New Drugs.* 1996; 13(4):303-14.

Nobes C D, Hawkins P, Stephens L, Hall A., Activation of the small GTP-binding proteins rho and rac by growth factor receptors. *J Cell Sci.* 1995 January; 108 (Pt 1):225-33.

Ridley A J, Paterson H F, Johnston C L, Diekmann D, Hall A. The small GTP-binding protein rac regulates growth factor-induced membrane ruffling. *Cell.* 1992 Aug. 7; 70(3):401-10.

Ridley A J, Hall A. The small GTP-binding protein rho regulates the assembly of focal adhesions and actin stress fibers in response to growth factors. *Cell.* 1992 Aug. 7; 70(3):389-99.

Rust W L, Huff J L, Plopper G E. Screening assay for promigratory/antimigratory compounds. *Anal Biochem.* 2000 Apr. 10; 280(1):11-9.

Serbedzija G N, Flynn E, Willett C E. Zebrafish angiogenesis: a new model for drug screening. *Angiogenesis.* 1999; 3(4):353-9.

Takai Y. Sasaki T, Matozaki T. Small GTP-binding proteins. *Physiol Rev.* 2001 January; 81 (1):153-208.

Wasilenko W J, Palad A J, Somers K D, Blackmore P F, Kohn E C, Rhim J S, Wright G L Jr, Schellhammer P F. Effects of the calcium influx inhibitor carboxyamidotriazole on the proliferation and invasiveness of human prostate tumor cell lines. *Int J Cancer.* 1996 Oct. 9; 68(2):259-64.

Wu Y, Palad A J, Wasilenko W J, Blackmore P F, Pincus W A, Schechter G L, Spoonster J R, Kohn E C, Somers K D. Inhibition of head and neck squamous cell carcinoma growth and invasion by the calcium influx inhibitor carboxyamidotriazole. *Clin Cancer Res.* 1997 Nov.; 3(11): 1915-21.

The invention claimed is:

1. A compound having a general formula (I):

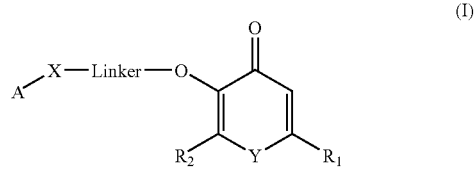

wherein:

R₁ is selected from the group consisting of:

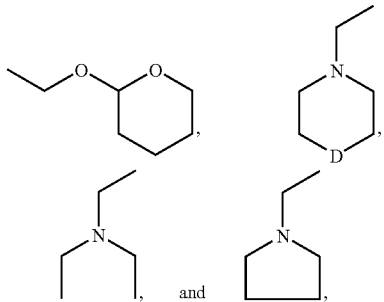

R₂ represents a hydrogen atom, an alkyl or alkenyl group containing from 3 to 6 carbon atoms;

D represents an oxygen atom, NR₃, CR'R" or a sulfur atom;

X represents a sulfur atom;

Y represents an oxygen atom;

R₃ represents a hydrogen, an alkyl group, a carboxylate group, an acyl group, a carboxamide group or a SO₂-alkyl group;

R' and R", identical or different, represent a hydrogen atom or an alkyl radical;

"linker" represents (CH₂)ₙ, wherein n represents an integer between 1 and 10 inclusive, optionally interrupted by an heteroatom or a carbonyl group, or an aryldialkyl;

A represents a group selected from:

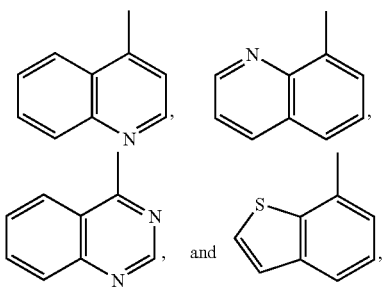

optionally A is substituted, its tautomers, optical and geometrical isomers, racemates, salts, hydrates and mixtures thereof.

2. The compound according to claim 1, wherein it presents one or more characteristics selected in the group consisting of:

"linker" represents (CH₂)ₙ, wherein n is from 2 to 9 inclusive, or the meta, ortho or para-xylenyl groups, —CH₂CH₂OCH₂CH₂— and —(C=O) CH₂CH₂CH₂CH₂—);

R₁ is

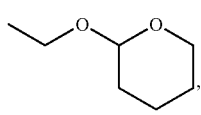

—CH₂N(Et₂) and —CH₂pyrrolidine,

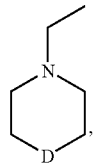

wherein D is oxygen, sulfur, —CH₂— or NR₃, wherein R₃ optionally represents H or an alkyl group;

R₂ is a hydrogen atom; and

A is a substituted group.

3. The compound according to claim 1, wherein A is substituted with at least one substituent selected in the group consisting of: a hydrogen atom, a halogen atom, a hydroxyl group, a (C₁-C₁₀)alkyl group, an alkenyl group, an (C₁-C₁₀) alkanoyl group, a (C₁-C₁₀)alkoxy group, a (C₁-C₁₀)alkoxycarbonyl group, an aryl group, an aralkyl group, an arylcarbonyl group, a mono- or poly-cyclic hydrocarbon group, a —NHCO(C₁-C₆)alkyl group, —NO₂, —CN, a —NR₅R₆ group or a trifluoro(C₁-C₆)alkyl group, R₅ and R₆, independently from each other, are selected from the group consisting of a hydrogen atom, an alkyl group having from 1 to 10 carbon atoms, an aryl and an aralkyl.

4. The compound according to claim 1, wherein A is a substituted group and at least one of the substituents is an halogen atom.

5. The compound according to claim 1, wherein at least one of the substituents of A represents a hydrogen atom, a methyl group, a propyl group, an ethoxy group, an halogen atom or the CF₃ group.

6. The compound according to claim 1, which is selected from the group consisting of:

2-(Tetrahydro-pyran-2-yloxymethyl)-5-[5-(7-trifluoromethyl-quinolin-4-ylsulfanyl)-pentyloxy]-4H-pyran-4-one (EHT 9376), 2-(Tetrahydro-pyran-2-yloxymethyl)-5-[4-(7-trifluoromethyl-quinolin-4-ylsulfanyl)-butoxy]-4H-pyran-4-one (EHT 4745), 2-(Tetrahydro-pyran-2-yloxymethyl)-5-[6-(7-trifluoromethyl-quinolin-4-ylsulfanyl)-hexyloxy]-4H-pyran-4-one (EHT 6271), 2-(4-Methyl-piperazin-1-ylmethyl)-5-[5-(7-trifluoromethyl-quinolin-4-ylsulfanyl)-pentyloxy]-4H-pyran-4-one (EHT 7365), 2-Morpholin-4-ylmethyl-5-[5-(7-trifluoromethyl-quinolin-4-ylsulfanyl)-pentyloxy]-4H-pyran-4-one (EHT 7168), 5-(5-(7-(Trifluoromethyl)quinolin-4-ylthio)pentyloxy)-2-((piperidin-1-yl)methyl)-4H-pyran-4-one (EHT 9317)

5-(5-(7-(Trifluoromethyl)quinolin-4-ylthio)pentyloxy)-2-(thiomorpholino-methyl)-4H-pyran-4-one (EHT 5430)

2-((Diethylamino)methyl)-5-(5-(7-(trifluoromethyl) quinolin-4-ylthio)pentyloxy)-4H-pyran-4-one (EHT 7370)

5-((3-((7-(Trifluoromethyl)quinolin-4-ylthio)methyl)phenyl)methoxy)-2-(morpholinomethyl)-4H-pyran-4-one (EHT 2725), 5-((4-((7-(Trifluoromethyl)quinolin-4-ylthio)methyl)phenyl)methoxy)-2-(morpholinomethyl)-4H-pyran-4-one (EHT 2218), 5-((2-((7-(Trifluoromethyl)quinolin-4-ylthio)methyl)phenyl)methoxy)-2-(morpholinomethyl)-4H-pyran-4-one (EHT 9069), 5-(5-(7-(Trifluoromethyl)quinolin-4-ylthio)pentyloxy)-2-((4-acetylpiperazin-1-yl)methyl)-4H-pyran-4-one (EHT 3980),
4-((5-(5-(7-(Trifluoromethyl)quinolin-4-ylthio)pentyloxy)-4-oxo-4H-pyran-2-yl)methyl)-N,N-diethylpiperazine-1-carboxamide (EHT 5743),
5-(5-(7-(Trifluoromethyl)quinolin-4-ylthio)pentyloxy)-2-((4-(pivaloyl)piperazin-1-yl)methyl)-4H-pyran-4-one (EHT 0785),
4-((5-(5-(7-(Trifluoromethyl)quinolin-4-ylthio)pentyloxy)-4-oxo-4H-pyran-2-yl)methyl)-N,N-di-isopropylpiperazine-1-carboxamide (EHT 0566),
5-(5-(7-(Trifluoromethyl)quinolin-4-ylthio)pentyloxy)-2-((4-methylsulfonylpiperazin-1-yl)methyl)-4H-pyran-4-one (EHT 8366),
4-((5-(5-(7-(Trifluoromethyl)quinolin-4-ylthio)pentyloxy)-4-oxo-4H-pyran-2-yl)methyl)-N-tert-butylpiperazine-1-carboxamide (EHT 3664),
4-((5-(5-(7-(Trifluoromethyl)quinolin-4-ylthio)pentyloxy)-4-oxo-4H-pyran-2-yl)methyl)-N-methylpiperazine-1-carboxamide (EHT 4495),
5-(2-(2-(7-(Trifluoromethyl)quinolin-4-ylthio)ethoxy)ethoxy)-2-(morpholinomethyl)-4H-pyran-4-one (EHT 0371),
5-(5-(7-(Trifluoromethyl)quinolin-4-ylthio)pentyloxy)-2-(morpholinomethyl)-4H-pyran-4-one dihydrochloride (EHT 1864),
5-((3-((7-(Trifluoromethyl)quinolin-4-ylthio)methyl)phenyl)methoxy)-2-(morpholinomethyl)-4H-pyran-4-one dihydrochloride (EHT 0434),
tert-Butyl 4-((5-(5-(7-(trifluoromethyl)quinolin-4-ylthio)pentyloxy)-4-oxo-4H-pyran-2-yl)methyl)piperazine-1-carboxylate (EHT 9358),
5-(5-(7-(Trifluoromethyl)quinolin-4-ylthio)pentyloxy)-2-((4-methylpiperazin-1-yl)methyl)-4H-pyran-4-one trihydrochloride (EHT 9241),
5-(5-(7-(Trifluoromethyl)quinolin-4-ylthio)pentyloxy)-2-((piperazin-1-yl)methyl)-4H-pyran-4-one trihydrochloride (EHT 8560),
5-(2-(7-(Trifluoromethyl)quinolin-4-ylthio)ethoxy)-2-((tetrahydro-2H-pyran-2-yloxy)methyl)-4H-pyran-4-one (EHT 5575),
5-(8-(7-(Trifluoromethyi)quinolin-4-ylthio)octyloxy)-2-((tetrahydro-2H-pyran-2-yloxy)methyl)-4H-pyran-4-one (EHT 1006), and
5-(7-(Trifluoromethyl)quinolin-4-ylthio)heptyloxy)-2-((tetrahydro-2H-pyran-2-yloxy)methyl)-4H-pyran-4-one (EHT 8883).

7. The compound according to claim 6, which is EHT 9241, its free base EHT 7365, EHT 8560, EHT 1864, its free base EHT 7168 or EHT 5743.

8. A pharmaceutical composition comprising at least one compound according to claim 1 and a pharmaceutically acceptable vehicle or support.

9. The compound of claim 1 wherein said heteroatom is selected from the group consisting of N, O, S and P, or said aryldialkyl is xylenyl.

10. The compound of claim 2 wherein n is a value of 4 to 7.

11. The compound of claim 2 wherein said alkyl is a methyl radical.

12. The compound of claim 3 wherein said halogen is F, Cl or Br.

13. The compound of claim 4 wherein said halogen atom is chlorine or fluorine.

14. The compound of claim 5 wherein all of the substituents of A represents a hydrogen atom, a methyl group, a propyl group, an ethoxy group, an halogen atom or the $CF_3$ group.

15. The compound of claim 5 wherein said halogen atom is chlorine or fluorine.

* * * * *